(12) United States Patent
Kawahata et al.

(10) Patent No.: US 10,793,575 B2
(45) Date of Patent: Oct. 6, 2020

(54) OXOISOQUINOLINE DERIVATIVES

(71) Applicant: CARNA BIOSCIENCES, INC., Hyogo (JP)

(72) Inventors: Wataru Kawahata, Kobe (JP); Takao Kiyoi, Kobe (JP); Takayuki Irie, Kobe (JP); Tokiko Asami, Kobe (JP); Masaaki Sawa, Ibaraki (JP); Shigeki Kashimoto, Osaka (JP)

(73) Assignee: CARNA BIOSCIENCES, INC., Hyogo (JP)

( * ) Notice: Subject to any disclaimer, the term of this patent is extended or adjusted under 35 U.S.C. 154(b) by 0 days.

(21) Appl. No.: 16/463,493

(22) PCT Filed: Nov. 24, 2017

(86) PCT No.: PCT/JP2017/042172
§ 371 (c)(1),
(2) Date: May 23, 2019

(87) PCT Pub. No.: WO2018/097234
PCT Pub. Date: May 31, 2018

(65) Prior Publication Data
US 2019/0359616 A1  Nov. 28, 2019

(30) Foreign Application Priority Data

Nov. 25, 2016 (JP) .................... 2016-229262
Sep. 29, 2017 (JP) .................... 2017-191488

(51) Int. Cl.
*C07D 487/04* (2006.01)
*A61P 35/00* (2006.01)
*C07D 473/00* (2006.01)

(52) U.S. Cl.
CPC .......... *C07D 487/04* (2013.01); *C07D 473/00* (2013.01)

(58) Field of Classification Search
CPC .................................................. C07D 487/04
See application file for complete search history.

(56) References Cited

U.S. PATENT DOCUMENTS

| 2015/0011751 A1 | 1/2015 | Kawahata et al. | |
| 2015/0064196 A1* | 3/2015 | Thakkar | C07D 413/14 424/144.1 |
| 2016/0168122 A1 | 6/2016 | Kawahata et al. | |

FOREIGN PATENT DOCUMENTS

| CN | 104211703 | 12/2014 |
| WO | 2013/157021 | 10/2013 |
| WO | 2013/157022 | 10/2013 |
| WO | 2013/133367 | 7/2015 |
| WO | 2015/012149 | 3/2017 |

OTHER PUBLICATIONS

De Lucca et al. Bioorganic & Medicinal Chemistry 23 (Aug. 17, 2016) 891-901. (Year: 2016).*
Zhao et al. Bioorganic & Medicinal Chemistry 23 (2015) 891-901. Available online Nov. 6, 2014. (Year: 2015).*
International Search Report dated Feb. 6, 2018 in International Application No. PCT/JP2017/042172.
International Preliminary Report on Patentability dated Feb. 6, 2018 in International Application No. PCT/JP2017/042172.
Satterthwaite et al., "The role of Bruton's tyrosine kinase in B-cell development and function: a genetic perspective", Immunological Reviews 2000, vol. 175, pp. 120-127.
Tomohiro Kurosaki, "Functional dissection of BCR signaling pathways", Current Opinion in Immunology, 2000, 12, pp. 276-281.
Davis et al., "Chronic active B-cell-receptor signalling in diffuse large B-cell lymphoma", Nature, vol. 463, Jan. 2010, pp. 88-92.
Ellmeier et al., "Tec family kinases: regulation of FcεR1-mediated mast-cell activation", FEBS Journal, 2011, 278, pp. 1990-2000.
Halcomb et al., "Btk regulates localization, in vivo activation, and class switching of anti-DNA B cells", Mol Immunol. Dec. 2008, 46(2), pp. 233-241.
Jansson et al., "Genes on the X chromosome affect development of collagen-induced arthritis in mice", Clin Exp Immunol 1993, 94, pp. 459-465.
Cheng et al., "Functional characterization of $BTK^{C481S}$ mutation that confers ibrutinib resistance: exploration of alternative kinase inhibitors", Leukemia, 2015, 29, pp. 895-900.
Grassilli et al., "A novel oncogenic BTK isoform is overexpressed in colon cancers and required for RAS-mediated transformation", Oncogene, 2016, 35, pp. 4386-4378.

(Continued)

*Primary Examiner* — Emily A Bernhardt
(74) *Attorney, Agent, or Firm* — Wenderoth, Lind & Ponack, L.L.P.

(57) ABSTRACT

An oxoisoquinoline compound of the following formula:

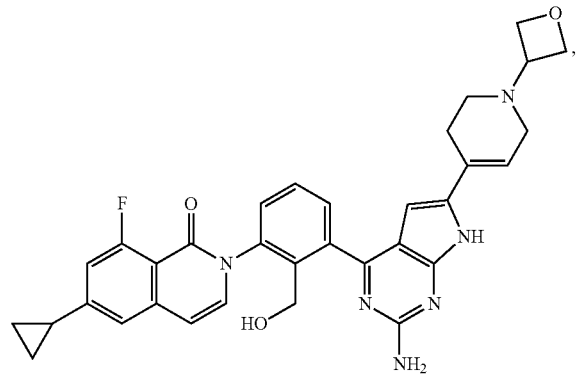

or a pharmaceutically acceptable salt thereof; a pharmaceutical composition comprising the oxoisoquinoline compound or salt; and a method for treating B-cell lymphoma comprising administering the oxoisoquinoline compound or salt to a patient.

3 Claims, No Drawings

(56) References Cited

OTHER PUBLICATIONS

Zhao et al., "Pyrrolo[2,3-b]pyridine derivatives as potent Bruton's tyrosine kinase inhibitors", Bioorganic & Medicinal Chemistry, 23: 4344-4353 (2015).
Extended European Search Report dated May 29, 2020 in corresponding European Patent Application No. 17874560.0.

\* cited by examiner

OXOISOQUINOLINE DERIVATIVES

TECHNICAL FIELDS

The present invention relates to a pharmaceutical, and particularly to a novel oxoisoquinoline derivative having a BTK-inhibitory effect or a pharmaceutically acceptable salt thereof.

BACKGROUND ART

Bruton's tyrosine kinase (BTK) is a member of the Tec family of non-receptor tyrosine kinases, and is an important signaling enzyme which is expressed in all hematopoietic cell types except for T lymphocytes and natural killer cells. BTK is an important control factor associated with survival, differentiation, proliferation and activation of B-cells, and takes an important role in signaling of B-cells (Non-Patent Documents 1 and 2). A B-cell receptor (BCR) of the cell surface signals into cells through BTK existing in the downstream of BCR and, therefore, it is considered that abnormal activation of the signaling pathway of B-cells accelerates proliferation and survival of cancer cells of B-cell lymphoma, chronic lymphocytic leukemia and the like (Non-Patent Document 3). It is known that BTK also plays an important role in the signal pathway of a large number of other cells, and it is said that BTK is involved in allergic diseases, self-immune diseases, inflammatory diseases and the like (Non-Patent Document 1).

For example, it is known that BTK plays an important role for signaling of a high affinity IgE receptor (FcεRI) in mast cells, and degranulation decreases and the production of proinflammatory cytokines decreases in BTK-deficient mast cells (Non-Patent Document 4). It is suggested that BTK is involved in systemic lupus erythematosus (SLE) in a test of a BTK-deficient mouse (Non-Patent Document 5). Furthermore, the BTK mutant mouse exhibits resistance to the onset of collagen-induced arthritis (Non-Patent Document 6).

Ibrutinib is an irreversible BTK-inhibitor and used for treating for B-cell tumor as an anticancer drug. Recently it was found that ibrutinib-tolerance was generated due to C481S-mutation of BTK in the treatment with ibrutinib (Non-Patent Document 7). Also it is reported that p65 BTK, which is an isoform of BTK, was expressed at a downstream of RAS signal in a solid cancer other than a blood cancer, and involved in proliferation of a solid cancer such as a cell of colon cancer (Non-Patent Document 8). Therefore, the compound having a BTK inhibitory activity is useful for the treatment of diseases which are involved in BTK signaling, for example, cancer, B-cell lymphoma, and chronic lymphocytic leukemia, and also a solid cancer in which p65BTK is expressed. Moreover it is useful for the treatment of allergic diseases, self-immune diseases and inflammatory diseases.

Additionally a BTK-inhibitor which is effective for treating a cancer having BTK-mutation and tolerant to an irreversible BTK-inhibitor such as ibrutinib is required.

Triazine derivative are reported by the present inventors as a compound having a BTK-inhibiting activity (Patent Document 1 and 2). Compounds similar to those in the present invention are also disclosed (Patent Document 3 and 4). But an oxoisoquinoline derivative of the present invention is not disclosed therein.

PRIOR ART DOCUMENT(S)

Patent Document(s)

[Patent Document 1] WO2013/133367
[Patent Document 2] WO2015/012149
[Patent Document 3] WO2013/157022
[Patent Document 4] CN104211703

Non-Patent Document(s)

[Non-Patent Document 1] Satterthwaite, A. B. and Witte, O. N., Immunol. Rev., 2000, 175, 120-127.
[Non-Patent Document 2] Kurosaki, T., Curr. Opin. Immunol., 2000, 12, 276-281.
[Non-Patent Document 3] Davis, R. E. et al., Nature, 2010, 463, 88-92.
[Non-Patent Document 4] Ellmeier, W., et al., FEBS J., (2011), 278, 1990-2000.
[Non-Patent Document 5] Halcomb, K. E., Mol. Immunol., 2008, 46(2), 233-241.
[Non-Patent Document 6] Jansson, L. and Holmdahl, R., Clin. Exp. Immunol., 1993, 94, 459-465.
[Non-Patent Document 7] Cheng, S. et al., Leukemia, 2015, 29, 895-900.
[Non-Patent Document 8] Grassili. E., et al., Oncogene, 2016, 35, 4368-4378.

DISCLOSURE OF INVENTION

Problem to be Solved by the Invention

An object of the present invention is to provide a pharmaceutical, particularly a novel oxoisoquinoline derivative having a BTK inhibitory effect, or a pharmaceutically acceptable salt thereof.

Means for Solving Problem

The present invention is achieved by the following (1) to (6):
(1) an oxoisoquinoline derivative of the formula (I)

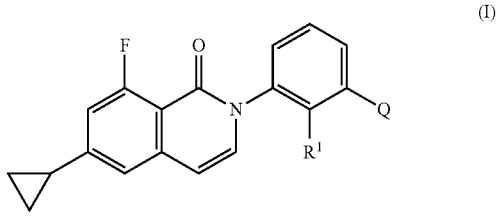

wherein $R^1$ is an optionally substituted lower alkyl,
Q is a structure selected from the following structures (a), (b) and (c);

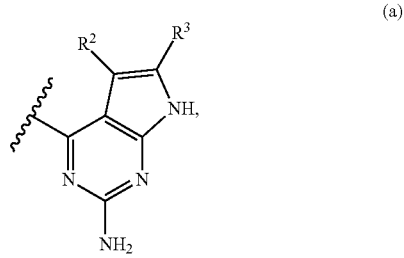

-continued (b)
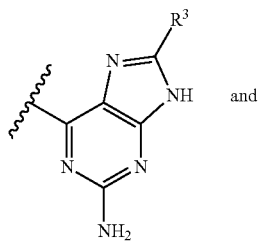 and (c)
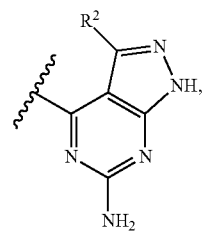

wherein R² and R³ are independently a hydrogen atom, an optionally substituted lower alkyl group, an optionally substituted cycloalkyl group, an optionally substituted aryl group, an optionally substituted heteroaryl group or an optionally substituted heterocyclic group, or a pharmaceutically acceptable salt thereof;

(2) the oxoisoquinoline derivative according to (1) above, wherein Q is a structure (a), and R¹ is a hydroxymethyl group, (3) an oxoisoquinoline derivative of the formula (Ia):

(Ia)
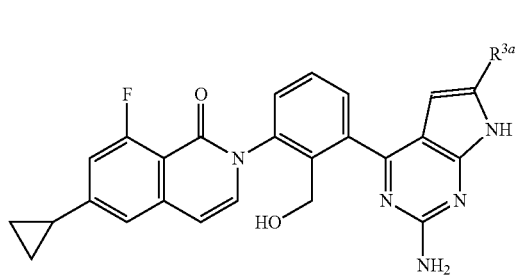

wherein $R^{3a}$ is an optionally substituted tetrahydropyridyl group, or a pharmaceutically acceptable salt thereof;

(4) the oxoisoquinoline derivative of the formula (Ia), wherein a substituent of the tetrahydropyridine group is selected from the group consisting of an oxetanyl group, an acetyl group, a propionyl group, a morpholinoacetyl group, a dimethylcarbamoyl group, a pyrrolidinecarbonyl group, a methylsulfonyl group and an isopropylsulfonyl group, or a pharmaceutically acceptable salt thereof;

(5) the oxoisoquinoline derivative of the formula (Ib);

(Ib)
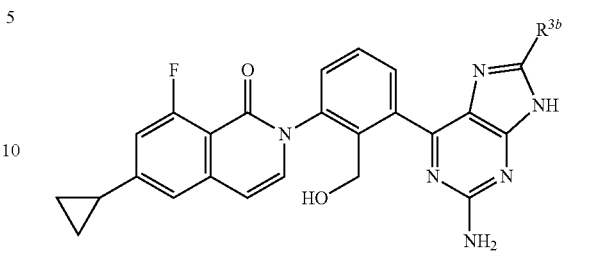

wherein $R^{3b}$ is a phenyl group optionally substituted with a lower alkyl group or a pharmaceutically acceptable salt thereof;

(6) a compound selected from the group consisting of the following compounds;

2-[3-(2-amino-6-phenyl-7H-pyrrolo[2,3-d]pyrimidin-4-yl)-2-(hydroxymethyl)phenyl]-6-cyclopropyl-8-fluoroisoquinolin-1(2H)-one (Example 1)

2-[3-(2-amino-8-phenyl-9H-purin-6-yl)-2-(hydroxymethyl)phenyl]-6-cyclopropyl-8-fluoroisoquinolin-1(2H)-one (Example 2)

2-[3-(6-amino-3-phenyl-1H-pyrazolo[3,4-d]pyrimidin-4-yl)-2-(hydroxymethyl)phenyl]-6-cyclopropyl-8-fluoroisoquinolin-1(2H)-one (Example 3)

2-[3-(2-amino-9H-purin-6-yl)-2-(hydroxymethyl)phenyl]-6-cyclopropyl-8-fluoroisoquinolin-1(2H)-one (Example 4)

2-[3-(6-amino-1H-pyrazolo[3,4-d]pyrimidin-4-yl)-2-(hydroxymethyl)phenyl]-6-cyclopropyl-8-fluoroisoquinolin-1(2H)-one (Example 5)

2-[3-(2-amino-7H-pyrrolo[2,3-d]pyrimidin-4-yl)-2-(hydroxymethyl)phenyl]-6-cyclopropyl-8-fluoroisoquinolin-1(2H)-one (Example 6)

2-[3-(2-amino-6-methyl-7H-pyrrolo[2,3-d]pyrimidin-4-yl)-2-(hydroxymethyl)phenyl]-6-cyclopropyl-8-fluoroisoquinolin-1(2H)-one (Example 7)

2-[3-(2-amino-6-{4-[(4-methylpiperazin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 8)

2-[3-(2-amino-6-cyclopropyl-7H-pyrrolo[2,3-d]pyrimidin-4-yl)-2-(hydroxymethyl)phenyl]-6-cyclopropyl-8-fluoroisoquinolin-1(2H)-one (Example 9)

2-[3-(6-amino-3-methyl-1H-pyrazolo[3,4-d]pyrimidin-4-yl)-2-(hydroxymethyl)phenyl]-6-cyclopropyl-8-fluoroisoquinolin-1(2H)-one (Example 10)

2-{3-[2-amino-6-(hydroxymethyl)-7H-pyrrolo[2,3-d]pyrimidin-4-yl]-2-(hydroxymethyl)phenyl}-6-cyclopropyl-8-fluoroisoquinolin-1(2H)-one (Example 11)

2-[3-(2-amino-8-cyclopropyl-9H-purin-6-yl)-2-(hydroxymethyl)phenyl]-6-cyclopropyl-8-fluoroisoquinolin-1(2H)-one (Example 12)

2-{3-[2-amino-6-(1-methyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one (Example 13)

2-{3-[2-amino-6-(2-methoxyphenyl)-7H-pyrrolo[2,3-d]pyrimidin-4-yl]-2-(hydroxymethyl)phenyl}-6-cyclopropyl-8-fluoroisoquinolin-1(2H)-one (Example 14)

2-{3-[2-amino-6-(3-methoxyphenyl)-7H-pyrrolo[2,3-d]pyrimidin-4-yl]-2-(hydroxymethyl)phenyl}-6-cyclopropyl-8-fluoroisoquinolin-1(2H)-one (Example 15)

2-{3-[2-amino-6-(4-methoxyphenyl)-7H-pyrrolo[2,3-d]pyrimidin-4-yl]-2-(hydroxymethyl)phenyl}-6-cyclopropyl-8-fluoroisoquinolin-1(2H)-one (Example 16)

2-{3-[2-amino-6-(pyridin-3-yl)-7H-pyrrolo[2,3-d]pyrimidin-4-yl]-2-(hydroxymethyl)phenyl}-6-cyclopropyl-8-fluoroisoquinolin-1(2H)-one (Example 17)

2-{3-[2-amino-8-(3-methoxyphenyl)-9H-purin-6-yl]-2-(hydroxymethyl)phenyl}-6-cyclopropyl-8-fluoroisoquinolin-1(2H)-one (Example 18)

2-{3-[2-amino-6-(pyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 19)

2-{3-[6-amino-3-(4-methoxyphenyl)-1H-pyrazolo[3,4-d]pyrimidin-4-yl]-2-(hydroxymethyl)phenyl}-6-cyclopropyl-8-fluoroisoquinolin-1(2H)-one (Example 20)

2-{3-[6-amino-3-(2-methoxyphenyl)-1H-pyrazolo[3,4-d]pyrimidin-4-yl]-2-(hydroxymethyl)phenyl}-6-cyclopropyl-8-fluoroisoquinolin-1(2H)-one (Example 21)

2-{3-[6-amino-3-(3-methoxyphenyl)-1H-pyrazolo[3,4-d]pyrimidin-4-yl]-2-(hydroxymethyl)phenyl}-6-cyclopropyl-8-fluoroisoquinolin-1(2H)-one (Example 22)

2-(3-{2-amino-6-[1-(oxetan-3-yl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 23)

2-{3-[2-amino-8-(2-methoxyphenyl)-9H-purin-6-yl]-2-(hydroxymethyl)phenyl}-6-cyclopropyl-8-fluoroisoquinolin-1(2H)-one (Example 24)

2-{3-[2-amino-8-(pyridin-3-yl)-9H-purin-6-yl]-2-(hydroxymethyl)phenyl]-6-cyclopropyl-8-fluoroisoquinolin-1(2H)-one (Example 25)

2-(3-{2-amino-6-[4-(morpholinomethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 26)

4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}benzonitrile (Example 27)

2-[3-(2-amino-5-phenyl-7H-pyrrolo[2,3-d]pyrimidin-4-yl)-2-(hydroxymethyl)phenyl]-6-cyclopropyl-8-fluoroisoquinolin-1(2H)-one (Example 28)

2-{3-[2-amino-6-(3-fluorophenyl)-7H-pyrrolo[2,3-d]pyrimidin-4-yl]-2-(hydroxymethyl)phenyl}-6-cyclopropyl-8-fluoroisoquinolin-1(2H)-one (Example 29)

N-({2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}methyl)acrylamide (Example 30)

2-{3-[2-amino-8-(1-methyl-1H-pyrazol-4-yl)-9H-purin-6-yl]-2-(hydroxymethyl)phenyl}-6-cyclopropyl-8-fluoroisoquinolin-1(2H)-one (Example 31)

2-{3-[2-amino-6-(thiophen-3-yl)-7H-pyrrolo[2,3-d]pyrimidin-4-yl]-2-(hydroxymethyl)phenyl}-6-cyclopropyl-8-fluoroisoquinolin-1(2H)-one (Example 32)

2-{3-[2-amino-6-(2-fluorophenyl)-7H-pyrrolo[2,3-d]pyrimidin-4-yl]-2-(hydroxymethyl)phenyl}-6-cyclopropyl-8-fluoroisoquinolin-1(2H)-one (Example 33)

2-{3-[2-amino-6-(4-fluorophenyl)-7H-pyrrolo[2,3-d]pyrimidin-4-yl]-2-(hydroxymethyl)phenyl}-6-cyclopropyl-8-fluoroisoquinolin-1(2H)-one (Example 34)

2-{3-[2-amino-6-(2,4-difluorophenyl)-7H-pyrrolo[2,3-d]pyrimidin-4-yl]-2-(hydroxymethyl)phenyl}-6-cyclopropyl-8-fluoroisoquinolin-1(2H)-one (Example 35)

2-{3-[2-amino-6-(3,4-difluorophenyl)-7H-pyrrolo[2,3-d]pyrimidin-4-yl]-2-(hydroxymethyl)phenyl}-6-cyclopropyl-8-fluoroisoquinolin-1(2H)-one (Example 36)

2-(3-{2-amino-6-[4-(trifluoromethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 37)

2-(3-{2-amino-6-[4-(trifluoromethoxy)phenyl]-7H-pyrrolo[2,3-d]pyrimidin-4-yl}-2-(hydroxymethyl)phenyl)-6-cyclopropyl-8-fluoroisoquinolin-1(2H)-one (Example 38)

2-{3-[2-amino-6-(aminomethyl)-7H-pyrrolo[2,3-d]pyrimidin-4-yl]-2-(hydroxymethyl)phenyl}-6-cyclopropyl-8-fluoroisoquinolin-1(2H)-one (Example 39)

2-(3-{2-amino-6-[3-(trifluoromethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 40)

2-(3-{2-amino-6-[4-(methylsulfonyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 41)

2-{3-[2-amino-6-(6-fluoropyridin-2-yl)-7H-pyrrolo[2,3-d]pyrimidin-4-yl]-2-(hydroxymethyl)phenyl}-6-cyclopropyl-8-fluoroisoquinolin-1(2H)-one (Example 42)

2-{3-[2-amino-6-(2-fluoropyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 43)

2-{3-[2-amino-6-(3,5-difluorophenyl)-7H-pyrrolo[2,3-d]pyrimidin-4-yl]-2-(hydroxymethyl)phenyl}-6-cyclopropyl-8-fluoroisoquinolin-1(2H)-one (Example 44)

2-{3-[2-amino-6-(5-fluoropyridin-2-yl)-7H-pyrrolo[2,3-d]pyrimidin-4-yl]-2-(hydroxymethyl)phenyl}-6-cyclopropyl-8-fluoroisoquinolin-1(2H)-one (Example 45)

2-{3-[2-amino-6-(5-fluoropyridin-3-yl)-7H-pyrrolo[2,3-d]pyrimidin-4-yl]-2-(hydroxymethyl)phenyl}-6-cyclopropyl-8-fluoroisoquinolin-1(2H)-one (Example 46)

2-(3-{2-amino-6-[6-(methylamino)pyridin-3-yl]-7H-pyrrolo[2,3-d]pyrimidin-4-yl}-2-(hydroxymethyl)phenyl)-6-cyclopropyl-8-fluoroisoquinolin-1(2H)-one (Example 47)

2-{3-[2-amino-6-(6-morpholinopyridin-3-yl)-7H-pyrrolo[2,3-d]pyrimidin-4-yl]-2-(hydroxymethyl)phenyl}-6-cyclopropyl-8-fluoroisoquinolin-1(2H)-one (Example 48)

2-{3-[2-amino-6-(2-methoxypyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 49)

2-(3-{2-amino-6-[2-(methylamino)pyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 50)

2-[3-(2-amino-6-{4-[(dimethylamino)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 51)

2-[3-(2-amino-6-{4-[(diethylamino)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 52)

2-(3-{2-amino-6-[4-(pyrrolidin-1-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 53)

2-(3-{2-amino-6-[4-(piperidin-1-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 54)

2-[3-(2-amino-6-{4-[(4-methyl-3-oxopiperazin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 55)

2-{3-[2-amino-6-(p-tolyl)-7H-pyrrolo[2,3-d]pyrimidin-4-yl]-2-(hydroxymethyl)phenyl}-6-cyclopropyl-8-fluoroisoquinolin-1(2H)-one (Example 56)

2-{3-[2-amino-6-(tert-butyl)-7H-pyrrolo[2,3-d]pyrimidin-4-yl]-2-(hydroxymethyl)phenyl}-6-cyclopropyl-8-fluoroisoquinolin-1(2H)-one (Example 57)

2-{3-[2-amino-6-(1-benzyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one (Example 58)

2-(3-{2-amino-6-[6-(dimethylamino)pyridin-3-yl]-7H-pyrrolo[2,3-d]pyrimidin-4-yl}-2-(hydroxymethyl)phenyl)-6-cyclopropyl-8-fluoroisoquinolin-1(2H)-one (Example 59)

2-[3-(2-amino-6-{5-[(2-methoxyethyl)amino]pyridin-3-yl}-7H-pyrrolo[2,3-d]pyrimidin-4-yl)-2-(hydroxymethyl)phenyl}-6-cyclopropyl-8-fluoroisoquinolin-1(2H)-one (Example 60)

2-{3-[2-amino-6-(4-{[4-(2-hydroxyethyl)piperazin-1-yl]methyl}phenyl)-7H-pyrrolo[2,3-d]pyrimidin-4-yl]-2-(hydroxymethyl)phenyl}-6-cyclopropyl-8-fluoroisoquinolin-1(2H)-one (Example 61)

2-{3-[2-amino-6-(1-ethyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one (Example 62)

2-{3-[2-amino-6-(1-isopropyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one (Example 63)

2-{3-[2-amino-6-(1-phenyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one (Example 64)

2-{3-[2-amino-6-(6-methoxypyridin-3-yl)-7H-pyrrolo[2,3-d]pyrimidin-4-yl]-2-(hydroxymethyl)phenyl}-6-cyclopropyl-8-fluoroisoquinolin-1(2H)-one (Example 65)

2-[3-(2-amino-6-{4-[(3-oxopiperazin-1-yl)methyl]phenyl}-7H-pyrrolo[2,3-d]pyrimidin-4-yl)-2-(hydroxymethyl)phenyl}-6-cyclopropyl-8-fluoroisoquinolin-1(2H)-one (Example 66)

2-(3-{2-amino-6-[4-(thiazolidin-3-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one (Example 67)

tert-butyl 4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}-5,6-dihydropyridine-1(2H)-carboxylate (Example 68)

2-{3-[6-(1-acetyl-1,2,3,6-tetrahydropyridin-4-yl)-2-amino-7H-pyrrolo[2,3-d]pyrimidin-4-yl]-2-(hydroxymethyl)phenyl}-6-cyclopropyl-8-fluoroisoquinolin-1(2H)-one (Example 69)

2-(3-{2-amino-6-[1-(morpholine-4-carbonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 70)

2-(3-{2-amino-6-[1-(4-methylpiperazine-1-carbonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 71)

2-(3-{2-amino-6-[1-(tert-butyl)-1H-pyrazol-4-yl]-7H-pyrrolo[2,3-d]pyrimidin-4-yl}-2-(hydroxymethyl)phenyl)-6-cyclopropyl-8-fluoroisoquinolin-1(2H)-one (Example 72)

2-[3-(2-amino-6-{4-[(4-hydroxypiperidin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 73)

2-[3-(2-amino-6-{4-[(4-methoxypiperidin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 74)

2-{3-(6-{4-[(4-acetylpiperazin-1-yl)methyl]phenyl}-2-amino-7H-pyrrolo[2,3-d]pyrimidin-4-yl)-2-(hydroxymethyl)phenyl]-6-cyclopropyl-8-fluoroisoquinolin-1(2H)-one (Example 75)

2-[3-(2-amino-6-{4-[(2,6-dimethylmorpholino)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 76)

2-[3-(2-amino-6-{4-[(4,4-difluoropiperidin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 77)

2-{3-[2-amino-6-(1-methyl-1H-pyrazol-3-yl)-7H-pyrrolo[2,3-d]pyrimidin-4-yl]-2-(hydroxymethyl)phenyl}-6-cyclopropyl-8-fluoroisoquinolin-1(2H)-one (Example 78)

2-{3-[2-amino-6-(4-{[4-(2,2,2-trifluoroethyl)piperazin-1-yl]methyl}phenyl)-7H-pyrrolo[2,3-d]pyrimidin-4-yl]-2-(hydroxymethyl)phenyl}-6-cyclopropyl-8-fluoroisoquinolin-1(2H)-one (Example 79)

2-[3-(2-amino-6-{4-[(3,3-dimethylpiperidin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one (Example 80)

2-{3-[2-amino-6-(cyclohex-1-en-1-yl)-7H-pyrrolo[2,3-d]pyrimidin-4-yl]-2-(hydroxymethyl)phenyl}-6-cyclopropyl-8-fluoroisoquinolin-1(2H)-one (Example 81)

2-{3-[2-amino-6-(3,6-dihydro-2H-thiopyran-4-yl)-7H-pyrrolo[2,3-d]pyrimidin-4-yl]-2-(hydroxymethyl)phenyl}-6-cyclopropyl-8-fluoroisoquinolin-1(2H)-one (Example 82)

2-{3-[2-amino-6-(1,1-dioxido-3,6-dihydro-2H-thiopyran-4-yl)-7H-pyrrolo[2,3-d]pyrimidin-4-yl]-2-(hydroxymethyl)phenyl}-6-cyclopropyl-8-fluoroisoquinolin-1(2H)-one (Example 83)

2-{3-[2-amino-6-(1-propionyl-1,2,3,6-tetrahydropyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 84)

2-[3-(2-amino-6-{1-[2-(dimethylamino)acetyl]-1,2,3,6-tetrahydropyridin-4-yl}-7H-pyrrolo[2,3-d]pyrimidin-4-yl)-2-(hydroxymethyl)phenyl]-6-cyclopropyl-8-fluoroisoquinolin-1(2H)-one (Example 85)

2-(3-{2-amino-6-[1-(2-morpholinoacetyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 86)

4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}-N,N-dimethyl-5,6-dihydropyridine-1(2H)-carboxamide (Example 87)

2-(3-{2-amino-6-[1-(pyrrolidine-1-carbonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 88)

2-(3-{2-amino-6-[1-(methylsulfonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 89)

2-(3-{2-amino-6-[1-(isopropylsulfonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 90)

2-{3-[2-amino-6-(1-ethyl-1,2,3,6-tetrahydropyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 91)

2-(3-{2-amino-6-[1-(cyclopropylmethyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one (Example 92)

2-{3-[2-amino-6-(1,2,3,6-tetrahydropyridin-4-yl)-7H-pyrrolo[2,3-d]pyrimidin-4-yl]-2-(hydroxymethyl)phenyl}-6-cyclopropyl-8-fluoroisoquinolin-1(2H)-one (Example 93)

Effect of the Invention

The present inventors have intensively studied so as to solve the above problems and found that an oxoisoquinoline derivative of the formula (I) described before or a pharmaceutically acceptable salt thereof has an excellent BTK inhibitory activity, and further confirmed a potent anti-tumor effect when said oxoisoquinoline derivative or a pharmaceutically acceptable salt thereof was orally administered to a cancer mouse model using OCI-Ly10 strain to complete the present invention.

The present invention provides with a compound which is useful for preventing or treating diseases which are known to be involved in abnormal cell response through BTK, for example, self-immune diseases, inflammatory diseases, bone diseases, and cancers such as lymphoma, and a pharmaceutical composition comprising said compound as an active ingredient is preferably used, especially when orally administered.

The compound provided by the present invention is also useful, as a BTK inhibitor, for reagents to be used in tests and researches.

BEST MODE TO CARRY OUT THE INVENTION

The present invention is explained below in detail.

A novel oxoisoquinoline derivative of the present invention is a compound of the formula (I):

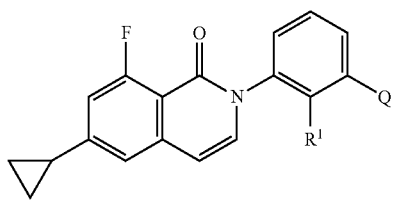
(I)

wherein $R^1$ is an optionally substituted lower alkyl group, and

Q is a structure selected from (a), (b) and (c) below:

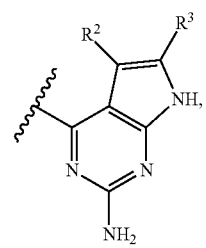
(a)

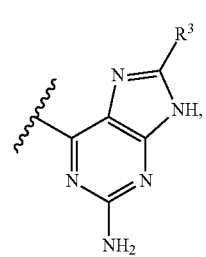
(b)

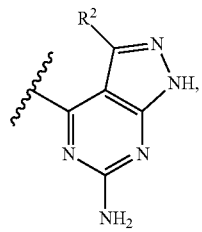
(c)

$R^2$ and $R^3$ are independently a hydrogen atom, an optionally substituted lower alkyl group, an optionally substituted cycloalkyl group, an optionally substituted aryl group, an optionally substituted heteroaryl group and an optionally substituted heterocyclic group.

The structure (a) is preferable as a structure of Q.

In the specification of the present application, a moiety of the lower alkyl group in the "optionally substituted lower alkyl group" may be any of a linear, or branched alkyl group having one to three carbon atoms, and specifically a methyl group, an ethyl group, and an isopropyl group etc. may be exemplified.

A moiety of the cycloalkyl group in the "optionally substituted cycloalkyl group" may be any of cyclic alkyl group having three to six carbon atoms, and specifically a cyclopropyl group, a cyclobutyl group, cyclohexyl group etc. may be exemplified.

A moiety of the aryl group in the "optionally substituted aryl group" may be any of monocyclic or bicyclic aryl group having 6 to 14 carbon atoms, and the bicyclic aryl group may be partially hydrogenated. Specifically, a phenyl group, a naphthyl group, a tetrahydronaphthyl group, an indenyl group etc. may be exemplified.

A moiety of the heteroaryl group in the "optionally substituted heteroaryl group" include a monocyclic aromatic heterocyclic group and a fused aromatic heterocyclic group, and 5- or 6-membered monocyclic aromatic heterocyclic group containing one heteroatom at least selected from a nitrogen atom, a sulfur atom and an oxygen atom as the monocyclic aromatic heterocyclic group. Specifically, pyrrolyl, imidazolyl, pyrazolyl, thienyl, thiazolyl, furanyl, pyridyl, pyrimidyl, pyridazinyl etc. may be exemplified, and examples of the fused aromatic heterocyclic group include a fused bicyclic heterocyclic group in which 3- to 8-membered ring is fused containing one heteroatom at least selected from a nitrogen atom, a sulfur atom and an oxygen atom. Specifically tetrahydroisoquinolyl, benzothiophenyl, benzimidazolyl, benzooxazolyl, benzothiazolyl, indolyl, and isoquinolyl may be exemplified.

A moiety of the heterocyclic group in the "optionally substituted heterocyclic group" is a 4- to 6-membered monocyclic saturated heterocyclic group containing one heteroatom at least selected from a nitrogen atom, a sulfur atom and an oxygen atom and may include an unsaturated bond partially in the ring. Specifically, a dihydrothiopyranyl group, 1,1-dioxo-dihydrothiopyranyl group, and tetrahydropyridyl group may be exemplified, and the tetrahydropyridyl group is especially preferably exemplified.

A substituent of the term of "optionally substituted" in the optionally substituted lower alkyl group, the optionally substituted cycloalkyl group, the optionally substituted aryl group, the optionally substituted heteroaryl group, and the optionally substituted heterocyclic group may be the same or different when the above group have two or more substituents, and the group may be substituted with one, or two or more of any kind of substituent(s) at any position which is chemically allowable.

Examples of the substituent in the optionally substituted lower alkyl group include for example, a halogen atom, a C1-C4 alkyl group, an amino group optionally substituted with one or two C1-C4 alkyl group, a nitro group, a cyano group, a hydroxy group, a carbamoyl group optionally substituted with one or two C1-C4 alkyl group, a carboxyl group, a formyl group, an acetyl group, a mesyl group, a benzoyl group, a C1-C6 acylamino group, a C1-C6 acyloxy group etc. As the optionally substituted lower alkyl group, a hydroxymethyl group may be exemplified.

Examples of a substituent related to the term of "optionally substituted" in the optionally substituted cycloalkyl group, the optionally substituted aryl group, the optionally substituted heteroaryl group and the optionally substituted heterocyclic group include a halogen atom, an oxygen atom, a C1-C4 alkyl group, a C1-C4 alkoxy group, an amino group optionally substituted with one or two C1-C4 alkyl group, a nitro group, a cyano group, a hydroxy group, a carbamoyl group optionally substituted with one or two C1-C4 alkyl group, a sulfonyl group optionally substituted with a C1-C4 alkyl group, a carboxy group, a formyl group, an acetyl group, a mesyl group, a benzoyl group, an oxetanyl group, a C1-C6 acylamino group, and a C1-C6 acyloxy group etc. . . .

Isomers may exist in the compound (I) of the present invention, depending on the kind of the substituent. In the present specification, the isomers may be described by a chemical structure of only one form thereof, but the present invention includes all isomers (geometrical isomer, optical isomer, tautomer, etc.) which can be structurally formed, and also includes isomers alone, or a mixture thereof.

Examples of a pharmaceutically acceptable salt of the compound (I) of the present invention include inorganic acid salts with hydrochloric acid, sulfuric acid, carbonic acid, and phosphoric acid etc.; and organic acid salts with fumaric acid, maleic acid, methanesulfonic acid, and p-toluenesulfonic acid etc. . . . The present invention also includes ammonium salts, in addition to alkali metal salts with sodium and potassium; alkaline earth metal salts with magnesium and calcium; organic amine salts with triethylamine and ethanolamine; and basic amino acid salts with lysine, arginine, and ornithine etc. . . .

Unless indicated otherwise, 'the compound (I) of the present invention' also includes its prodrug.

The compound (I) and a pharmaceutically acceptable salt thereof in the present invention can be produced, for example, by methods shown below. When a defined group may be chemically affected under the conditions of an exemplified method in the production method shown below, or is unsuited for use to carry out the method, it is possible to easily produce them by a method which is usually used in organic synthetic chemistry, for example, a method of applying means such as protection or deprotection of a functional group [T. W. Greene, Protective Groups in Organic Synthesis 3rd Edition, John Wiley & Sons, Inc., 1999]. If necessary, the order of a reaction step such as introduction of substituents can also be changed.

Meanings of abbreviations and symbols used in the following description are as follows.
DCM: dichloromethane
THF: tetrahydrofuran
DIEA: N,N-diisopropylethylamine
DMF: N,N-dimethylformamide
DMSO: dimethyl sulfoxide
Pd(PPh$_3$)$_4$: tetrakis[triphenylphosphine[Palladium(0)
[Method for Preparation of Compound (I) of the Present Invention]

A compound (I) of the present invention can be prepared according to scheme 1 for example;

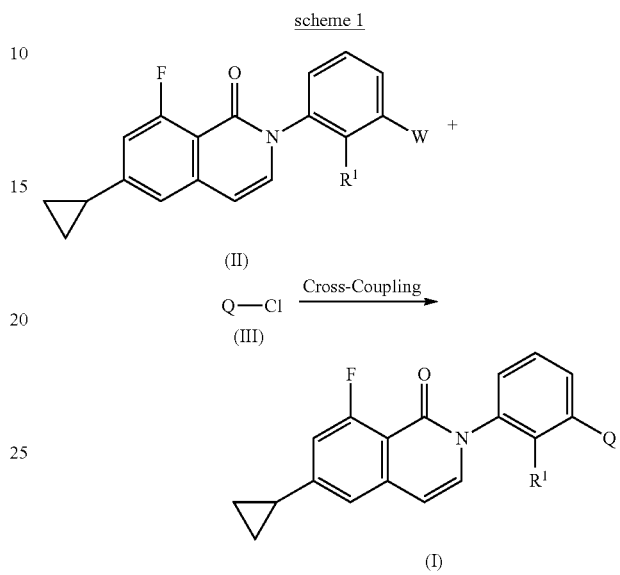

wherein W is a boronyl group or boronate ester group, and R$^1$ and Q are the same as before.

The compound (I) of the present invention can be produced by a cross-coupling reaction such as Suzuki coupling reaction, using a compound (II) and a compound (III) (with respect to the conditions of the Suzuki coupling reaction, see literatures, for example, N. Miyaura et al., J. Am. Chem. Soc., 107, 972 (1985), N. Miyaura, A. Suzuki, Chem. Rev. 95, 2457 (1995)). That is, the reaction can be carried out under the presence of a metal catalyst such as palladium or nickel, if necessary, using a base and additives.

Examples of a solvent used in the reaction include THF, dioxane, toluene, dimethoxyethane, methanol, ethanol, and acetonitrile. It is also suitable to use two or more kinds of these solvents, or to use them in combination with water. The solvent is preferably a mixed solvent of THF and water, or a mixed solvent of toluene, methanol and water, or dioxane.

The compound (II) is preferably used in an equivalent or excess amount, and more preferably in an amount of from 1 equivalent to 5 equivalents, based on the compound (III). If necessary, a base may be added so as to accelerate the reaction, and sodium carbonate, cesium carbonate, and potassium carbonate are usually used as the base. The amount of the base to be used is from 1 equivalent to 10 equivalents, and preferably from 1 equivalent to 5 equivalents, based on the compound (III). It is possible to use, as a metal catalyst, a commercially available palladium catalyst (for example, PdCl$_2$(dppf), Pd$_2$(dba)$_3$, Pd(PPh$_3$)$_4$, etc.) which is used in the cross-coupling, and the catalyst is preferably used in a catalytic amount, that is, an amount of from 0.1 equivalent to 0.5 equivalent based on the compound (III).

If necessary, additives can be added so as to accelerate the reaction. The additive includes, for example, rac-BINAP and can be used in the amount of from 0.01 equivalent to 1 equivalent based on the compound (III). It is possible to synthesize the product by reacting at a temperature ranging from 0° C. to 200° C. for several minutes to several days, and preferably from 10° C. to 100° C. for 1 hour to 36 hours. It is also possible to synthesize the product by reacting under the temperature condition of from 60° C. to 150° C. for several minutes to several hours, using a microwave synthesis equipment.

Also the compound (I) of the present invention can be prepared by protecting functional groups of the compound (II) and (III), if necessary, using a common technique which is used in a synthetic organic chemistry, and deprotecting them after the coupling reaction.

Further the compound (II) used in the scheme 1 as a starting material is available according to a method described in Patent Document 2.

The compound (III-a) in which Q is a structure (a) is one of the compound (III) used as a starting material in scheme 1, and can be prepared according scheme 2 for example;

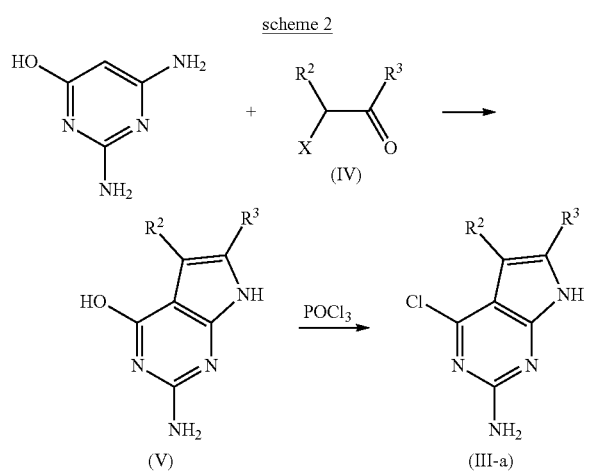

wherein X is a halogen atom and $R^2$ and $R^3$ are the same as before.

The compound (III-a) is obtained by cyclocondensation of 2,4-diamino-6-hydroxypyrimidine and the compound (IV) and a subsequent chlorination reaction by phosphorus oxychloride. That is, the compound (V) is obtained by reacting 1 to 5 equivalent, preferably 1 to 1.5 equivalent of the compound (IV) with 2,4-diamino-6-hydroxypyrimidine in a polar solvent and, if necessary, under the presence of a base catalyst.

Any solvent may be used without limitation if the reaction is not disturbed, but water and DMF are preferably used. The reaction temperature is usually from 0° C. to 200° C., preferably from room temperature to 150° C. The reaction time is not limited, but usually from 0.2 to 48 hours are exemplified, and preferably from 1 to 24 hours are exemplified.

The compound (III-a) is obtained by reacting 1 to 50 equivalent, preferably 5 to 20 equivalent of phosphorus oxychloride with the compound (V). The reaction temperature is usually from room temperature to 200° C., preferably from 50° C. to 150° C. The reaction time is not limited, but usually from 1 to 48 hours are exemplified, and preferably from 5 to 24 hours are exemplified.

One of the starting materials in scheme 2, 2,4-diamino-6-hydroxypyrimidine is commercially available, and the compound (IV) is also commercially available or prepared by a well-known procedure or the procedure according to it.

The compound (III-b) in which Q is a structure (b) is one of the compound (III) used as a starting material in scheme 1, and can be prepared according scheme 3 for example;

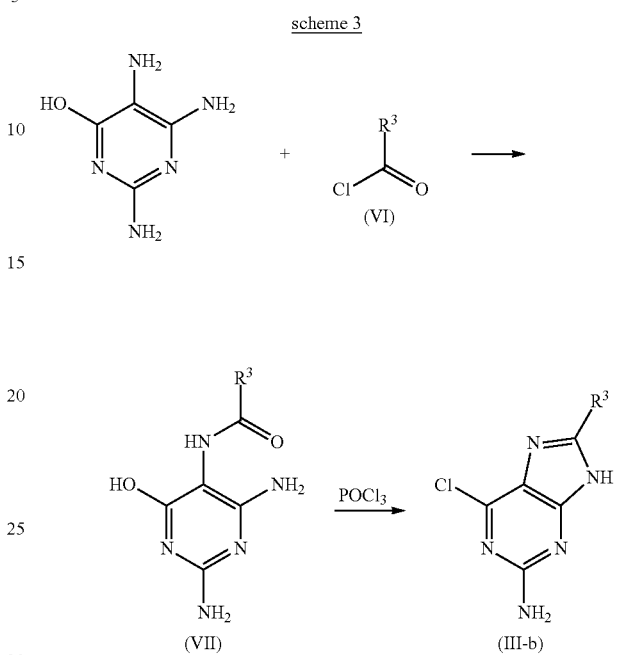

wherein $R^3$ is the same as before.

The compound (III-b) is obtained by the condensation of 2,5,6-triaminopyrimidin-4(3H)-one and the acid chloride (VI), and a subsequent dehydrocyclization and chlorination reaction by phosphorus oxychloride. That is, the compound (VII) is obtained by reacting 1-10 equivalent, preferably 1-3 equivalent of the acid chloride (VI) with 2,5,6-triaminopyrimidin-4(3H)-one in a solvent under the presence of a base.

Usually an organic base such as DIEA, triethylamine etc. or an inorganic base such as sodium hydroxide or potassium carbonate etc. is used, and 1 to 10 equivalent, preferably 1 to 5 equivalent of the base is added based on the acid chloride (VI). Any solvent may be used without limitation if the reaction is not disturbed, but water, DMF and THF are preferably used. The reaction temperature is usually from −20° C. to 100° C., preferably from 0° C. to 80° C. The reaction time is not limited, but usually from 0.2 to 48 hours are exemplified, and preferably from 1 to 24 hours are exemplified.

The compound (III-b) is obtained by reacting 1 to 100 equivalent, preferably 10 to 50 equivalent of phosphorus oxychloride with the compound (VII). The reaction temperature is usually from room temperature to 200° C., preferably from 50° C. to 150° C. The reaction time is not limited, but usually from 1 to 48 hours are exemplified, and preferably from 5 to 24 hours are exemplified.

One of the starting materials in scheme 3, 2,5,6-triaminopyrimidin-4(3H)-one is commercially available, and the compound (VI) is also commercially available or prepared by a well-known procedure or the procedure according to it.

The compound (III-c) in which Q is a structure (c) is one of the compound (III) used as a starting material in scheme 1, and can be prepared according scheme 4 for example;

scheme 4

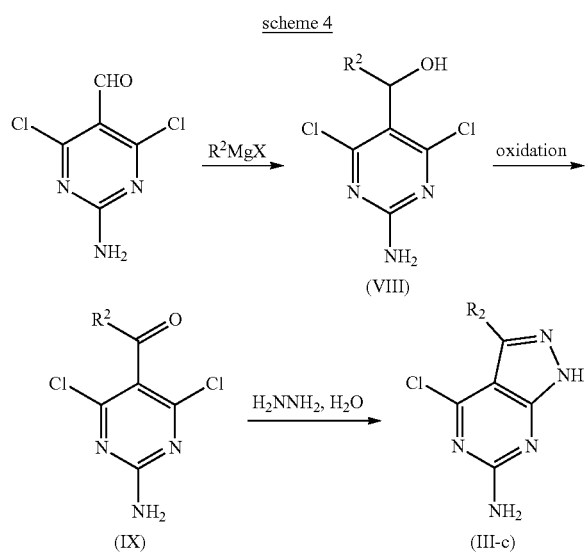

wherein R² and X are the same as before.

The compound (III-c) is obtained by the condensation of 2-amino-4,6-dichloropyrimidin-5-carbaldehyde and R²MgX, and a subsequent oxidation and cyclization reaction by hydrazine monohydrate. That is, the compound (VIII) is obtained by reacting 1-10 equivalent, preferably 1-5 equivalent of R²MgX with 2-amino-4,6-dichloropyrimidin-5-carbaldehyde in a solvent.

Any solvent may be used without limitation if the reaction is not disturbed, but THF is preferably used. The reaction temperature is usually from −100° C. to −30° C., preferably from −80° C. to −60° C. The reaction time is not limited, but usually from 0.1 to 12 hours are exemplified, and preferably from 0.2 to 6 hours are exemplified.

The compound (IX) is obtained by oxidizing the compound (VIII) with 1 to 50 equivalent, preferably 2 to 20 equivalent of an oxidizing agent, and a metallic oxidizing agent such as chromic oxide(VI) and manganese dioxide etc. or a hypervalent iodine oxidizing agent such as Dess-Martin Periodinane etc. Any solvent may be used without limitation if the reaction is not disturbed, but acetone, DCM and 1,2-dichloroethane are preferably used. The reaction temperature is usually from −20° C. to 100° C., preferably from 0° C. to 80° C. The reaction time is not limited, but usually from 0.2 to 24 hours are exemplified, and preferably from 1 to 12 hours are exemplified.

The compound (III-c) is obtained by reacting 1-10 equivalent, preferably 1-5 equivalent of hydrazine monohydrate with the compound (IX) in a solvent and if necessary, under the presence of a base catalyst. Any solvent may be used without limitation if the reaction is not disturbed, but 1,4-dioxane or THF is preferably used. The reaction temperature is usually from 0° C. to 100° C., preferably from room temperature to 60° C. The reaction time is not limited, but usually from 0.2 to 48 hours are exemplified, and preferably from 0.5 to 24 hours are exemplified.

2-Amino-4,6-dichloropyrimidin-5-carbaldehyde, which is a starting material in scheme 4, is commercially available, and R²MgX is also commercially available or prepared by a well-known procedure or the procedure according to it.

The compound (III-a') in which Q is a structure (a) and R² is a hydrogen atom is one of the compound (III) used as a starting material in scheme 1, and can be prepared according scheme 5 for example;

scheme 5

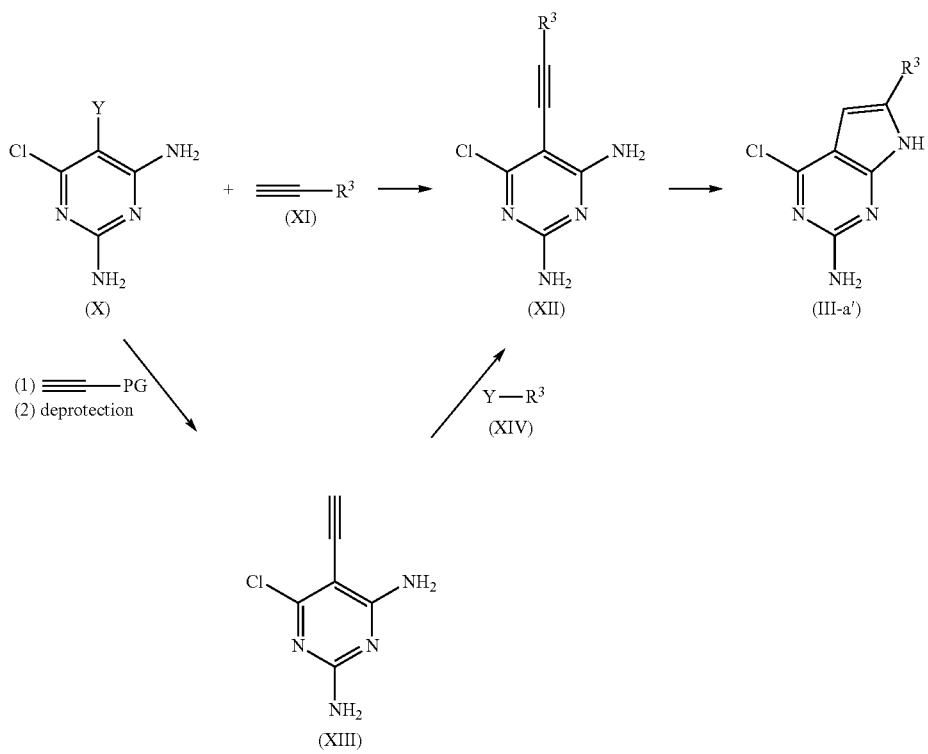

wherein PG is a protecting group, Y is a bromine atom, an iodine atom or a trifluoromethanesulfonyl group and $R^3$ is the same as before.

The compound (III-a') is obtained by a cyclization reaction of the compound (XII), which is obtained by Sonogashira coupling reaction between diaminopyrimidine (X) and the compound (XI). Specifically, the compound (XII) is obtained by reacting 1-10 equivalent, preferably 2-5 equivalent of the compound (XI) with diaminopyrimidine (X) in a polar solvent under the presence of copper iodide, a palladium catalyst and a base, and subsequent treatment with an aqueous solution of sodium hydroxide and tetrabutylammonium fluoride.

An amount of copper iodide added in the reaction is 0.01-2 equivalent preferably 0.05-0.5 equivalent based on the diaminopyrimidine (X), and a palladium(0) catalyst such as $Pd(PPh_3)_4$ and $PDCl_2(PPh_3)_2$ etc. is used as the palladium catalyst. An amount of the palladium catalyst added in the reaction is 0.01-2 equivalent, preferably 0.05-0.5 equivalent based on the diaminopyrimidine (X). An organic base such as DIEA and triethylamine is usually used in the reaction as the base, and 1-10 equivalent, preferably 1-5 equivalent of the base is added in the reaction based on the diaminopyrimidine (X). Any solvent may be used without limitation if the reaction is not disturbed, but 1,4-dioxane or DMF is preferably used. The reaction temperature is usually from 0° C. to 200° C., preferably from room temperature to 80° C. The reaction time is not limited, but usually from 0.2 to 5 hours are exemplified, and preferably from 0.5 to 2 hours are exemplified.

The compound (III-a') is obtained by adding 1-50 equivalent, preferably 2-20 equivalent of the base to the compound (XII) and conducting a cyclization reaction. Potassium tert-butoxide or cesium carbonate can be used as the base. Any solvent may be used without limitation if the reaction is not disturbed, but N-methylpyrrolidone, 1,4-dioxane and DMF are preferably used. The reaction temperature is usually from −20° C. to 100° C., preferably from oC to 80° C. The reaction time is not limited, but usually from 0.2 to 10 hours are exemplified, and preferably from 0.5 to 2 hours are exemplified.

Also the compound (XII) of scheme 5 can be synthesized by introducing the $R^3$ moiety through Sonogashira coupling with the compound (XIV) to the compound (XIII), which is obtained by Sonogashira coupling between diaminopyridine (X) and terminal-protected acetylene, and a subsequent deprotection. That is, the compound (XIII) is obtained by reacting 1-10 equivalent, preferably 2-5 equivalent of the terminal-protected acetylene such as trimethylsilylacetylene with diaminopyrimidine (X) in a polar solvent under the presence of cuprous iodide, a palladium catalyst and a base, and subsequently treating it with an aqueous solution of sodium hydroxide and tetra-n-butylammonium fluoride.

An amount of copper iodide added in the reaction is 0.01-2 equivalent, preferably 0.05-0.5 equivalent based on the diaminopyrimidine (X), and a palladium(0) catalyst such as $Pd(PPh_3)_4$ and $PDCl_2(PPh_3)_2$ etc. is used as the palladium catalyst. An amount of the palladium catalyst added in the reaction is 0.01-2 equivalent, preferably 0.05-0.5 equivalent based on the diaminopyrimidine (X). An organic base such as DIEA and triethylamine is usually used in the reaction as the base, and 1-10 equivalent, preferably 1-5 equivalent of the base is added in the reaction based on the diaminopyrimidine (X). Any solvent may be used without limitation if the reaction is not disturbed, but 1,4-dioxane or DMF is preferably used. The reaction temperature is usually from 0° C. to 200° C., preferably from room temperature to 80° C. The reaction time is not limited, but usually from 0.2 to 5 hours are exemplified, and preferably from 0.5 to 2 hours are exemplified.

The compound (XII) is obtained by reacting 1-10 equivalent, preferably 1-5 equivalent of the compound (XIV) with the compound (XIII) in a polar solvent under the presence of copper iodide, a palladium catalyst and a base. An amount of copper iodide added in the reaction is 0.01-2 equivalent, preferably 0.05-0.5 equivalent based on the compound (XIII), and a palladium(0) catalyst such as $Pd(PPh_3)_4$ and $PdCl_2(PPh_3)_2$ etc. is used as the palladium catalyst. An amount of the palladium catalyst added in the reaction is 0.01-2 equivalent, preferably 0.05-0.5 equivalent based on the diaminopyrimidine (XIII). An organic base such as DIEA and triethylamine is usually used in the reaction as the base, and 1-10 equivalent, preferably 1-5 equivalent of the base is added in the reaction based on the compound (XIII). Any solvent may be used without limitation if the reaction is not disturbed, but 1,4-dioxane or DMF is preferably used. The reaction temperature is usually from 0° C. to 200° C., preferably from room temperature to 120° C. The reaction time is not limited, but usually from 0.2 to 5 hours are exemplified, and preferably from 0.5 to 2 hours are exemplified.

Diaminopyrimidine (X) of the starting material in scheme 5, the terminal-protected acetylene (XI) and the compound (XIV) are also commercially available or prepared by a well-known procedure or the procedure according to it.

In the scheme above, W is a boronyl group and a salt of alkalimetal or alkaliearth metal is usable. Examples of a boronate ester group include a boronate dimethyl ester group, a boronate diethyl ester group, a boronate dibutyl ester group, a boronate dicyclohexyl group, a boronate ethylene glycol ester group, a boronate propylene glycol ester group(a boronate 1,2-propanediol ester group, a boronate 1,3-propaediolester group), a boronate neopentyl glycol ester group, a boronate catechol ester group, a boronate glycerin ester group, a boronate trimethyrol ethane ester group, a boronate diethanolamine ester group, a boronate triethanolamine ester etc., and a boronic acid anhydride.

It is possible to obtain the compound (I) having the desired functional group at the desired position of the present invention by appropriately using the above methods in combination, and then carrying out a method usually used in organic synthetic chemistry (for example, an alkylation reaction of an amino group, an oxidizing reaction of alkylthio group into a sulfoxide group or a sulfone group, a reaction of converting an alkoxy group into a hydroxyl group, or a reaction of inversely converting the group).

The compound (I) or a pharmaceutically acceptable salt thereof of the present invention can be formulated into a conventional pharmaceutical formulation (pharmaceutical composition), which is suited for oral administration, parenteral administration, or local administration.

Formulations for oral administration include solid formulations such as tablets, granules, powders, and capsules; and liquid formulations such as syrups. These formulations can be prepared by a conventional method. The solid formulations can be prepared by using conventional pharmaceutical carriers, for example, lactose; starches such as corn starch; crystalline celluloses such as microcrystalline cellulose; and hydroxypropyl cellulose, calcium carboxymethyl cellulose, talc, and magnesium stearate. Capsules can be prepared by encapsulating thus prepared granules or powders. Syrups can be prepared by dissolving or suspending the compound (I) or a pharmaceutically acceptable salt thereof of the present invention in an aqueous solution containing sucrose and carboxymethyl cellulose.

Formulations for parenteral administration include injections such as installation. Injection formulations can also be prepared by a conventional method, and can be appropriately incorporated into isotonic agents (for example, mannitol, sodium chloride, glucose, sorbitol, glycerol, xylitol, fructose, maltose, mannose), stabilizers (for example, sodium sulfite, albumin), and antiseptics (for example, benzyl alcohol, methyl p-oxybenzoate).

The dosage of the compound (I) or a pharmaceutically acceptable salt thereof of the present invention can vary depending on severity of disease, age and body weight of the patient, and dosage form, and is usually within a range from 1 mg to 1,000 mg per day for adults. The compound or a pharmaceutically acceptable salt thereof can be administered once a day, or dividedly administered twice or three times a day according to an oral or parenteral route.

The compound (I) or a pharmaceutically acceptable salt thereof of the present invention can also be used, as a BTK inhibitor, for reagents to be used in experimental tests and/or researches.

EXAMPLES

The present invention will be more specifically described below by way of Examples and Test Examples, but the present invention is not limited to these Examples.

Identification of the compound was carried out by hydrogen nuclear magnetic resonance spectrum ($^1$H-NMR) and mass spectrum (MS). $^1$H-NMR is measured at 400 MHz or 500 MHz, unless otherwise specified, and exchangeable hydrogen cannot be sometimes clearly observed depending on the compound and measurement conditions. In addition, br. means a broad signal (broad).

HPLC preparative chromatography was carried out by a commercially available ODS column in a gradient mode using water/methanol (containing formic acid) or water/acetonitrile (containing ammonium hydrogen carbonate) as eluents, unless otherwise specified.

Example 1

2-[3-(2-amino-6-phenyl-7H-pyrrolo[2,3-d]pyrimidin-4-yl)-2-(hydroxymethyl)phenyl]-6-cyclopropyl-8-fluoroisoquinolin-1(2H)-one

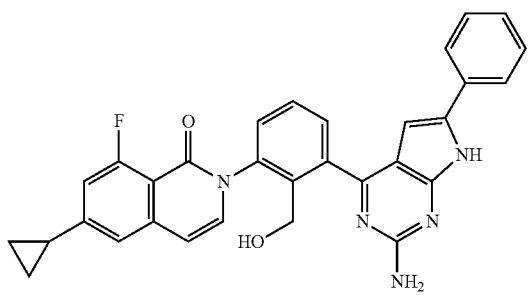 [SMILES: Nc1nc(-c2cccc(-n3ccc4cc(C5CC5)cc(F)c4c3=O)c2CO)c2cc(-c3ccccc3)[nH]c2n1]

(The First Step)

A sodium acetate (0.65 g, 7.93 mmol) was added to an aqueous solution (20 ml) of 2,4-diamino-6-hydroxypyrimidine (1.0 g, 7.93 mmol), and the mixture was stirred at 100° C. for an hour. 2-Bromo-acetophenone (1.89 g, 9.51 mmol) was added and the mixture was stirred at 100° C. for 8 hours. The precipitated solid was collected to give 2-amino-6-phenyl-7H-pyrrolo[2,3-d]-pyrimidin-4-ol (1.5 g) as a crude product.

LCMS (m/z): 227.11 [M+H]$^-$.

(The Second Step)

A mixture of 2-amino-6-phenyl-7H-pyrrolo[2,3-d]-pyrimidin-4-ol (1.5 g, 6.64 mmol) and pivalic acid anhydride (5 ml) was stirred at 190° C. for 5 hours. n-Pentane was added to the reaction mixture and stirred at room temperature for half an hour. The precipitated solid was collected by filtration to give N-(4-hydroxy-6-phenyl-7H-pyrrolo[2,3-d]pyrimidin-2-yl)pivalamide (1.4 g).

LCMS (m/z): 311.33 [M+H]$^-$.

(The Third Step)

A mixture of N-(4-hydroxy-6-phenyl-7H-pyrrolo[2,3-d]pyrimidin-2-yl)pivalamide (1.4 g, 4.52 mmol) and phosphorus oxychloride (5 ml) was stirred at 100° C. for 10 hours. Excess phosphorus oxychloride was evaporated under reduced pressure, a saturated aqueous solution of sodium bicarbonate was added to the residue, and extracted with ethyl acetate. The obtained organic layer was washed with water and saturated brine, and dried over anhydrous sodium sulfate. The solvent was evaporated under reduced pressure and the obtained residue was purified with a column chromatography (silicagel, petroleum ether/ethyl acetate) to give N-(4-chloro-6-phenyl-7H-pyrrolo[2,3-d]pyrimidin-2-yl) pivalamide (0.4 g).

$^1$H NMR (500 MHz, DMSO-d$_6$) δ=12.93 (s, 1H), 10.06 (s, 1H), 7.99-7.97 (m, 2H), 7.53-7.47 (m, 2H), 7.41-7.38 (m, 1H), 7.04 (d, J=2.0 Hz, 1H), 1.25 (s, 9H);

LCMS (m/z): 329.26 [M+H]$^-$.

(The Fourth Step)

A mixed solvent of DME-water (5:1, 12 ml) was added to 2-(6-cyclopropyl-8-fluoro-1-oxoisoquinolin-2(1H)-yl)-6-(4,4,5,5-tetramethyl-1,3,2-dioxaboran-2-yl)benzyl acetate (0.392 g, 0.82 mmol), N-(4-chloro-6-phenyl-7H-pyrrolo[2,3-d]pyrimidin-2-yl)pivalamide (0.27 g, 0.82 mmol) and potassium carbonate (0.227 g, 1.65 mmol), and the mixture was degassed for 30 minutes under argon gas atmosphere. Pd(PPh$_3$)$_4$ (95 mg, 0.08 mmol) was added thereto and reacted in a microwave reaction apparatus at 100° C. for 10 minutes. The reaction mixture was filtered through celite, water was added to the filtrate and the product was extracted with ethyl acetate. The obtained organic layer was washed with water and saturated brine successively, and dried over anhydrous sodium sulfate. The solvent was evaporated under reduced pressure to give 2-(6-cyclopropyl-8-fluoro-1-oxoisoquinolin-2(1H)-yl)-6-(6-phenyl-2-pivalamide-7H-pyrrolo[2,3-d]pyrimidin-4-yl)benzyl acetate as a crude product. The obtained crude product was dissolved in methanol (2 ml), a 5% aqueous solution of sodium hydroxide was added and the mixture was stirred at 70° C. for 30 minutes. The solvent was evaporated under reduced pressure and the obtained residue was purified with preparative HPLC to give the titled compound (35 mg).

$^1$H NMR (400 MHz, DMSO-d$_6$) δ 11.89 (s, 1H), 7.91-7.83 (m, 2H), 7.80 (dd, J=7.7, 1.3 Hz, 1H), 7.62 (t, J=7.8 Hz, 1H), 7.52-7.33 (m, 4H), 7.34-7.25 (m, 2H), 7.00 (dd, J=13.3, 1.7 Hz, 1H), 6.76 (s, 1H), 6.63 (dd, J=7.5, 2.1 Hz, 1H), 6.42 (s, 2H), 5.18 (s, 1H), 4.33-4.25 (m, 1H), 4.12-4.04 (m, 1H), 2.14-2.02 (m, 1H), 1.15-1.01 (m, 2H), 0.96-0.81 (m, 2H);

LCMS (m/z): 518.42 [M+H]$^-$.

Example 2

2-[3-(2-amino-8-phenyl-9H-purin-6-yl)-2-(hydroxymethyl)phenyl]-6-cyclopropyl-8-fluoroisoquinolin-1(2H)-one

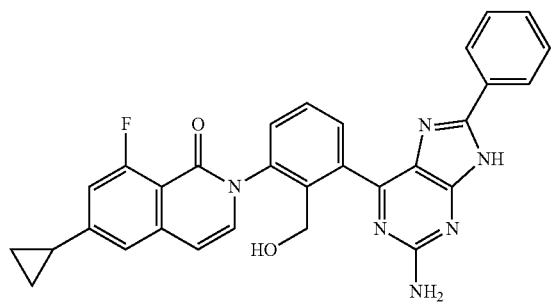 [SMILES: Nc1nc(-c2cccc(-n3ccc4cc(C5CC5)cc(F)c4c3=O)c2CO)c2nc(-c3ccccc3)[nH]c2n1]

(The First Step)

2,5,6-triaminopyrimidin-4(3H)-one (1 g, 7.092 mmol) and benzoyl chloride (1.63 ml, 14.18 mmol) were added to a 2N aqueous solution of sodium hydroxide (25 ml) under ice-cooling, and the mixture was stirred for an hour. Acetic acid was added to the reaction mixture to adjust its acidity to pH 5, and the precipitated solid was collected by filtration to give N-(2,4-diamino-6-hydroxypyrimidin-5-yl)benzamide (1.7 g).

$^1$H NMR (400 MHz, DMSO-$d_6$) δ 10.07 (s, 1H), 8.74 (s, 1H), 7.96-7.92 (m, 2H), 7.53-7.43 (m, 3H), 6.18 (br. s, 2H), 5.79 (br. s, 2H);

LCMS (m/z): 246.08 [M+H]$^-$.

(The Second Step)

A mixture of N-(2,4-diamino-6-hydroxypyrimidin-5-yl) benzamide (2.5 g, 10.2 mmol) and phosphorus oxychloride (50 ml) was stirred under reflux for 24 hours. Excess amount of phosphorus oxychloride was evaporated under reduced pressure, the obtained residue was made alkaline by the addition of an aqueous ammonia and the product was extracted with 10% MeOH-DCM. The obtained organic layer was washed with water and saturated brine, and dried over anhydrous sodium sulfate. The solvent was evaporated under reduced pressure, and the residue was purified with a column chromatography (silicagel, DCM/Methanol) to give 6-chloro-8-phenyl-9H-purin-2-amine (0.25 g)

LCMS (m/z): 245.87 [M+H]$^+$.

(The Third Step)

A mixed solvent of DME-water (3:1, 13 ml) was added to 2-(6-cyclopropyl-8-fluoro-1-oxoisoquinolin-2(1H)-yl)-6-(4,4,5,5-tetramethyl-1,3,2-dioxaboran-2-yl)benzyl acetate (0.25 g, 0.52 mmol), 6-chloro-8-phenyl-9H-purin-2-amine (0.128 g, 0.524 mmol) and potassium carbonate (0.216 g, 1.57 mmol) and the mixture was degassed under argon atmosphere for 30 minutes. Pd(PPh$_3$)$_4$ (60 mg, 0.05 mmol) was added and reacted in a microwave apparatus at 110° C. for 30 minutes. The reaction mixture was diluted with ethyl acetate, washed with water and saturated brine successively, and dried over anhydrous sodium sulfate. The solvent was evaporated under reduced pressure and the obtained residue was purified with preparative HPLC to give the titled compound (12 mg).

$^1$H NMR (500 MHz, DMSO-$d_6$) δ 13.30 (s, 1H), 8.07 (d, J=6.7 Hz, 2H), 7.91 (d, J=7.0 Hz, 1H), 7.63 (t, J=7.8 Hz, 1H), 7.54-7.48 (m, 4H), 7.41 (d, J=7.3 Hz, 1H), 7.28 (d, J=1.2 Hz, 1H), 7.00 (d, J=13.1 Hz, 1H), 6.68 (br. s, 2H), 6.63 (dd, J=1.5, 7.3 Hz, 1H), 5.49 (br. s, 1H), 4.36 (d, J=9.5 Hz, 1H), 4.13-4.09 (m, 1H), 2.10-2.05 (m, 1H), 1.12-1.08 (m, 2H), 0.89-0.86 (m, 2H);

LCMS (m/z): 519.39 [M+H].

Example 3

2-[3-(6-amino-3-phenyl-1H-pyrazolo[3,4-d]pyrimidin-4-yl)-2-(hydroxymethyl)phenyl]-6-cyclopropyl-8-fluoroisoquinolin-1(2H)-one

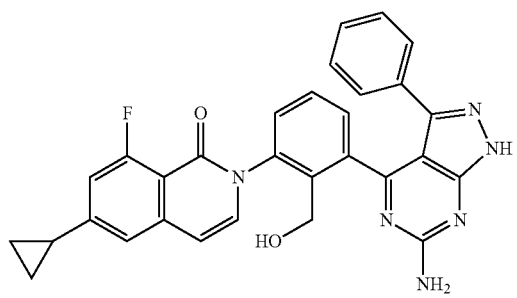

(The First Step)

Phenyl magnesium bromide (1M THF solution, 26 ml, 26 mmol) was added slowly to a THF solution (100 ml) of 2-amino-4,6-dichloropyrimidin-5-carbaldehyde (1.0 g, 5.2 mmol) at −78° C., and stirred for 2 hours. A saturated aqueous solution of ammonium chloride was added to the reaction mixture, filtered through celite, and the filtrate was extracted with 10% MeOH-DCM. The obtained organic layer was washed with water and saturated brine and dried over anhydrous sodium sulfate. The solvent was evaporated under reduced pressure, and the residue was purified with a column chromatography (silicagel, petroleum ether/ethyl acetate) to give (2-amino-4,6-dichloropyrimidin-5-yl)(phenyl)methanol (0.6 g).

$^1$H NMR (400 MHz, DMSO-$d_6$) δ=7.52 (br. s, 2H), 7.33-7.30 (m, 4H), 7.26-7.18 (m, 1H), 6.20 (d, J=4.4 Hz, 1H), 6.03 (d, J=4.9 Hz, 1H);

LCMS (m/z): 270.05 [M+H]$^-$.

(The Second Step)

Manganese dioxide (3.88 g, 44.6 mmol) was added to a 1,2-dichloroethane solution (15 ml) of (2-amino-4,6-dichloropyrimidin-5-yl)(phenyl)methanol (0.6 g, 2.2 mmol) under ice-cooling, and stirred at 80° C. for 3 hours. The reaction mixture was filtered through celite and the solvent was evaporated under reduced pressure to give (2-amino-4,6-dichloropyrimidin-5-yl)(phenyl)methanone (0.5 g).

$^1$H NMR (400 MHz, DMSO-$d_6$) δ 7.97-7.92 (m, 4H), 7.75-7.72 (m, 1H), 7.60-7.56 (m, 2H);

LCMS (m/z): 267.94 [M+H]$^-$.

(The Third Step)

Hydrazine monohydrate (0.1 ml, 1.87 mmol) was added to a THF-solution (15 ml) of (2-amino-4,6-dichloropyrimidin-5-yl)(phenyl)methanone (0.5 g, 1.87 mmol) and stirred at room temperature for 16 hours. A solvent of the reaction mixture was evaporated under reduced pressure, water was added to the obtained residue and the precipitated solid was collected by filtration to give 4-chloro-3-phenyl-1H-pyrazolo[3,4-d]pyrimidin-6-amine (0.35 g).

$^1$H NMR (400 MHz, DMSO-$d_6$) δ 13.38 (br. s, 1H), 7.70-7.68 (m, 2H), 7.50-7.44 (m, 3H), 7.18 (br. s, 2H);

LCMS (m/z): 246.1 [M+H]$^+$.

(The Fourth Step)

A mixed solvent of DME-water (4:1, 10 ml) was added to 2-(6-cyclopropyl-8-fluoro-1-oxoisoquinolin-2(1H)-yl)-6-(4,4,5,5-tetramethyl-1,3,2-dioxaboran-2-yl)benzyl acetate (0.193 g, 0.4 mmol), 4-chloro-3-phenyl-1H-pyrazolo[3,4-d]pyrimidin-6-amine (0.1 g, 0.4 mmol) and potassium carbonate (0.11 g, 0.8 mmol) and the mixture was degassed under argon atmosphere for 30 minutes. Pd(PPh$_3$)$_4$ (23 mg, 0.02 mmol) was added and reacted in a microwave apparatus at 110° C. for 15 minutes. Water was added to the reaction mixture, the precipitated solid was collected by filtration to give 2-(6-amino-3-phenyl-1H-pyrazolo[3,4-d]pyrimidin-4-yl)-6-(6-cyclopropyl-8-fluoro-1-oxoisoquinolin-2(1H)-yl)benzyl acetate (0.3 g) as a crude product. The crude product was dissolved in methanol (20 ml), potassium carbonate (0.4 g) was added and stirred at room temperature for 16 hours. A solvent was evaporated under reduced pressure, water was added to the obtained residue, the precipitated solid was collected by filtration and purified with preparative HPLC to give the titled compound (45 mg).

$^1$H NMR (400 MHz, DMSO-d$_6$) δ 13.18 (br. s, 1H), 7.28-6.94 (m, 13H), 6.61 (d, J=5.9 Hz, 1H), 4.69 (br. s, 1H), 4.49-4.12 (m, 2H), 2.11-2.04 (m, 1H), 1.12-1.07 (m, 2H), 0.89-0.85 (m, 2H);

LCMS (m/z): 519.39 [M+H]$^-$.

Examples 4-22 and 24-93

Each of the Example compounds in the following [Table 1-1] and [Table 1-2] was prepared according to the procedure described in Example above or said procedure combined with a common method well known in the art of organic chemistry, if needed, using appropriate starting material (it is obtained from commercial source, or is prepared by literature procedures or modifications of literature procedures known to persons skilled in the art).

The physicochemical data of each compound were shown in the following [Table 2-1] and [Table 2-2].

TABLE 1-1

| Example | Structure | Name |
|---|---|---|
| 4 | 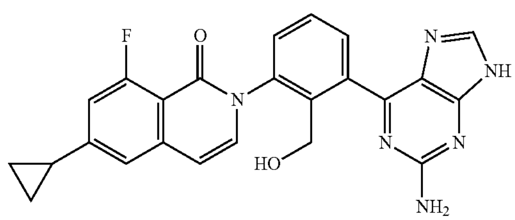 | 2-[3-(2-amino-9H-purin-6-yl)-2-(hydroxymethyl)phenyl]-6-cyclopropyl-8-fluoroisoquinolin-1(2H)-one |
| 5 | 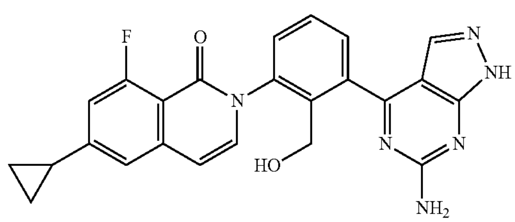 [SMILES: Nc1nc(-c2cccc(-n3ccc4cc(C5CC5)cc(F)c4c3=O)c2CO)c2cc[nH]c2n1] | 2-[3-(6-amino-1H-pyrazolo[3,4-d]pyrimidin-4-yl)-2-(hydroxymethyl)phenyl]-6-cyclopropyl-8-fluoroisoquinolin-1(2H)-one |
| 6 | 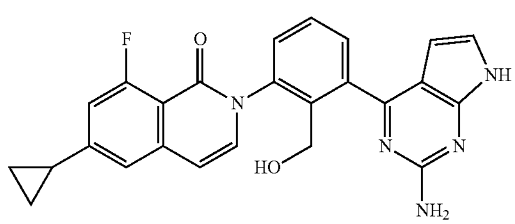 | 2-[3-(2-amino-7H-pyrrolo[2,3-d]pyrimidin-4-yl)-2-(hydroxymethyl)phenyl]-6-cyclopropyl-8-fluoroisoquinolin-1(2H)-one |
| 7 | 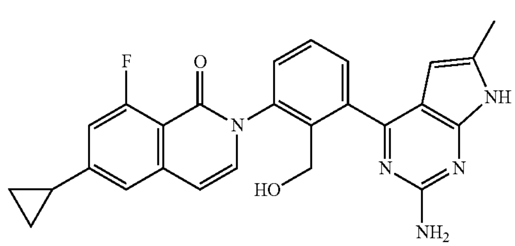 [SMILES: Cc1cc2c(-c3cccc(-n4ccc5cc(C6CC6)cc(F)c5c4=O)c3CO)nc(N)nc2[nH]1] | 2-[3-(2-amino-6-methyl-7H-pyrrolo[2,3-d]pyrimidin-4-yl)-2-(hydroxymethyl)phenyl]-6-cyclopropyl-8-fluoroisoquinolin-1(2H)-one |

TABLE 1-1-continued

| Example | Structure | Name |
| --- | --- | --- |
| 8 | 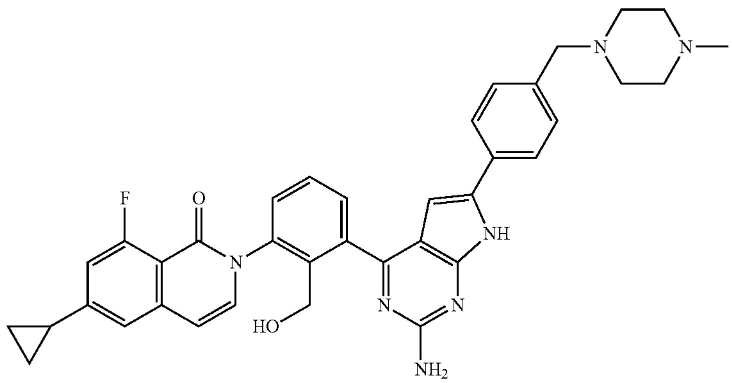 [SMILES: CN1CCN(Cc2ccc(-c3cc4c(-c5cccc(-n6ccc7cc(C8CC8)cc(F)c7c6=O)c5CO)nc(N)nc4[nH]3)cc2)CC1] | 2-[3-(2-amino-6-{4-[(4-methylpiperazin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one |
| 9 | 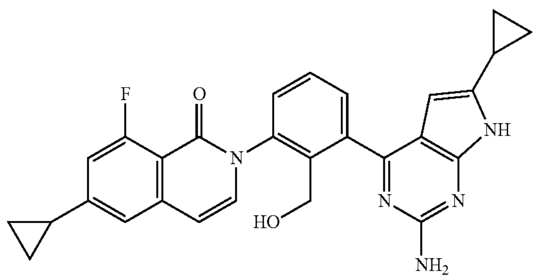 [SMILES: Nc1nc(-c2cccc(-n3ccc4cc(C5CC5)cc(F)c4c3=O)c2CO)c2cc(C3CC3)[nH]c2n1] | 2-[3-(2-amino-6-cyclopropyl-7H-pyrrolo[2,3-d]pyrimidin-4-yl)-2-(hydroxymethyl)phenyl]-6-cyclopropyl-8-fluoroisoquinolin-1(2H)-one |
| 10 | 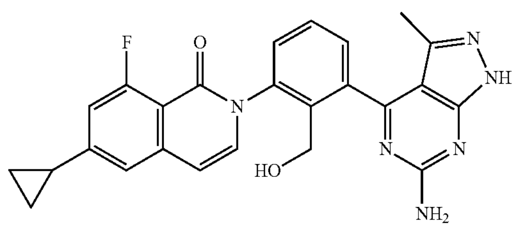 [SMILES: Cc1n[nH]c2nc(N)nc(-c3cccc(-n4ccc5cc(C6CC6)cc(F)c5c4=O)c3CO)c12] | 2-[3-(6-amino-3-methyl-1H-pyrazolo[3,4-d]pyrimidin-4-yl)-2-(hydroxymethyl)phenyl]-6-cyclopropyl-8-fluoroisoquinolin-1(2H)-one |
| 11 | 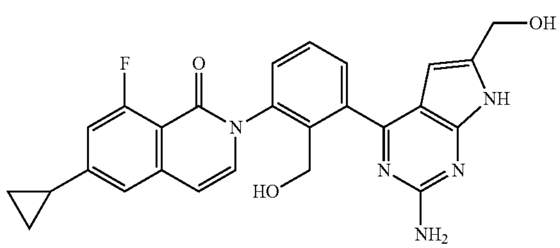 [SMILES: Nc1nc(-c2cccc(-n3ccc4cc(C5CC5)cc(F)c4c3=O)c2CO)c2cc(CO)[nH]c2n1] | 2-{3-[2-amino-6-(hydroxymethyl)-7H-pyrrolo[2,3-d]pyrimidin-4-yl]-2-(hydroxymethyl)phenyl}-6-cyclopropyl-8-fluoroisoquinolin-1(2H)-one |
| 12 | 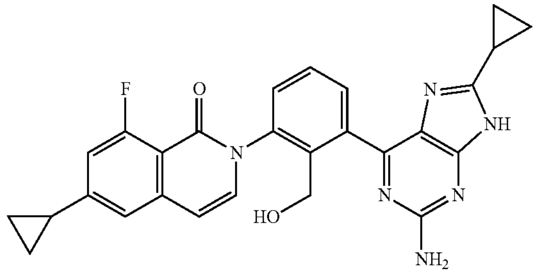 [SMILES: Nc1nc(-c2cccc(-n3ccc4cc(C5CC5)cc(F)c4c3=O)c2CO)c2nc(C3CC3)[nH]c2n1] | 2-[3-(2-amino-8-cyclopropyl-9H-purin-6-yl)-2-(hydroxymethyl)phenyl]-6-cyclopropyl-8-fluoroisoquinolin-1(2H)-one |

TABLE 1-1-continued

| Example | Structure | Name |
|---|---|---|
| 13 | 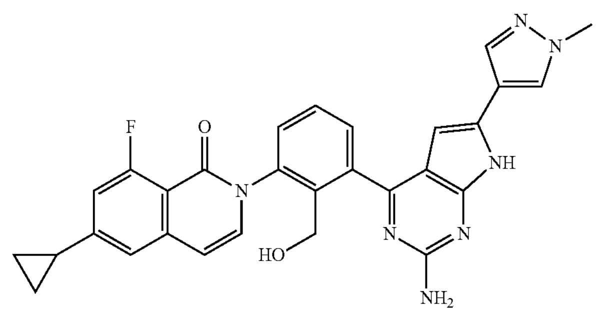 [SMILES: Cn1cc(-c2cc3c(-c4cccc(-n5ccc6cc(C7CC7)cc(F)c6c5=O)c4CO)nc(N)nc3[nH]2)cn1] | 2-{3-[2-amino-6-(1-methyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one |
| 14 | 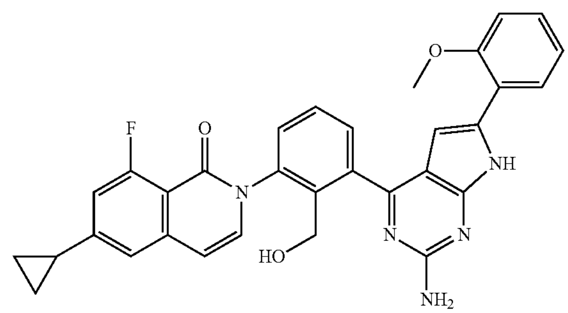 [SMILES: COc1ccccc1-c1cc2c(-c3cccc(-n4ccc5cc(C6CC6)cc(F)c5c4=O)c3CO)nc(N)nc2[nH]1] | 2-{3-[2-amino-6-(2-methoxyphenyl)-7H-pyrrolo[2,3-d]pyrimidin-4-yl]-2-(hydroxymethyl)phenyl}-6-cyclopropyl-8-fluoroisoquinolin-1(2H)-one |
| 15 | 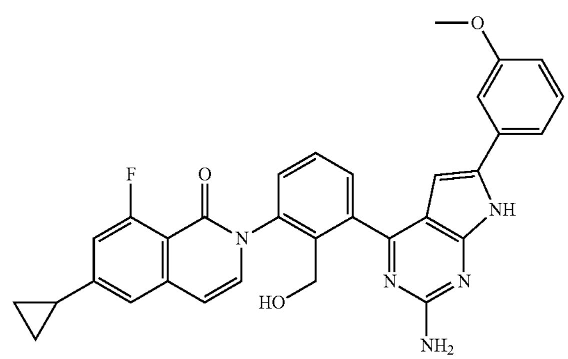 | 2-{3-[2-amino-6-(3-methoxyphenyl)-7H-pyrrolo[2,3-d]pyrimidin-4-yl]-2-(hydroxymethyl)phenyl}-6-cyclopropyl-8-fluoroisoquinolin-1(2H)-one |
| 16 | 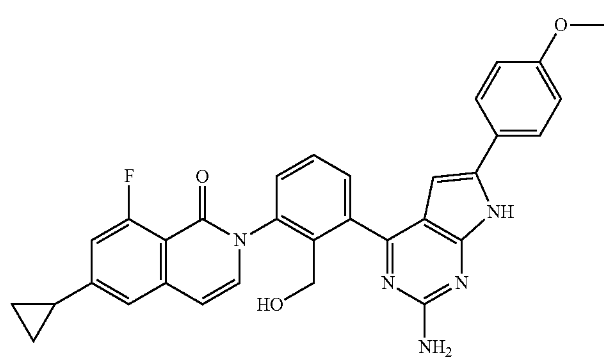 | 2-{3-[2-amino-6-(4-methoxyphenyl)-7H-pyrrolo[2,3-d]pyrimidin-4-yl]-2-(hydroxymethyl)phenyl}-6-cyclopropyl-8-fluoroisoquinolin-1(2H)-one |

TABLE 1-1-continued

| Example | Structure | Name |
| --- | --- | --- |
| 17 | 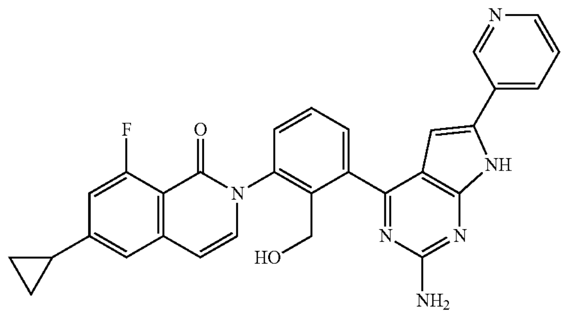 [SMILES: Nc1nc(-c2cccc(-n3ccc4cc(C5CC5)cc(F)c4c3=O)c2CO)c2cc(-c3cccnc3)[nH]c2n1] | 2-{3-[2-amino-6-(pyridin-3-yl)-7H-pyrrolo[2,3-d]pyrimidin-4-yl]-2-(hydroxymethyl)phenyl}-6-cyclopropyl-8-fluoroisoquinolin-1(2H)-one |
| 18 | 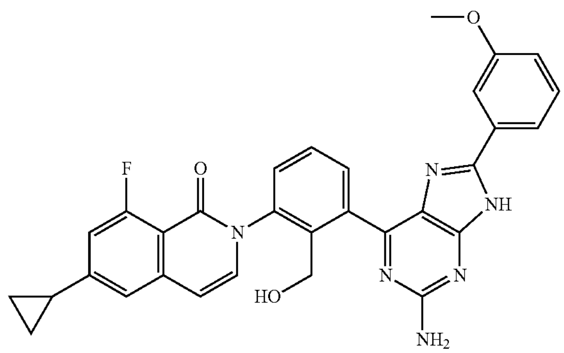 | 2-{3-[2-amino-8-(3-methoxyphenyl)-9H-purin-6-yl]-2-(hydroxymethyl)phenyl}-6-cyclopropyl-8-fluoroisoquinolin-1(2H)-one |
| 19 | 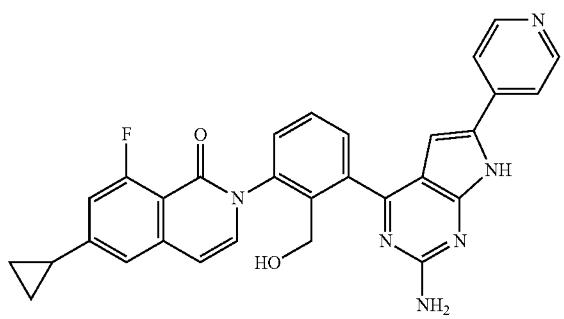 [SMILES: Nc1nc(-c2cccc(-n3ccc4cc(C5CC5)cc(F)c4c3=O)c2CO)c2cc(-c3ccncc3)[nH]c2n1] | 2-{3-[2-amino-6-(pyridin-4-yl)-7H-pyrrolo[2,3-d]pyrimidin-4-yl]-2-(hydroxymethyl)phenyl}-6-cyclopropyl-8-fluoroisoquinolin-1(2H)-one |
| 20 | 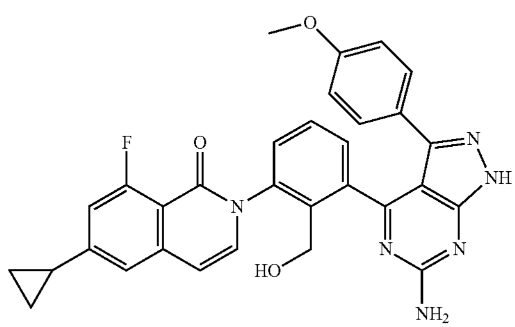 [SMILES: COc1ccc(-c2n[nH]c3nc(N)nc(-c4cccc(-n5ccc6cc(C7CC7)cc(F)c6c5=O)c4CO)c23)cc1] | 2-{3-[6-amino-3-(4-methoxyphenyl)-1H-pyrazolo[3,4-d]pyrimidin-4-yl]-2-(hydroxymethyl)phenyl}-6-cyclopropyl-8-fluoroisoquinolin-1(2H)-one |
| 21 | 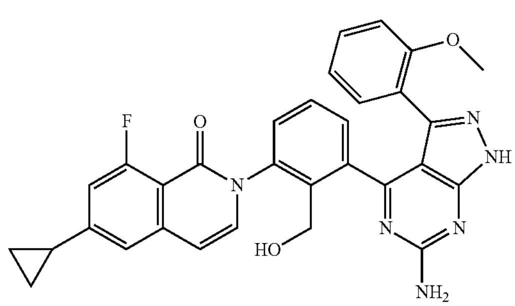 [SMILES: COc1ccccc1-c1n[nH]c2nc(N)nc(-c3cccc(-n4ccc5cc(C6CC6)cc(F)c5c4=O)c3CO)c12] | 2-{3-[6-amino-3-(2-methoxyphenyl)-1H-pyrazolo[3,4-d]pyrimidin-4-yl]-2-(hydroxymethyl)phenyl}-6-cyclopropyl-8-fluoroisoquinolin-1(2H)-one |

TABLE 1-1-continued

| Example | Structure | Name |
|---|---|---|
| 22 | 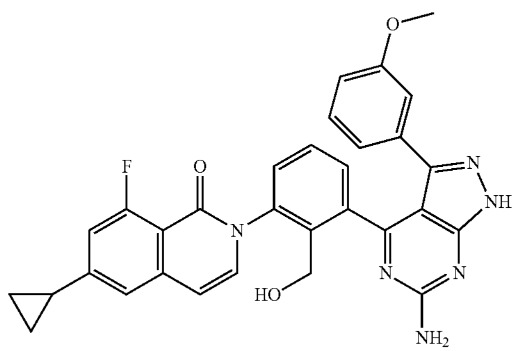 [SMILES: COc1cccc(-c2n[nH]c3nc(N)nc(-c4cccc(-n5ccc6cc(C7CC7)cc(F)c6c5=O)c4CO)c23)c1] | 2-{3-[6-amino-3-(3-methoxyphenyl)-1H-pyrazolo[3,4-d]pyrimidin-4-yl]-2-(hydroxymethyl)phenyl}-6-cyclopropyl-8-fluoroisoquinolin-1(2H)-one |

Example 23

2-(3-{2-amino-6-[1-(oxetan-3-yl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one

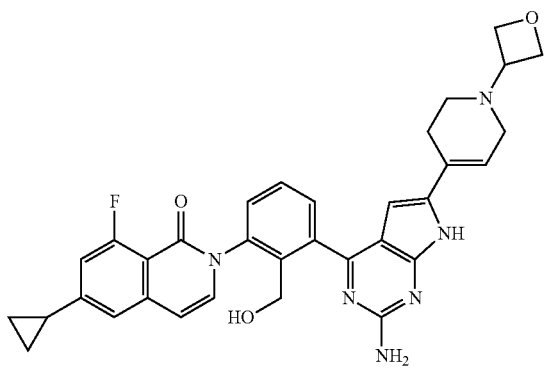 [SMILES: Nc1nc(-c2cccc(-n3ccc4cc(C5CC5)cc(F)c4c3=O)c2CO)c2cc(C3=CCN(C4COC4)CC3)[nH]c2n1]

(The First Step)

Copper iodide (0.25 g, 1.31 mmol), PdCl$_2$(PPh$_3$)$_2$ (0.92 g, 1.31 mmol), trimethylsilylacetylene (3.87 g, 39.4 mmol) and triethylamine (7.32 ml, 52.5 mmol) were added to a DMF-solution (52.5 ml) of 6-chloro-5-iodo-pyrimidin-2,4-diamine (7.1 g, 26.3 mmol), and stirred at 45° C. for 30 minutes. Trimethylsilylacetylene (3.87 g, 39.4 mmol) was further added to the reaction solution and the mixture was stirred at 45° C. for 30 minutes. Water was added to the reaction mixture and extracted with ethyl acetate. The obtained organic layer was washed with water and saturated brine successively, and dried over anhydrous sodium sulfate. A solvent was evaporated under reduced pressure and the residue was purified with flash chromatography to give 6-chloro-5-((trimethylsilyl)ethynyl)pyrimidin-2,4-diamine (6.3 g).

$^1$H NMR (400 MHz, DMSO-d$_6$) δ 6.78 (s, 2H), 0.21 (s, 9H); LCMS (m/z): 241.14 [M+H]$^-$.

(The Second Step)

A 0.1M aqueous solution of sodium hydroxide (58.1 ml, 5.81 mmol) was added to a THF-solution (291 ml) of 6-chloro-5-((trimethylsilyl)ethynyl)pyrimidin-2,4-diamine (7.0 g, 29.1 mmol), and stirred at room temperature for an hour. Water was added to the reaction mixture and extracted with ethyl acetate. The obtained organic layer was washed with water and saturated brine successively, and dried over anhydrous sodium sulfate. A solvent was evaporated under reduced pressure to give 6-chloro-5-ethynylpyrimidin-2,4-diamine (4.85 g).

$^1$H NMR (400 MHz, DMSO-d$_6$) δ 6.75 (s, 2H), 4.50 (s, 1H); LCMS (m/z): 169.01 [M+H]$^-$.

(The Third Step)

Copper iodide (0.215 g, 1.13 mmol), PdCl$_2$(PPh$_3$)$_2$ (1.58 g, 2.25 mmol), tert butyl 4-{[(trifluoromethyl)sulfonyl]oxy}-5,6-dihydropyridin-1(2H)-carboxylate (7.47 g, 22.5 mmol) and triethylamine (6.28 ml, 45.1 mmol) were added to a DMF-solution (225 ml) of 6-chloro-5-ethynylpyrimidin-2,4-diamin (3.8 g, 22.5 mmol), and stirred at 90° C. for 30 minutes. Water was added to the reaction mixture and extracted with ethyl acetate. The obtained organic layer was washed with water and saturated brine successively, and dried over anhydrous sodium sulfate. A solvent was evaporated under reduced pressure and the residue was purified with a flash chromatography to give tert-butyl 4-[(2,4-diamino-6-chloropyridin-5-yl)ethynyl]-5,6-dihydropyridin-1(2H)-carboxylate (4.92 g).

$^1$H NMR (400 MHz, DMSO-d$_6$) δ 6.73 (s, 2H), 6.14 (s, 1H), 3.97-3.90 (m, 2H), 3.44 (t, J=5.7 Hz, 2H), 2.28-2.24 (m, 2H), 1.41 (s, 9H);
LCMS (m/z): 350.13 [M+H]$^-$.

(The Fourth Step)

Potassium tert-butoxide (4.72 g, 42 mmol) was added to a N-methyl pyrrolidone solution (140 ml) of tert-butyl 4-[(2,4-diamino-6-chloropyrimidin-5-yl)ethynyl]-5,6-dihydropyridin-1(2H)-carboxylate (4.9 g, 14 mmol) and stirred at room temperature for an hour. Water was added to the reaction mixture and extracted with ethyl acetate. The obtained organic layer was washed with water and saturated brine successively, and dried over anhydrous sodium sulfate. A solvent was evaporated under reduced pressure and the residue was purified with a flash chromatography to give tert butyl 4-(2-amino-4-chloro-7H-pyrrolo[2,3-d]pyrimidin-6-yl)-5,6-dihydropyridin-1(2H)-carboxylate (2.93 g).

¹H NMR (400 MHz, DMSO-d₆) δ 11.73-11.55 (m, 1H), 6.57 (s, 2H), 6.32 (s, 1H), 6.29-6.16 (m, 1H), 4.14-3.90 (m, 2H), 3.61-3.43 (m, 2H), 2.49-2.35 (m, 2H), 1.42 (s, 9H); LCMS (m/z): 350.18 [M+H]⁻.

(The Fifth Step)

A mixed solvent of DMF-water (5:1, 165 ml) was added to 2-(6-cyclopropyl-8-fluoro-1-oxoisoquinolin-2(1H)-yl)-6-(4,4,5,5-tetramethyl-1,3,2-dioxaboran-2-yl)benzyl acetate (3.96 g, 8.29 mmol), tert-butyl 4-(2-amino-4-chloro-7H-pyrrolo[2,3-d]pyrimidin-6-yl)-5,6-dihydropyridin-1(2H)-carboxylate (2.9 g, 8.29 mmol) and tripotassium phosphate (3.52 g, 16.6 mmol) and the mixture was degassed under argon atmosphere for 30 minutes. Pd(PPh₃)₄ (0.96 g, 0.829 mmol) was added and stirred at 110° C. for 20 minutes. The reaction mixture was diluted with ethyl acetate, washed with water and saturated brine successively, and dried over anhydrous sodium sulfate. A solvent was evaporated under reduced pressure to give tert butyl 4-{4-[2-(acetoxymethyl)-3-(6-cyclopropyl-8-fluoro-1-oxoisoquinolin-2(1H)-yl)phenyl]-2-amino-7H-pyrrolo[2,3-d]pyrimidin-6-yl}-5,6-dihydropyridin-1(2H)-carboxylate (5.43 g).

LCMS (m/z): 665.37 [M+H]⁻.

(The Sixth Step)

Triethylamine (4.45 ml, 32 mmol) and acetyl chloride (1.89 ml, 26.6 mmol) were added to a THF-solution (53 ml) of tert butyl 4-{4-[2-(acetoxymethyl)-3-(6-cyclopropyl-8-fluoro-1-oxoisoquinolin-2(1H)-yl)phenyl]-2-amino-7H-pyrrolo[2,3-d]pyrimidin-6-yl}-5,6-dihydropyridin-1(2H)-carboxylate (3.54 g, 5.33 mmol), and stirred at room temperature for an hour. Water was added to the reaction mixture and extracted with ethyl acetate. The obtained organic layer was washed with water, 1M solution of sodium hydroxide and saturated brine successively and dried over anhydrous sodium sulfate. A solvent was evaporated to give tert-butyl 4-{2-acetamide-4-[2-(acetoxymethyl)-3-(6-cyclopropyl-8-fluoro-1-oxoisoquinolin-2(1H)-yl)phenyl]-7H-pyrrolo[2,3-d]pyrimidin-6-yl}-5,6-dihydropyridin-1(2H)-carboxylate (5.44 g) as a crude product.

LCMS (m/z): 707.43 [M+H]⁻.

(The Seventh Step)

A 4M hydrogen chloride in 1,4-dioxane solution (50 ml) was added to a DCM solution (150 ml) of tert-butyl 4-{2-acetamide-4-[2-(acetoxymethyl)-3-(6-cyclopropyl-8-fluoro-1-oxoisoquinolin-2(1H)-yl)phenyl]-7H-pyrrolo[2,3-d]pyrimidin-6-yl}-5,6-dihydropyridin-1(2H)-carboxylate (6.66 g, 9.42 mmol) and stirred at room temperature for 6 hours. A 4M aqueous solution of sodium hydroxide (50 ml) was added to the reaction mixture, water was added thereto and extracted with chloroform. The obtained organic layer was washed with water and saturated brine successively and dried over anhydrous sodium sulfate. A solvent was evaporated under reduced pressure and the obtained residue was purified with flash chromatography to give 2-[2-acetamide-6-(1,2,3,6-tetrahydropyridin-4-yl)-7H-pyrrolo[2,3-d]pyrimidin-4-yl]-6-(6-cyclopropyl-8-fluoro-1-oxoisoquinolin-2(1H)-yl)benzyl acetate (2.66 g).

¹H NMR (400 MHz, DMSO-d₆) δ 12.47 (s, 1H), 10.53 (s, 1H), 7.77-7.66 (m, 2H), 7.54 (dd, J=6.8, 2.4 Hz, 1H), 7.40 (d, J=7.4 Hz, 1H), 7.28 (d, J=1.7 Hz, 1H), 7.00 (dd, J=13.3, 1.7 Hz, 1H), 6.64 (dd, J=7.5, 2.1 Hz, 1H), 6.57-6.50 (m, 1H), 6.41 (s, 1H), 5.21 (d, J=12.6 Hz, 1H), 4.99 (d, J=12.6 Hz, 1H), 3.71-3.66 (m, 2H), 3.18 (t, J=6.0 Hz, 2H), 2.62-2.57 (m, 2H), 2.15 (s, 3H), 2.13-2.02 (m, 1H), 1.51 (s, 3H), 1.15-1.05 (m, 2H), 0.94-0.86 (m, 2H);

LCMS (m/z): 607.31 [M+H].

(The Eighth Step)

Oxetan-3-one (1.25 g, 17.3 mmol) and sodium triacetoxyborohydride (3.67 g, 17.3 mmol) were added to DCM solution (69 mmol) of 2-[2-acetamide-6-(1,2,3,6-tetrahydropyridin-4-yl)-7H-pyrrolo[2,3-d]pyrimidin-4-yl]-6-(6-cyclopropyl-8-fluoro-1-oxoisoquinolin-2(1H)-yl)benzyl acetate (2.1 g, 3.46 mmol), and stirred at room temperature for an hour. Oxetan-3-one (1.25 g, 17.3 mmol) and sodium triacetoxyborohydride (3.67 g, 17.3 mmol) were added again to the reaction mixture and stirred at room temperature for an hour further. Water was added to the reaction mixture, and extracted with ethyl acetate. The obtained organic layer was washed with water, a 1M aqueous solution of sodium hydroxide, and saturated brine successively. and dried over anhydrous sodium sulfate. A solvent was evaporated under reduced pressure to give 2-{2-acetamide-6-[1-(oxetan-3-yl)-1,2,3,6-tetrahydropyridin-4-yl]-7H-pyrrolo[2,3-d]pyrimidin-4-yl}-6-(6-cyclopropyl-8-fluoro-1-oxoisoquinolin-2(1H)-yl)benzyl acetate (2.29 g).

¹H NMR (400 MHz, DMSO-d₆) δ 12.48 (s, 1H), 10.52 (s, 1H), 7.77-7.66 (m, 2H), 7.53 (dd, J=7.0, 2.2 Hz, 1H), 7.44-7.35 (m, 1H), 7.28 (d, J=1.7 Hz, 1H), 7.00 (dd, J=13.3, 1.7 Hz, 1H), 6.63 (dd, J=7.6, 2.1 Hz, 1H), 6.59-6.52 (m, 1H), 6.31 (s, 1H), 5.22 (d, J=12.6 Hz, 1H), 4.99 (d, J=12.6 Hz, 1H), 4.67-4.46 (m, 4H), 3.61-3.50 (m, 1H), 3.06-3.01 (m, 2H), 2.51-2.43 (m, 4H), 2.16 (s, 3H), 2.12-2.02 (m, 1H), 1.51 (s, 3H), 1.15-1.01 (m, 2H), 0.94-0.80 (m, 2H);

LCMS (m/z): 663.37 [M+H]⁻.

(The Ninth Step)

A 2M aqueous solution of sodium hydroxide (50 ml) was added to a methanol-solution (100 ml) of 2-{2-acetamide-6-[1-(oxetan-3-yl)-1,2,3,6-tetrahydropyridin-4-yl]-7H-pyrrolo[2,3-d]pyrimidin-4-yl}-6-(6-cyclopropyl-8-fluoro-1-oxoisoquinolin-2(1H)-yl)benzyl acetate (2.3 g, 3.47 mmol), and stirred at 70° C. for 2 hours. Water was added to the reaction mixture and extracted with ethyl acetate. The obtained organic layer was washed with water and saturated brine successively and dried over anhydrous sodium sulfate. A solvent was evaporated under reduced pressure to give the titled product (1.4 g).

¹H NMR (400 MHz, DMSO-d₆) δ 11.52 (s, 1H), 7.72 (dd, J=7.8, 1.3 Hz, 1H), 7.64-7.53 (m, 1H), 7.46 (dd, J=7.8, 1.3 Hz, 1H), 7.37 (d, J=7.4 Hz, 1H), 7.28 (d, J=1.6 Hz, 1H), 6.99 (dd, J=13.2, 1.7 Hz, 1H), 6.62 (dd, J=7.4, 2.1 Hz, 1H), 6.41 (s, 2H), 6.38-6.32 (m, 1H), 6.27-6.18 (m, 1H), 5.20 (dd, J=8.8, 4.5 Hz, 1H), 4.61-4.46 (m, 4H), 4.25 (dd, J=12.0, 4.2 Hz, 1H), 4.06 (dd, J=12.0, 8.8 Hz, 1H), 3.60-3.48 (m, 1H), 3.04-2.98 (m, 2H), 2.48-2.43 (m, 4H), 2.14-2.00 (m, 1H), 1.15-1.01 (m, 2H), 0.92-0.82 (m, 2H);

LCMS (m/z): 579.60 [M+H]⁻.

TABLE 1-2

| Example | Structure | Name |
|---|---|---|
| 24 | 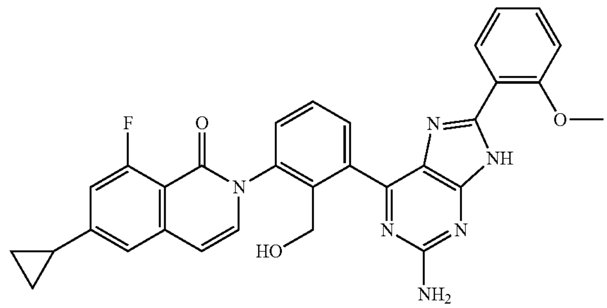 [SMILES: COc1ccccc1-c1nc2c(-c3cccc(-n4ccc5cc(C6CC6)cc(F)c5c4=O)c3CO)nc(N)nc2[nH]1] | 2-{3-[2-amino-8-(2-methoxyphenyl)-9H-purin-6-yl]-2-(hydroxymethyl)phenyl}-6-cyclopropyl-8-fluoroisoquinolin-1(2H)-one |
| 25 | 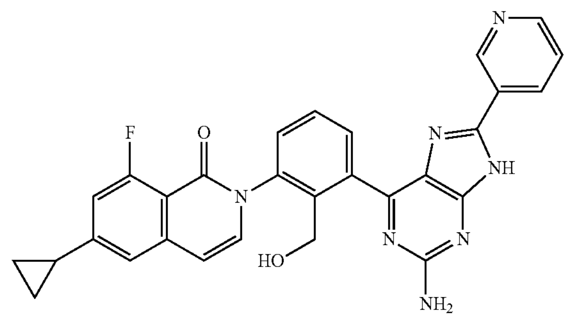 | 2-{3-[2-amino-8-(pyridin-3-yl)-9H-purin-6-yl]-2-(hydroxymethyl)phenyl}-6-cyclopropyl-8-fluoroisoquinolin-1(2H)-one |
| 26 | 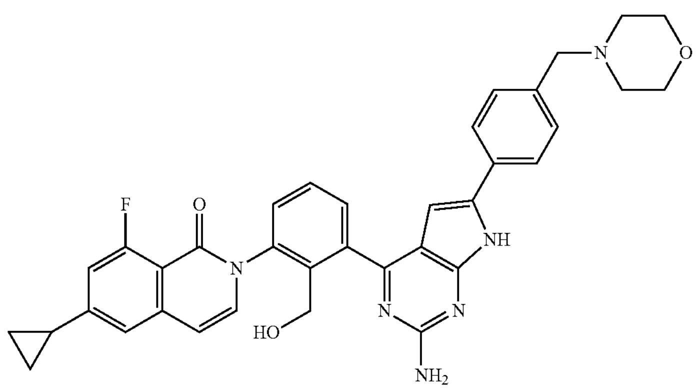 [SMILES: Nc1nc(-c2cccc(-n3ccc4cc(C5CC5)cc(F)c4c3=O)c2CO)c2cc(-c3ccc(CN4CCOCC4)cc3)[nH]c2n1] | 2-(3-{2-amino-6-[4-(morpholinomethyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 27 | 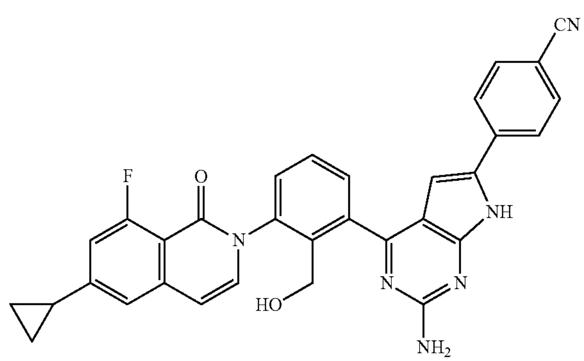 [SMILES: N#Cc1ccc(-c2cc3c(-c4cccc(-n5ccc6cc(C7CC7)cc(F)c6c5=O)c4CO)nc(N)nc3[nH]2)cc1] | 4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}benzonitrile |

TABLE 1-2-continued

| Example | Structure | Name |
|---|---|---|
| 28 | 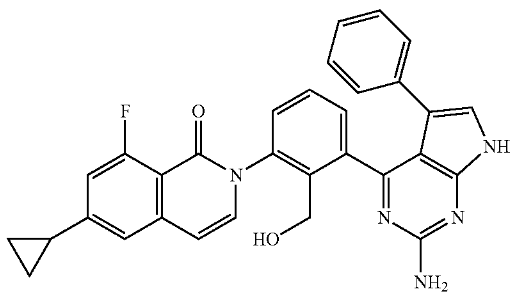 [SMILES: Nc1nc(-c2cccc(-n3ccc4cc(C5CC5)cc(F)c4c3=O)c2CO)c2c(-c3ccccc3)c[nH]c2n1] | 2-[3-(2-amino-5-phenyl-7H-pyrrolo[2,3-d]pyrimidin-4-yl)-2-(hydroxymethyl)phenyl]-6-cyclopropyl-8-fluoroisoquinolin-1(2H)-one |
| 29 | 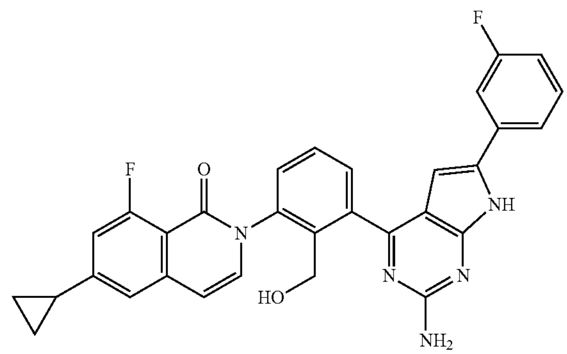 [SMILES: Nc1nc(-c2cccc(-n3ccc4cc(C5CC5)cc(F)c4c3=O)c2CO)c2cc(-c3cccc(F)c3)[nH]c2n1] | 2-{3-[2-amino-6-(3-fluorophenyl)-7H-pyrrolo[2,3-d]pyrimidin-4-yl]-2-(hydroxymethyl)phenyl}-6-cyclopropyl-8-fluoroisoquinolin-1(2H)-one |
| 30 | 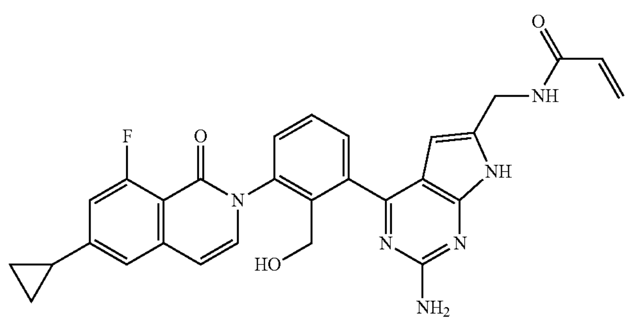 [SMILES: C=CC(=O)NCc1cc2c(-c3cccc(-n4ccc5cc(C6CC6)cc(F)c5c4=O)c3CO)nc(N)nc2[nH]1] | N-({2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}methyl)acrylamide |
| 31 | 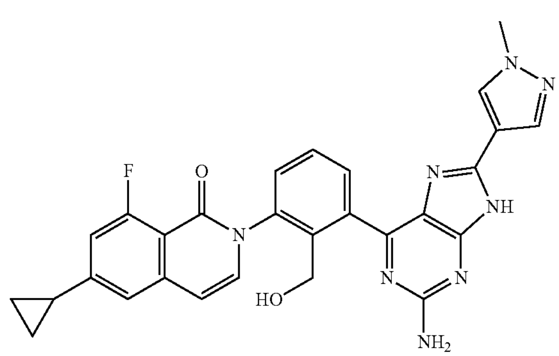 [SMILES: Cn1cc(-c2nc3c(-c4cccc(-n5ccc6cc(C7CC7)cc(F)c6c5=O)c4CO)nc(N)nc3[nH]2)cn1] | 2-{3-[2-amino-8-(1-methyl-1H-pyrazol-4-yl)-9H-purin-6-yl]-2-(hydroxymethyl)phenyl}-6-cyclopropyl-8-fluoroisoquinolin-1(2H)-one |

TABLE 1-2-continued

| Example | Structure | Name |
|---|---|---|
| 32 | 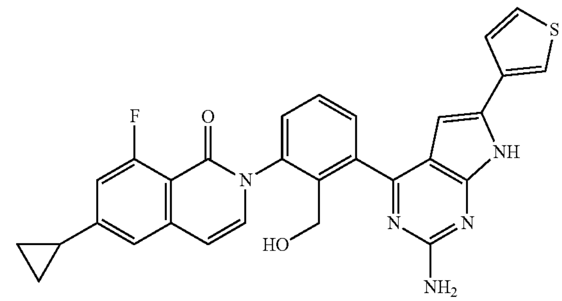 [SMILES: Nc1nc(-c2cccc(-n3ccc4cc(C5CC5)cc(F)c4c3=O)c2CO)c2cc(-c3ccsc3)[nH]c2n1] | 2-{3-[2-amino-6-(thiophen-3-yl)-7H-pyrrolo[2,3-d]pyrimidin-4-yl]-2-(hydroxy-methyl)phenyl}-6-cyclopropyl-8-fluoroisoquinolin-1(2H)-one |
| 33 | 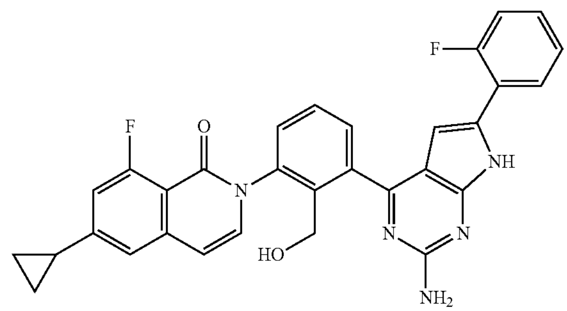 [SMILES: Nc1nc(-c2cccc(-n3ccc4cc(C5CC5)cc(F)c4c3=O)c2CO)c2cc(-c3ccccc3F)[nH]c2n1] | 2-{3-[2-amino-6-(2-fluorophenyl)-7H-pyrrolo[2,3-d]pyrimidin-4-yl]-2-(hydroxy-methyl)phenyl}-6-cyclopropyl-8-fluoroisoquinolin-1(2H)-one |
| 34 | 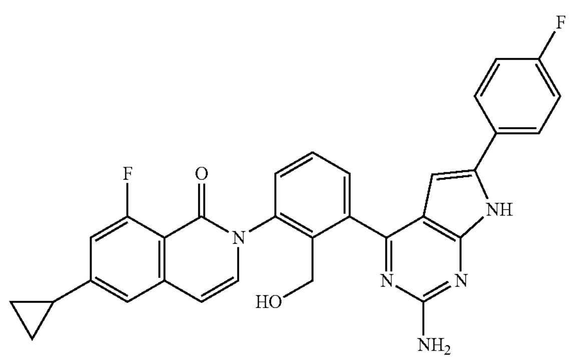 | 2-{3-[2-amino-6-(4-fluorophenyl)-7H-pyrrolo[2,3-d]pyrimidin-4-yl]-2-(hydroxy-methyl)phenyl}-6-cyclopropyl-8-fluoroisoquinolin-1(2H)-one |
| 35 | 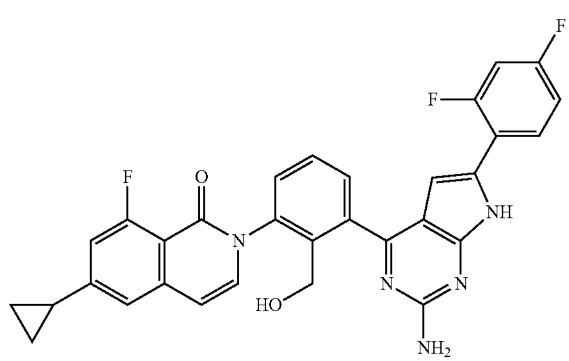 [SMILES: Nc1nc(-c2cccc(-n3ccc4cc(C5CC5)cc(F)c4c3=O)c2CO)c2cc(-c3ccc(F)cc3F)[nH]c2n1] | 2-{3-[2-amino-6-(2,4-difluorophenyl)-7H-pyrrolo[2,3-d]pyrimidin-4-yl]-2-(hydroxy-methyl)phenyl}-6-cyclopropyl-8-fluoroisoquinolin-1(2H)-one |

TABLE 1-2-continued

| Example | Structure | Name |
| --- | --- | --- |
| 36 | 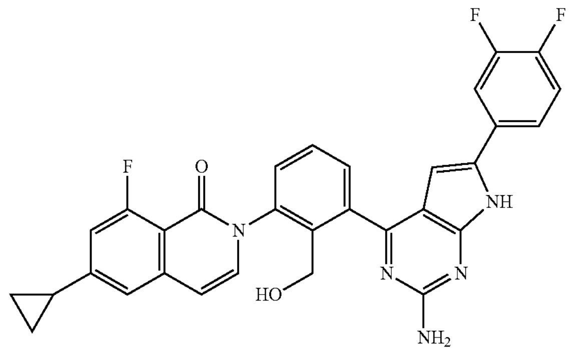 [SMILES: Nc1nc(-c2cccc(-n3ccc4cc(C5CC5)cc(F)c4c3=O)c2CO)c2cc(-c3ccc(F)c(F)c3)[nH]c2n1] | 2-{3-[2-amino-6-(3,4-difluorophenyl)-7H-pyrrolo[2,3-d]pyrimidin-4-yl]-2-(hydroxymethyl)phenyl}-6-cyclopropyl-8-fluoroisoquinolin-1(2H)-one |
| 37 | 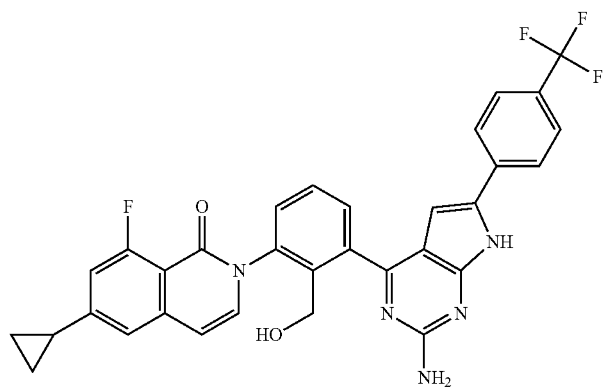 [SMILES: Nc1nc(-c2cccc(-n3ccc4cc(C5CC5)cc(F)c4c3=O)c2CO)c2cc(-c3ccc(C(F)(F)F)cc3)[nH]c2n1] | 2-(3-{2-amino-6-[4-(trifluoromethyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 38 | 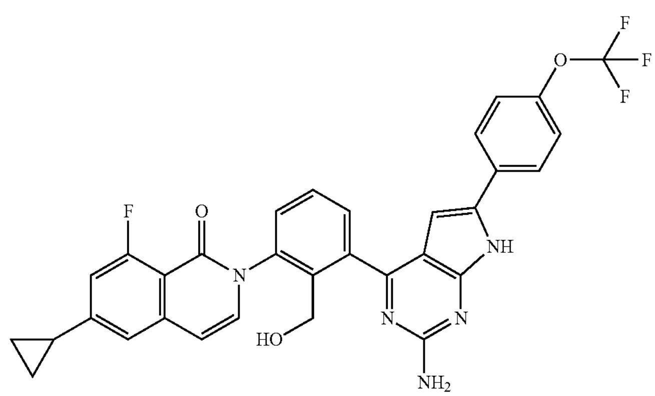 [SMILES: Nc1nc(-c2cccc(-n3ccc4cc(C5CC5)cc(F)c4c3=O)c2CO)c2cc(-c3ccc(OC(F)(F)F)cc3)[nH]c2n1] | 2-(3-{2-amino-6-[4-(trifluoromethoxy)phenyl]-7H-pyrrolo[2,3-d]pyrimidin-4-yl}-2-(hydroxymethyl)phenyl)-6-cyclopropyl-8-fluoroisoquinolin-1(2H)-one |
| 39 | 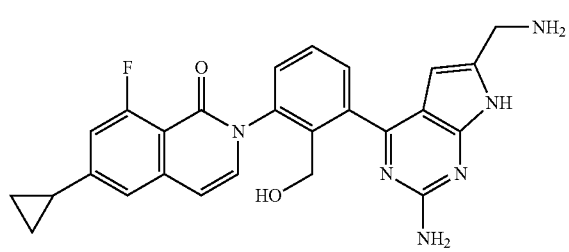 [SMILES: NCc1cc2c(-c3cccc(-n4ccc5cc(C6CC6)cc(F)c5c4=O)c3CO)nc(N)nc2[nH]1] | 2-{3-[2-amino-6-(aminomethyl)-7H-pyrrolo[2,3-d]pyrimidin-4-yl]-2-(hydroxymethyl)phenyl}-6-cyclopropyl-8-fluoroisoquinolin-1(2H)-one |

TABLE 1-2-continued

| Example | Structure | Name |
|---|---|---|
| 40 | 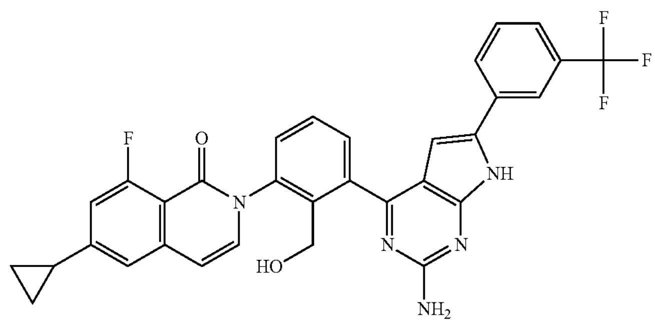 [SMILES: Nc1nc(-c2cccc(-n3ccc4cc(C5CC5)cc(F)c4c3=O)c2CO)c2cc(-c3cccc(C(F)(F)F)c3)[nH]c2n1] | 2-(3-{2-amino-6-[3-(trifluoromethyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 41 | 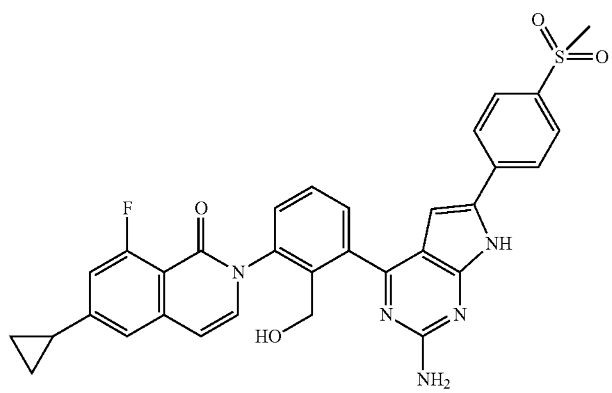 [SMILES: CS(=O)(=O)c1ccc(-c2cc3c(-c4cccc(-n5ccc6cc(C7CC7)cc(F)c6c5=O)c4CO)nc(N)nc3[nH]2)cc1] | 2-(3-{2-amino-6-[4-(methylsulfonyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 42 | 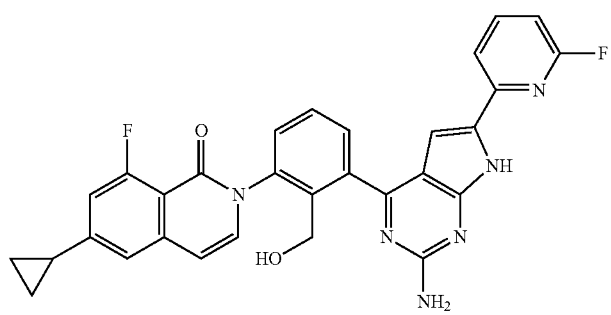 [SMILES: Nc1nc(-c2cccc(-n3ccc4cc(C5CC5)cc(F)c4c3=O)c2CO)c2cc(-c3cccc(F)n3)[nH]c2n1] | 2-{3-[2-amino-6-(6-fluoropyridin-2-yl)-7H-pyrrolo[2,3-d]pyrimidin-4-yl]-2-(hydroxymethyl)phenyl)-6-cyclopropyl-8-fluoroisoquinolin-1(2H)-one |
| 43 | 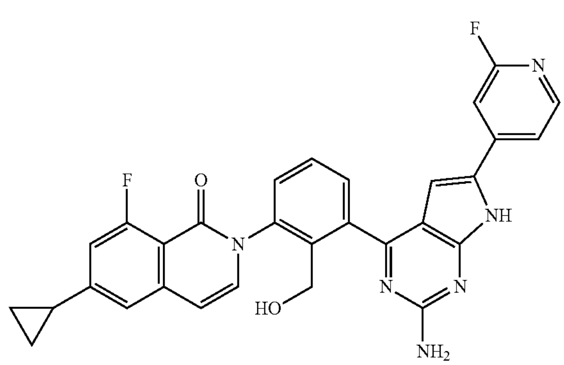 | 2-{3-[2-amino-6-(2-fluoropyridin-4-yl)-7H-pyrrolo[2,3-d]pyrimidin-4-yl]-2-(hydroxymethyl)phenyl)-6-cyclopropyl-8-fluoroisoquinolin-1(2H)-one |

TABLE 1-2-continued

| Example | Structure | Name |
|---|---|---|
| 44 | 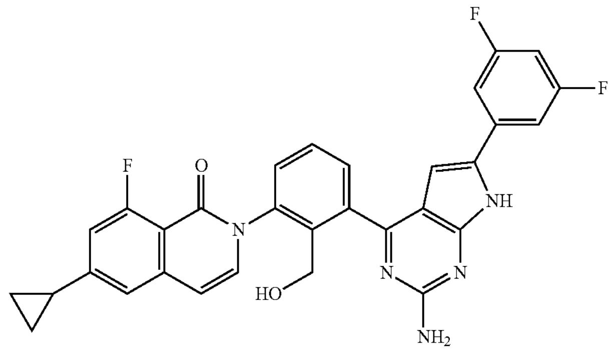 [SMILES: Nc1nc(-c2cccc(-n3ccc4cc(C5CC5)cc(F)c4c3=O)c2CO)c2cc(-c3cc(F)cc(F)c3)[nH]c2n1] | 2-{3-[2-amino-6-(3,5-difluorophenyl)-7H-pyrrolo[2,3-d]pyrimidin-4-yl]-2-(hydroxymethyl)phenyl}-6-cyclopropyl-8-fluoroisoquinolin-1(2H)-one |
| 45 | 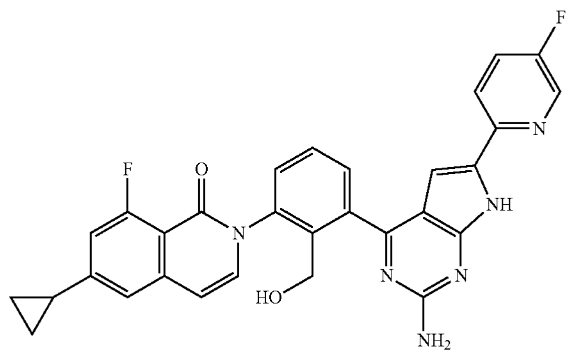 | 2-{3-[2-amino-6-(5-fluoropyridin-2-yl)-7H-pyrrolo[2,3-d]pyrimidin-4-yl]-2-(hydroxymethyl)phenyl}-6-cyclopropyl-8-fluoroisoquinolin-1(2H)-one |
| 46 | 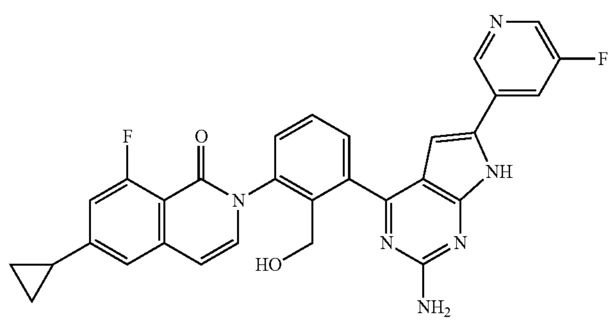 [SMILES: Nc1nc(-c2cccc(-n3ccc4cc(C5CC5)cc(F)c4c3=O)c2CO)c2cc(-c3cncc(F)c3)[nH]c2n1] | 2-{3-[2-amino-6-(5-fluoropyridin-3-yl)-7H-pyrrolo[2,3-d]pyrimidin-4-yl]-2-(hydroxymethyl)phenyl}-6-cyclopropyl-8-fluoroisoquinolin-1(2H)-one |
| 47 | 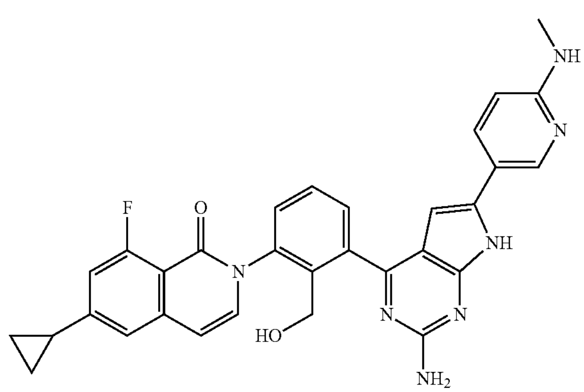 [SMILES: CNc1ccc(-c2cc3c(-c4cccc(-n5ccc6cc(C7CC7)cc(F)c6c5=O)c4CO)nc(N)nc3[nH]2)cn1] | 2-(3-{2-amino-6-[6-(methylamino)pyridin-3-yl]-7H-pyrrolo[2,3-d]pyrimidin-4-yl}-2-(hydroxymethyl)phenyl)-6-cyclopropyl-8-fluoroisoquinolin-1(2H)-one |

TABLE 1-2-continued

| Example | Structure | Name |
|---|---|---|
| 48 | 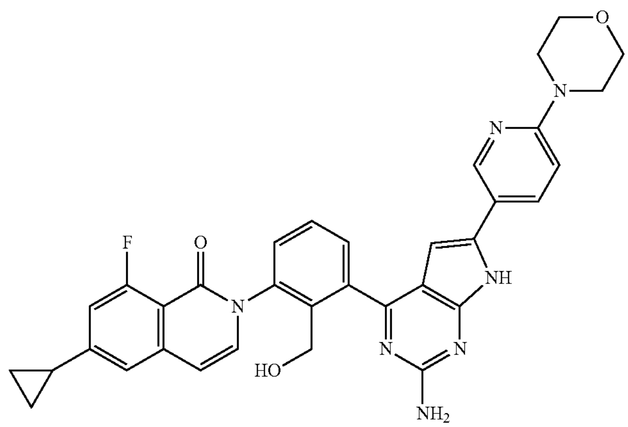 [SMILES: Nc1nc(-c2cccc(-n3ccc4cc(C5CC5)cc(F)c4c3=O)c2CO)c2cc(-c3ccc(N4CCOCC4)nc3)[nH]c2n1] | 2-{3-[2-amino-6-(6-(morpholinopyridin-3-yl)-7H-pyrrolo[2,3-d]pyrimidin-4-yl]-2-(hydroxymethyl)phenyl}-6-cyclopropyl-8-fluoroisoquinolin-1(2H)-one |
| 49 | 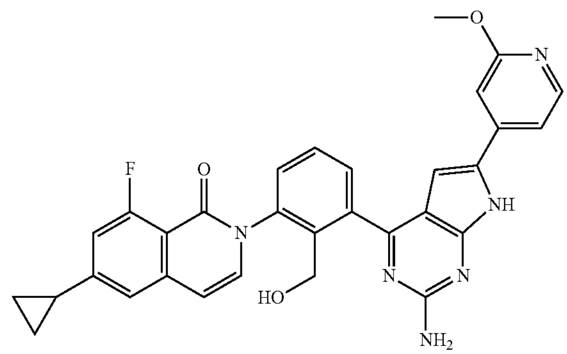 [SMILES: COc1cc(-c2cc3c(-c4cccc(-n5ccc6cc(C7CC7)cc(F)c6c5=O)c4CO)nc(N)nc3[nH]2)ccn1] | 2-{3-[2-amino-6-(2-(methoxypyridin-4-yl)-7H-pyrrolo[2,3-d]pyrimidin-4-yl]-2-(hydroxymethyl)phenyl}-6-cyclopropyl-8-fluoroisoquinolin-1(2H)-one |
| 50 | 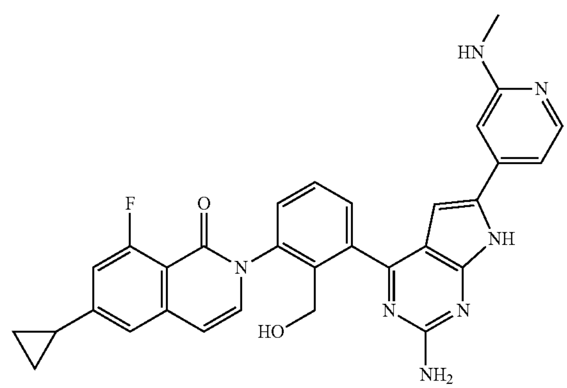 [SMILES: CNc1cc(-c2cc3c(-c4cccc(-n5ccc6cc(C7CC7)cc(F)c6c5=O)c4CO)nc(N)nc3[nH]2)ccn1] | 2-(3-{2-amino-6-[2-(methylamino)pyridin-4-yl]-7H-pyrrolo[2,3-d]pyrimidin-4-yl}-2-(hydroxymethyl)phenyl)-6-cyclopropyl-8-fluoroisoquinolin-1(2H)-one |
| 51 | 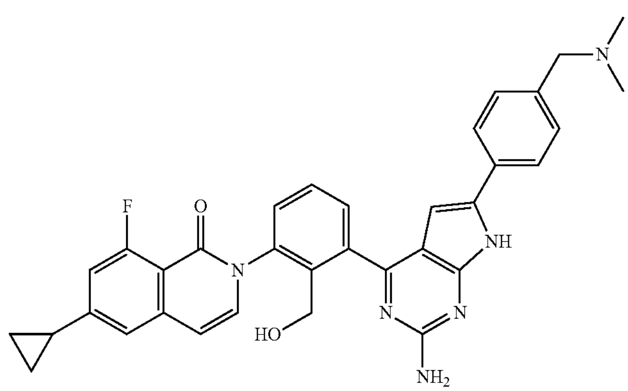 [SMILES: CN(C)Cc1ccc(-c2cc3c(-c4cccc(-n5ccc6cc(C7CC7)cc(F)c6c5=O)c4CO)nc(N)nc3[nH]2)cc1] | 2-[3-(2-amino-6-{4-[(dimethylamino)methyl]phenyl}-7H-pyrrolo[2,3-d]pyrimidin-4-yl)-2-(hydroxymethyl)phenyl]-6-cyclopropyl-8-fluoroisoquinolin-1(2H)-one |

TABLE 1-2-continued

| Example | Structure | Name |
|---|---|---|
| 52 | 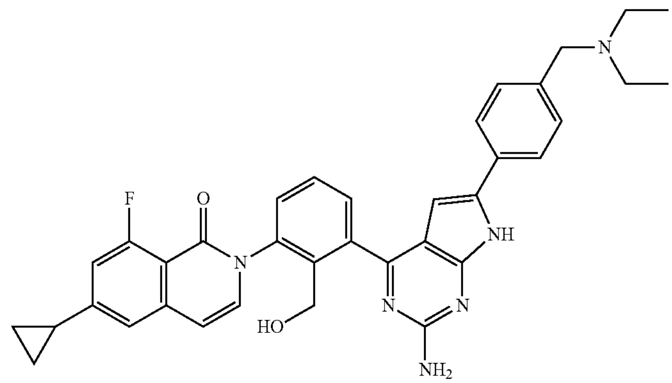 [SMILES: CCN(CC)Cc1ccc(-c2cc3c(-c4cccc(-n5ccc6cc(C7CC7)cc(F)c6c5=O)c4CO)nc(N)nc3[nH]2)cc1] | 2-[3-(2-amino-6-{4-[(diethylamino)methyl]phenyl}-7H-pyrrolo[2,3-d]pyrimidin-4-yl)-2-(hydroxymethyl)phenyl]-6-cyclopropyl-8-fluoroisoquinolin-1(2H)-one |
| 53 | 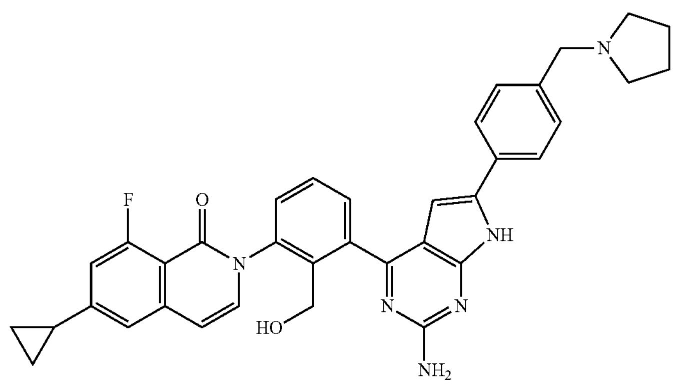 [SMILES: Nc1nc(-c2cccc(-n3ccc4cc(C5CC5)cc(F)c4c3=O)c2CO)c2cc(-c3ccc(CN4CCCC4)cc3)[nH]c2n1] | 2-(3-{2-amino-6-[4-(pyrrolidin-1-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 54 | 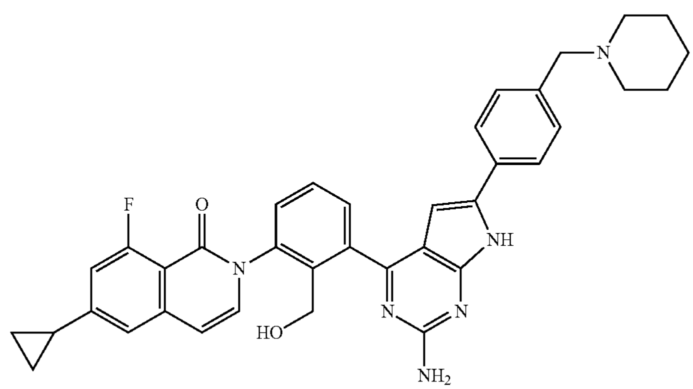 [SMILES: Nc1nc(-c2cccc(-n3ccc4cc(C5CC5)cc(F)c4c3=O)c2CO)c2cc(-c3ccc(CN4CCCCC4)cc3)[nH]c2n1] | 2-(3-{2-amino-6-[4-(piperidin-1-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one |
| 55 | 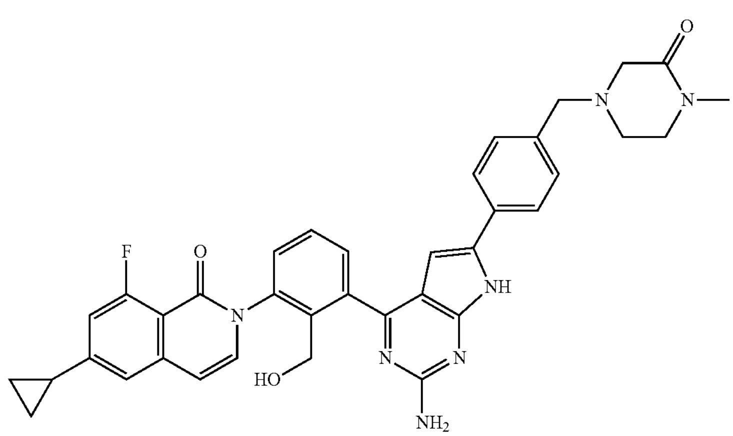 [SMILES: CN1CCN(Cc2ccc(-c3cc4c(-c5cccc(-n6ccc7cc(C8CC8)cc(F)c7c6=O)c5CO)nc(N)nc4[nH]3)cc2)CC1=O] | 2-[3-(2-amino-6-{4-[(4-methyl-3-oxopiperazin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one |

TABLE 1-2-continued

| Example | Structure | Name |
|---|---|---|
| 56 | 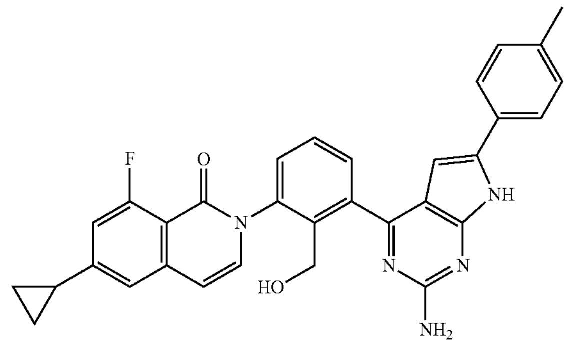 [SMILES: Cc1ccc(-c2cc3c(-c4cccc(-n5ccc6cc(C7CC7)cc(F)c6c5=O)c4CO)nc(N)nc3[nH]2)cc1] | 2-{3-[2-amino-6-(p-tolyl)-7H-pyrrolo[2,3-d]pyrimidin-4-yl]-2-(hydroxymethyl)phenyl}-6-cyclopropyl-8-fluoroisoquinolin-1(2H)-one |
| 57 | 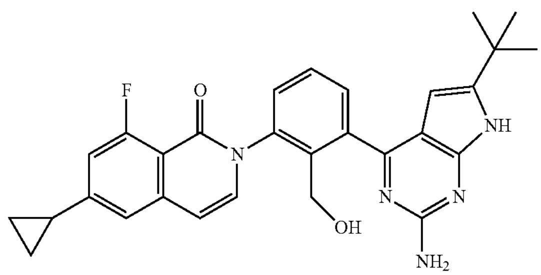 [SMILES: CC(C)(C)c1cc2c(-c3cccc(-n4ccc5cc(C6CC6)cc(F)c5c4=O)c3CO)nc(N)nc2[nH]1] | 2-{3-[2-amino-6-(tert-butyl)-7H-pyrrolo[2,3-d]pyrimidin-4-yl]-2-(hydroxymethyl)phenyl}-6-cyclopropyl-8-fluoroisoquinolin-1(2H)-one |
| 58 | 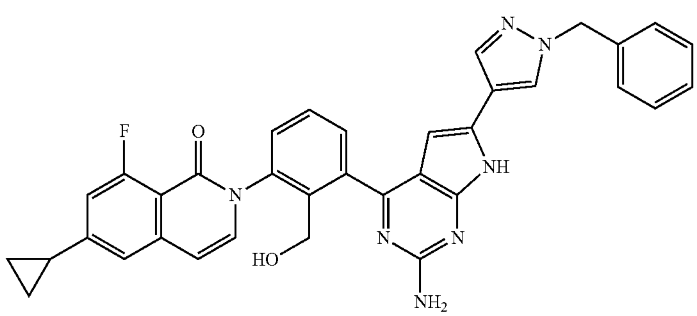 [SMILES: Nc1nc(-c2cccc(-n3ccc4cc(C5CC5)cc(F)c4c3=O)c2CO)c2cc(-c3cnn(Cc4ccccc4)c3)[nH]c2n1] | 2-{3-[2-amino-6-(1-benzyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one |
| 59 | 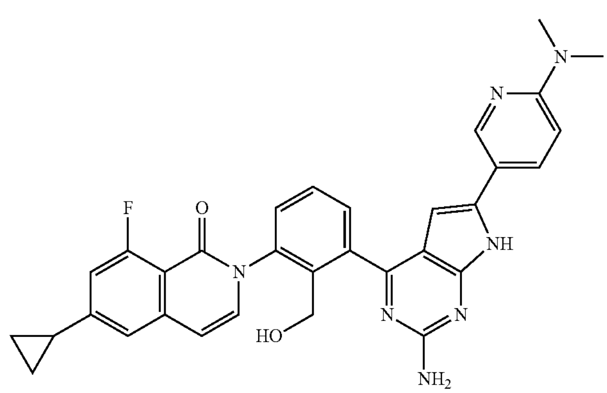 [SMILES: CN(C)c1ccc(-c2cc3c(-c4cccc(-n5ccc6cc(C7CC7)cc(F)c6c5=O)c4CO)nc(N)nc3[nH]2)cn1] | 2-(3-{2-amino-6-[6-(dimethylamino)pyridin-3-yl]-7H-pyrrolo[2,3-d]pyrimidin-4-yl}-2-(hydroxymethyl)phenyl)-6-cyclopropyl-8-fluoroisoquinolin-1(2H)-one |

TABLE 1-2-continued

| Example | Structure | Name |
| --- | --- | --- |
| 60 | 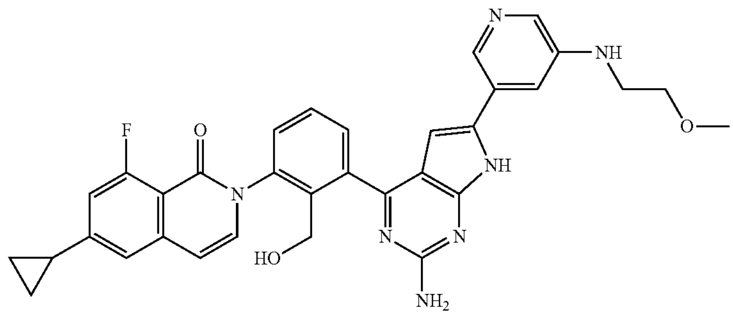 [SMILES: COCCNc1cncc(-c2cc3c(-c4cccc(-n5ccc6cc(C7CC7)cc(F)c6c5=O)c4CO)nc(N)nc3[nH]2)c1] | 2-[3-(2-amino-6-{5-[(2-methoxy-ethyl)amino]pyridin-3-yl}-7H-pyrrolo[2,3-d]pyrimidin-4-yl)-2-(hydroxy-methyl)phenyl]-6-cyclopropyl-8-fluoroisoquinolin-1(2H)-one |
| 61 | 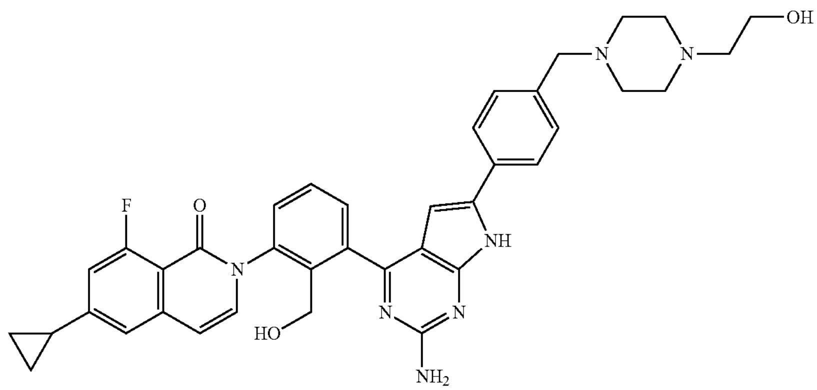 [SMILES: Nc1nc(-c2cccc(-n3ccc4cc(C5CC5)cc(F)c4c3=O)c2CO)c2cc(-c3ccc(CN4CCN(CCO)CC4)cc3)[nH]c2n1] | 2-{3-[2-amino-6-(4-{[4-(2-hydroxy-ethyl)piperazin-1-yl]methyl}phenyl)-7H-pyrrolo[2,3-d]pyrimidin-4-yl]-2-(hydroxy-methyl)phenyl}-6-cyclopropyl-8-fluoroisoquinolin-1(2H)-one |
| 62 | 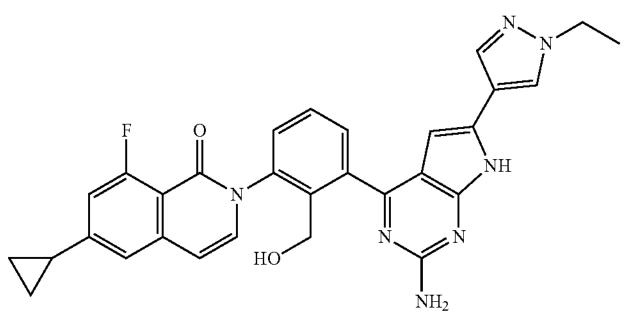 [SMILES: CCn1cc(-c2cc3c(-c4cccc(-n5ccc6cc(C7CC7)cc(F)c6c5=O)c4CO)nc(N)nc3[nH]2)cn1] | 2-{3-[2-amino-6-(1-ethyl-1H-pyrazol-4-yl)-7H-pyrrolo[2,3-d]pyrimidin-4-yl]-2-(hydroxy-methyl)phenyl}-6-cyclopropyl-8-fluoroisoquinolin-1(2H)-one |
| 63 | 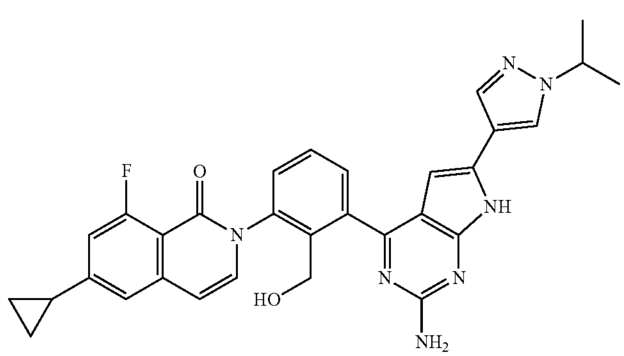 [SMILES: CC(C)n1cc(-c2cc3c(-c4cccc(-n5ccc6cc(C7CC7)cc(F)c6c5=O)c4CO)nc(N)nc3[nH]2)cn1] | 2-{3-[2-amino-6-(1-isopropyl-1H-pyrazol-4-yl)-7H-pyrrolo[2,3-d]pyrimidin-4-yl]-2-(hydroxy-methyl)phenyl}-6-cyclopropyl-8-fluoroisoquinolin-1(2H)-one |

TABLE 1-2-continued

| Example | Structure | Name |
|---|---|---|
| 64 | 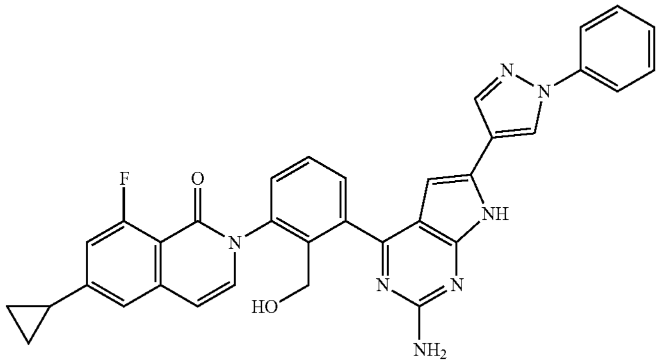 [SMILES: Nc1nc(-c2cccc(-n3ccc4cc(C5CC5)cc(F)c4c3=O)c2CO)c2cc(-c3cnn(-c4ccccc4)c3)[nH]c2n1] | 2-{3-[2-amino-6-(1-phenyl-1H-pyrazol-4-yl)-7H-pyrrolo[2,3-d]pyrimidin-4-yl]-2-(hydroxymethyl)phenyl}-6-cyclopropyl-8-fluoroisoquinolin-1(2H)-one |
| 65 | 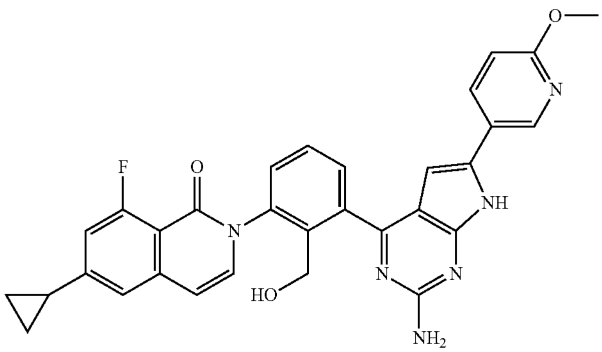 [SMILES: COc1ccc(-c2cc3c(-c4cccc(-n5ccc6cc(C7CC7)cc(F)c6c5=O)c4CO)nc(N)nc3[nH]2)cn1] | 2-{3-[2-amino-6-(6-methoxypyridin-3-yl)-7H-pyrrolo[2,3-d]pyrimidin-4-yl]-2-(hydroxymethyl)phenyl}-6-cyclopropyl-8-fluoroisoquinolin-1(2H)-one |
| 66 | 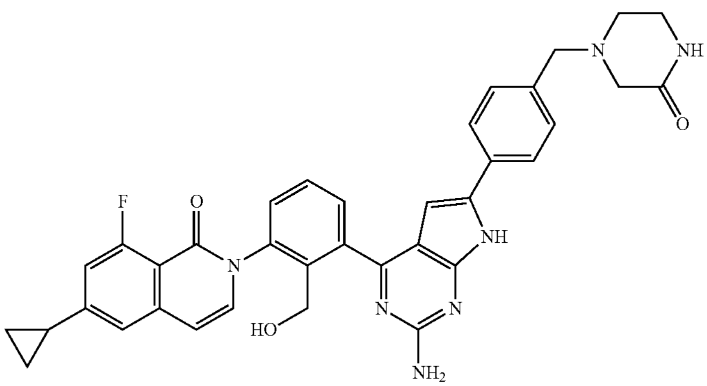 [SMILES: Nc1nc(-c2cccc(-n3ccc4cc(C5CC5)cc(F)c4c3=O)c2CO)c2cc(-c3ccc(CN4CCNC(=O)C4)cc3)[nH]c2n1] | 2-[3-(2-amino-6-{4-[(3-oxopiperazin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one |
| 67 | 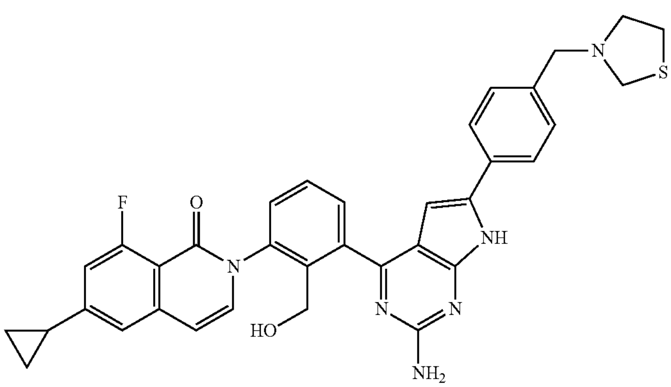 [SMILES: Nc1nc(-c2cccc(-n3ccc4cc(C5CC5)cc(F)c4c3=O)c2CO)c2cc(-c3ccc(CN4CCSC4)cc3)[nH]c2n1] | 2-(3-{2-amino-6-[4-(thiazolidin-3-ylmethyl)phenyl]-7H-pyrrolo[2,3-d]pyrimidin-4-yl}-2-(hydroxymethyl)phenyl)-6-cyclopropyl-8-fluoroisoquinolin-1(2H)-one |

TABLE 1-2-continued

| Example | Structure | Name |
|---|---|---|
| 68 | 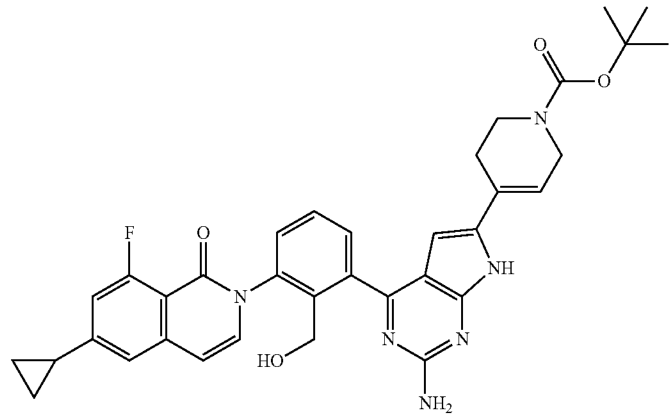 [SMILES: CC(C)(C)OC(=O)N1CC=C(c2cc3c(-c4cccc(-n5ccc6cc(C7CC7)cc(F)c6c5=O)c4CO)nc(N)nc3[nH]2)CC1] | tert-butyl 4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}-5,6-dihydropyridine-1(2H)-carboxylate |
| 69 | 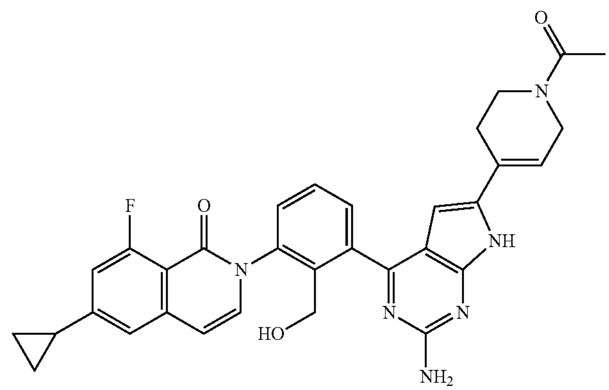 [SMILES: CC(=O)N1CC=C(c2cc3c(-c4cccc(-n5ccc6cc(C7CC7)cc(F)c6c5=O)c4CO)nc(N)nc3[nH]2)CC1] | 2-{3-[6-(1-acetyl-1,2,3,6-tetrahydropyridin-4-yl)-2-amino-7H-pyrrolo[2,3-d]pyrimidin-4-yl]-2-(hydroxymethyl)phenyl}-6-cyclopropyl-8-fluoroisoquinolin-1(2H)-one |
| 70 | 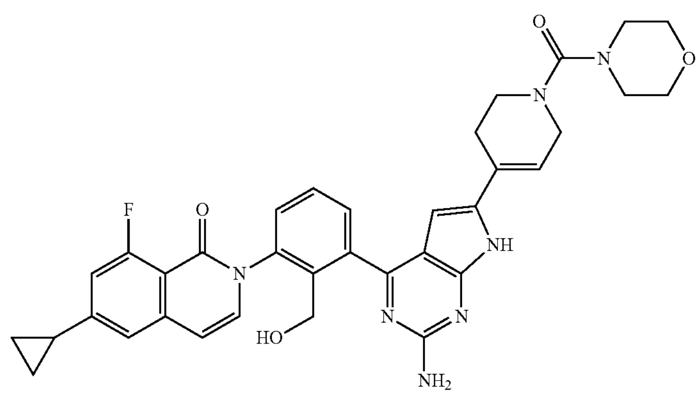 [SMILES: Nc1nc(-c2cccc(-n3ccc4cc(C5CC5)cc(F)c4c3=O)c2CO)c2cc(C3=CCN(C(=O)N4CCOCC4)CC3)[nH]c2n1] | 2-(3-{2-amino-6-[1-(morpholine-4-carbonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one |
| 71 | 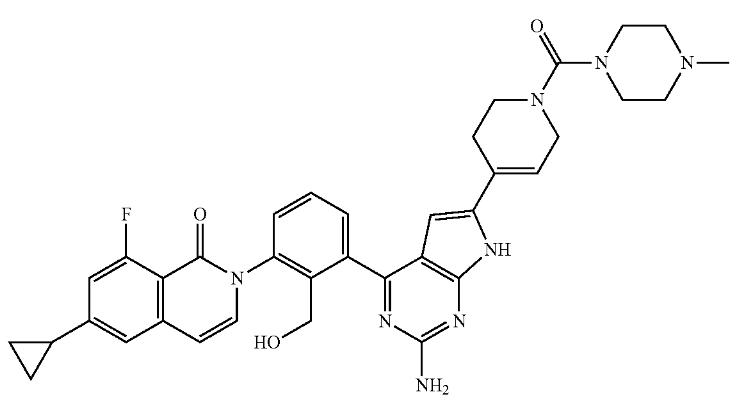 [SMILES: CN1CCN(C(=O)N2CC=C(c3cc4c(-c5cccc(-n6ccc7cc(C8CC8)cc(F)c7c6=O)c5CO)nc(N)nc4[nH]3)CC2)CC1] | 2-(3-{2-amino-6-[1-(4-methylpiperazine-1-carbonyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one |

TABLE 1-2-continued

| Example | Structure | Name |
|---|---|---|
| 72 | 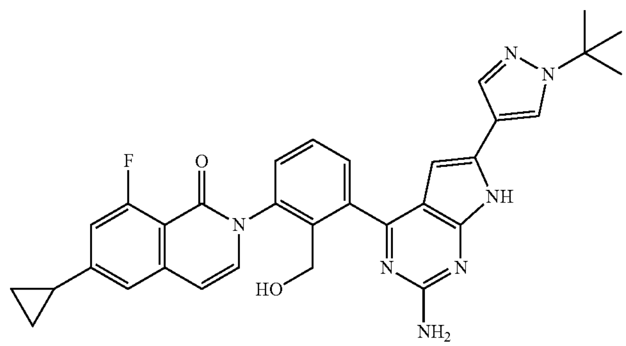 [SMILES: CC(C)(C)n1cc(-c2cc3c(-c4cccc(-n5ccc6cc(C7CC7)cc(F)c6c5=O)c4CO)nc(N)nc3[nH]2)cn1] | 2-(3-{2-amino-6-[1-(tert-butyl)-1H-pyrazol-4-yl]-7H-pyrrolo[2,3-d]pyrimidin-4-yl}-2-(hydroxymethyl)phenyl)-6-cyclopropyl-8-fluoroisoquinolin-1(2H)-one |
| 73 | 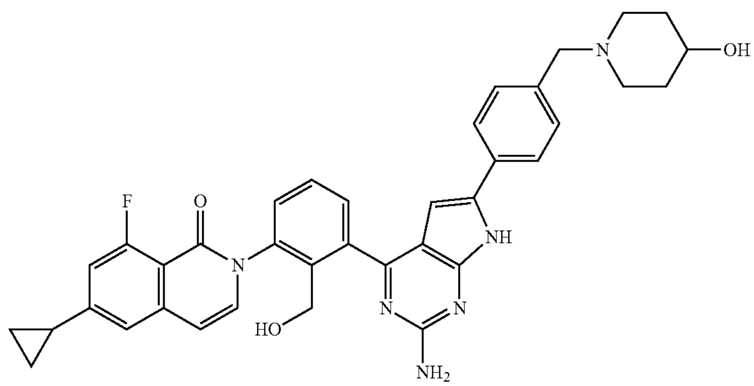 [SMILES: Nc1nc(-c2cccc(-n3ccc4cc(C5CC5)cc(F)c4c3=O)c2CO)c2cc(-c3ccc(CN4CCC(O)CC4)cc3)[nH]c2n1] | 2-[3-(2-amino-6-{4-[(4-hydroxypiperidin-1-yl)methyl]pheny}-7H-pyrrolo[2,3-d]pyrimidin-4-yl)-2-(hydroxymethyl)phenyl]-6-cyclopropyl-8-fluoroisoquinolin-1(2H)-one |
| 74 | 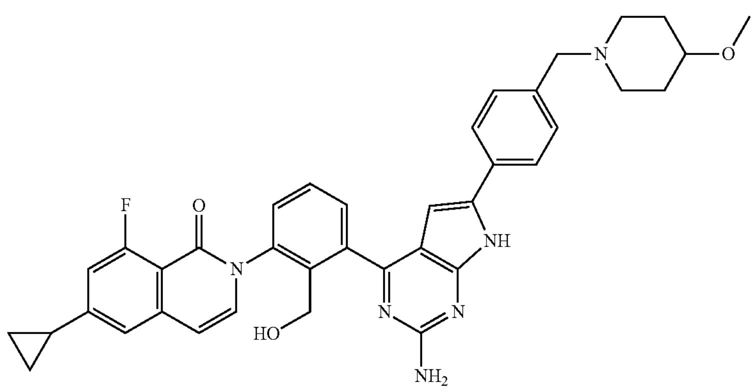 [SMILES: COC1CCN(Cc2ccc(-c3cc4c(-c5cccc(-n6ccc7cc(C8CC8)cc(F)c7c6=O)c5CO)nc(N)nc4[nH]3)cc2)CC1] | 2-[3-(2-amino-6-{4-[(4-methoxypiperidin-1-yl)methyl]pheny}-7H-pyrrolo[2,3-d]pyrimidin-4-yl)-2-(hydroxymethyl)phenyl]-6-cyclopropyl-8-fluoroisoquinolin-1(2H)-one |
| 75 | 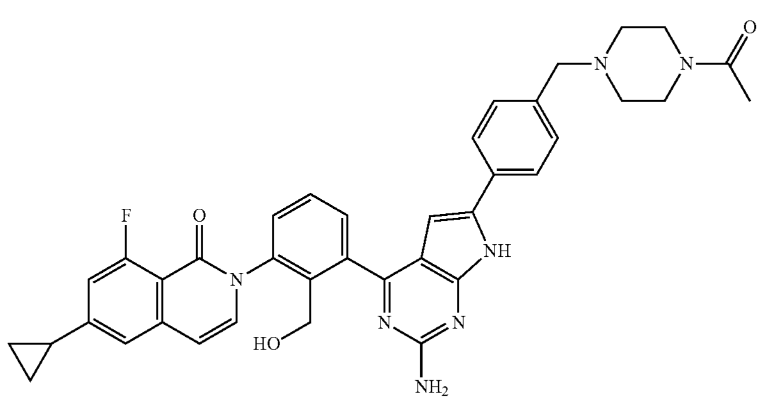 [SMILES: CC(=O)N1CCN(Cc2ccc(-c3cc4c(-c5cccc(-n6ccc7cc(C8CC8)cc(F)c7c6=O)c5CO)nc(N)nc4[nH]3)cc2)CC1] | 2-[3-(6-{4-[(4-acetylpiperazin-1-yl)methyl]pheny}-2-amino-7H-pyrrolo[2,3-d]pyrimidin-4-yl)-2-(hydroxymethyl)phenyl]-6-cyclopropyl-8-fluoroisoquinolin-1(2H)-one |

TABLE 1-2-continued

| Example | Structure | Name |
|---|---|---|
| 76 | 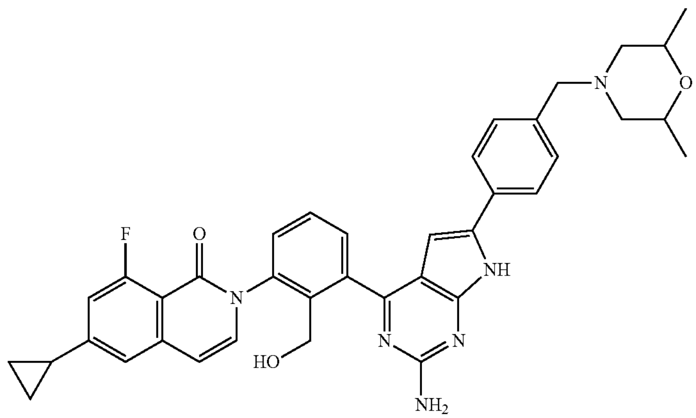 [SMILES: CC1CN(Cc2ccc(-c3cc4c(-c5cccc(-n6ccc7cc(C8CC8)cc(F)c7c6=O)c5CO)nc(N)nc4[nH]3)cc2)CC(C)O1] | 2-[3-(2-amino-6-{4-[(2,6-dimethyl-morpholino)methyl]pheny}-7H-pyrrolo[2,3-d]pyrimidin-4-yl)-2-(hydroxy-methyl)phenyl]-6-cyclopropyl-8-fluoroisoquinolin-1(2H)-one |
| 77 | 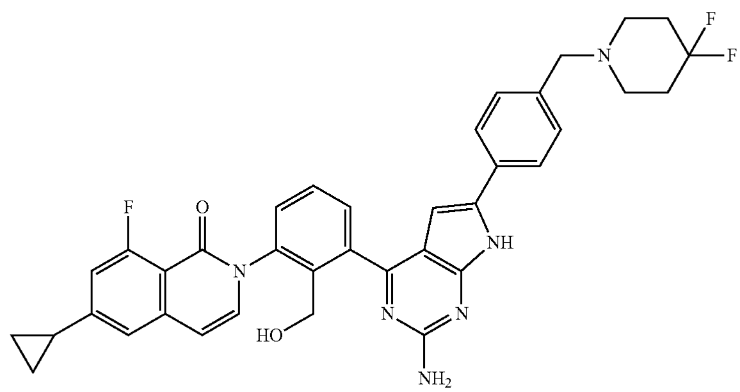 [SMILES: Nc1nc(-c2cccc(-n3ccc4cc(C5CC5)cc(F)c4c3=O)c2CO)c2cc(-c3ccc(CN4CCC(F)(F)CC4)cc3)[nH]c2n1] | 2-[3-(2-amino-6-{4-[(4,4-difluoropiperidin-1-yl)methyl]phenyl}-7H-pyrrolo[2,3-d]pyrimidin-4-yl)-2-(hydroxy-methyl)phenyl]-6-cyclopropyl-8-fluoroisoquinolin-1(2H)-one |
| 78 | 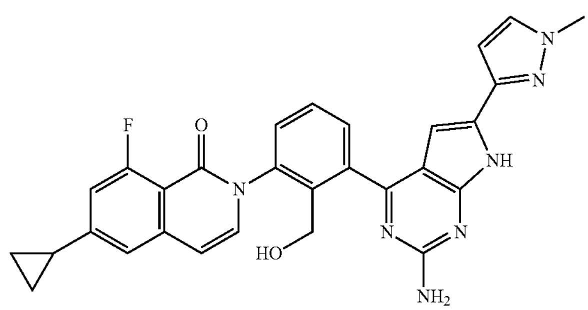 [SMILES: Cn1ccc(-c2cc3c(-c4cccc(-n5ccc6cc(C7CC7)cc(F)c6c5=O)c4CO)nc(N)nc3[nH]2)n1] | 2-{3-[2-amino-6-(1-methyl-1H-pyrazol-3-yl)-7H-pyrrolo[2,3-d]pyrimidin-4-yl]-2-(hydroxy-methyl)phenyl}-6-cyclopropyl-8-fluoroisoquinolin-1(2H)-one |
| 79 | 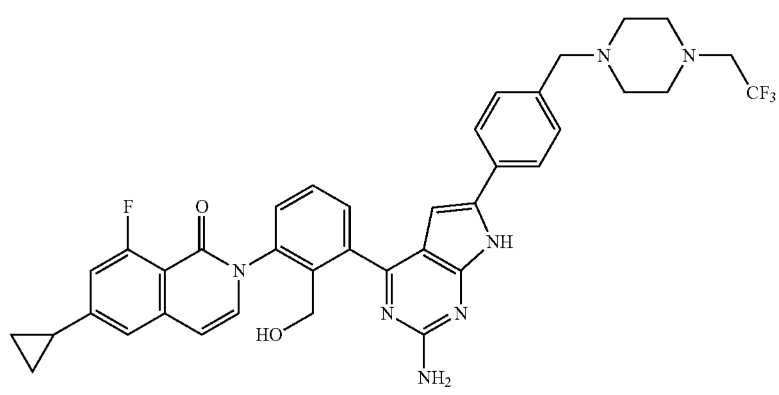 [SMILES: Nc1nc(-c2cccc(-n3ccc4cc(C5CC5)cc(F)c4c3=O)c2CO)c2cc(-c3ccc(CN4CCN(CC(F)(F)F)CC4)cc3)[nH]c2n1] | 2-{3-[2-amino-6-(4-{[4-(2,2,2-trifluoro-ethyl)piperazin-1-yl]methyl}phenyl)-7H-pyrrolo[2,3-d]pyrimidin-4-yl]-2-(hydroxy-methyl)phenyl}-6-cyclopropyl-8-fluoroisoquinolin-1(2H)-one |

TABLE 1-2-continued

| Example | Structure | Name |
|---|---|---|
| 80 | 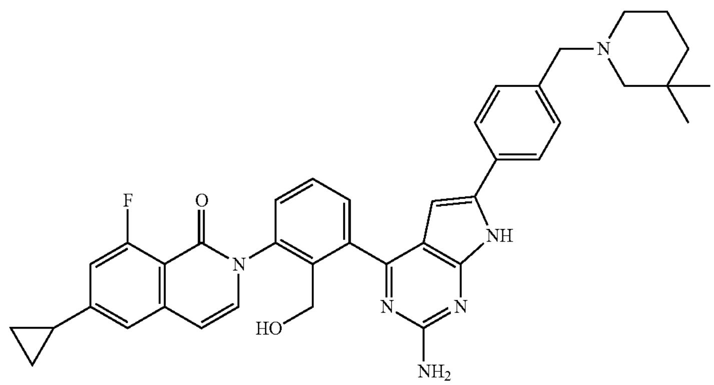 [SMILES: CC1(C)CCCN(Cc2ccc(-c3cc4c(-c5cccc(-n6ccc7cc(C8CC8)cc(F)c7c6=O)c5CO)nc(N)nc4[nH]3)cc2)C1] | 2-[3-(2-amino-6-{4-[(3,3-dimethylpiperidin-1-yl)methyl]phenyl}-7H-pyrrolo[2,3-d]pyrimidin-4-yl)-2-(hydroxymethyl)phenyl]-6-cyclopropyl-8-fluoroisoquinolin-1(2H)-one |
| 81 | 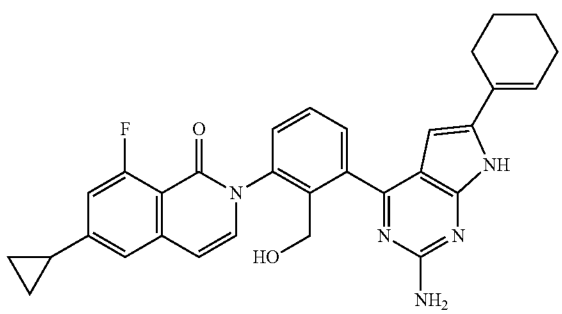 [SMILES: Nc1nc(-c2cccc(-n3ccc4cc(C5CC5)cc(F)c4c3=O)c2CO)c2cc(C3=CCCCC3)[nH]c2n1] | 2-{3-[2-amino-6-(cyclohex-1-en-1-yl)-7H-pyrrolo[2,3-d]pyrimidin-4-yl]-2-(hydroxymethyl)phenyl}-6-cyclopropyl-8-fluoroisoquinolin-1(2H)-one |
| 82 | 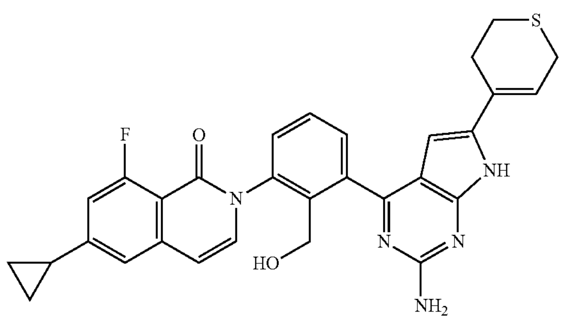 | 2-{3-[2-amino-6-(3,6-dihydro-2H-thiopyran-4-yl)-7H-pyrrolo[2,3-d]pyrimidin-4-yl]-2-(hydroxymethyl)phenyl}-6-cyclopropyl-8-fluoroisoquinolin-1(2H)-one |
| 83 | 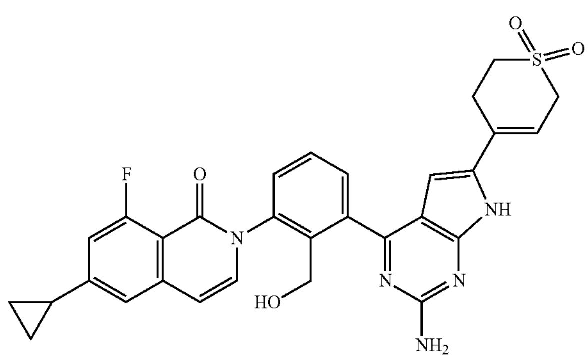 [SMILES: Nc1nc(-c2cccc(-n3ccc4cc(C5CC5)cc(F)c4c3=O)c2CO)c2cc(C3=CCS(=O)(=O)CC3)[nH]c2n1] | 2-{3-[2-amino-6-(1,1-dioxido-3,6-dihydro-2H-thiopyran-4-yl)-7H-pyrrolo[2,3-d]pyrimidin-4-yl]-2-(hydroxymethyl)phenyl}-6-cyclopropyl-8-fluoroisoquinolin-1(2H)-one |

TABLE 1-2-continued

| Example | Structure | Name |
|---|---|---|
| 84 | 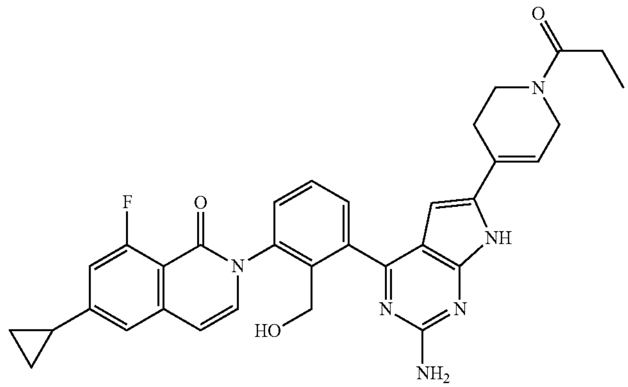 | 2-{3-[2-amino-6-(1-propionyl-1,2,3,6-tetrahydropyridin-4-yl)-7H-pyrrolo[2,3-d]pyrimidin-4-yl]-2-(hydroxymethyl)phenyl}-6-cyclopropyl-8-fluoroisoquinolin-1(2H)-one |
| 85 | 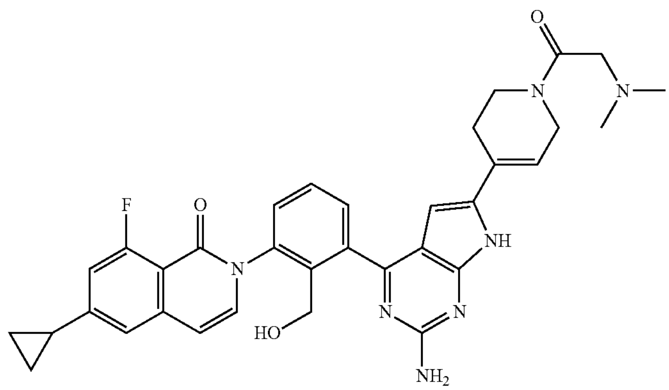 [SMILES: CN(C)CC(=O)N1CC=C(c2cc3c(-c4cccc(-n5ccc6cc(C7CC7)cc(F)c6c5=O)c4CO)nc(N)nc3[nH]2)CC1] | 2-[3-(2-amino-6-{1-[2-(dimethylamino)acetyl]-1,2,3,6-tetrahydropyridin-4-yl}-7H-pyrrolo[2,3-d]pyrimidin-4-yl)-2-(hydroxymethyl)phenyl]-6-cyclopropyl-8-fluoroisoquinolin-1(2H)-one |
| 86 | 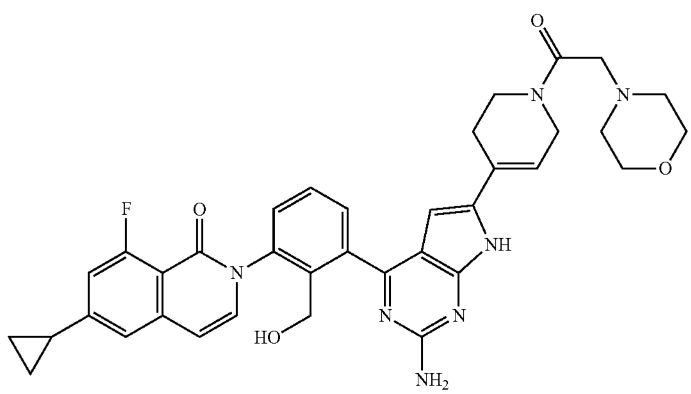 [SMILES: Nc1nc(-c2cccc(-n3ccc4cc(C5CC5)cc(F)c4c3=O)c2CO)c2cc(C3=CCN(C(=O)CN4CCOCC4)CC3)[nH]c2n1] | 2-(3-{2-amino-6-[1-(2-morpholinoacetyl)-1,2,3,6-tetrahydropyridin-4-yl]-7H-pyrrolo[2,3-d]pyrimidin-4-yl}-2-(hydroxymethyl)phenyl)-6-cyclopropyl-8-fluoroisoquinolin-1(2H)-one |
| 87 | 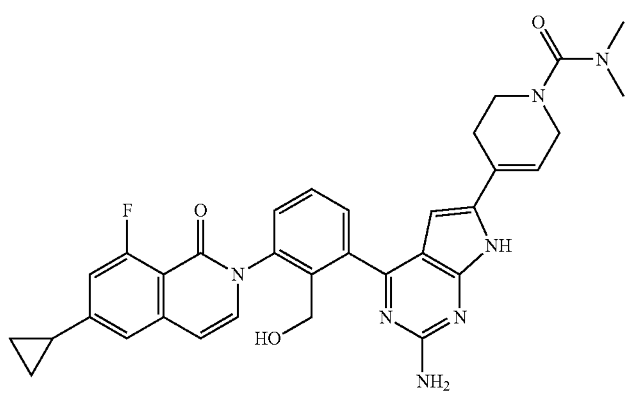 [SMILES: CN(C)C(=O)N1CC=C(c2cc3c(-c4cccc(-n5ccc6cc(C7CC7)cc(F)c6c5=O)c4CO)nc(N)nc3[nH]2)CC1] | 4-{2-amino-4-[3-(6-cyclopropyl-8-fluoro-1-oxoisoquinolin-2(1H)-yl)-2-(hydroxymethyl)phenyl]-7H-pyrrolo[2,3-d]pyrimidin-6-yl}-N,N-dimethyl-5,6-dihydropyridine-1(2H)-carboxamide |

TABLE 1-2-continued

| Example | Structure | Name |
|---|---|---|
| 88 | 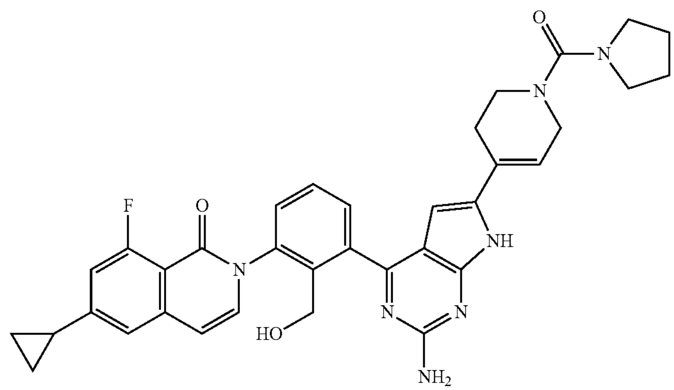 [SMILES: Nc1nc(-c2cccc(-n3ccc4cc(C5CC5)cc(F)c4c3=O)c2CO)c2cc(C3=CCN(C(=O)N4CCCC4)CC3)[nH]c2n1] | 2-(3-{2-amino-6-[1-(pyrrolidine-1-carbonyl)-1,2,3,6-tetrahydropyridin-4-yl]-7H-pyrrolo[2,3-d]pyrimidin-4-yl}-2-(hydroxy-methyl)phenyl)-6-cyclopropyl-8-fluoroisoquinolin-1(2H)-one |
| 89 | 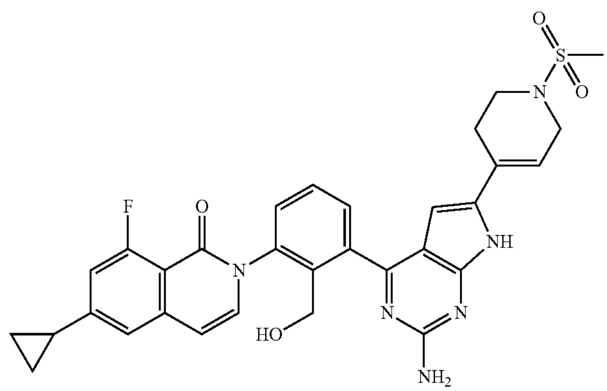 [SMILES: CS(=O)(=O)N1CC=C(c2cc3c(-c4cccc(-n5ccc6cc(C7CC7)cc(F)c6c5=O)c4CO)nc(N)nc3[nH]2)CC1] | 2-(3-{2-amino-6-[1-(methylsulfonyl)-1,2,3,6-tetrahydropyridin-4-yl]-7H-pyrrolo[2,3-d]pyrimidin-4-yl}-2-(hydroxy-methyl)phenyl)-6-cyclopropyl-8-fluoroisoquinolin-1(2H)-one |
| 90 | 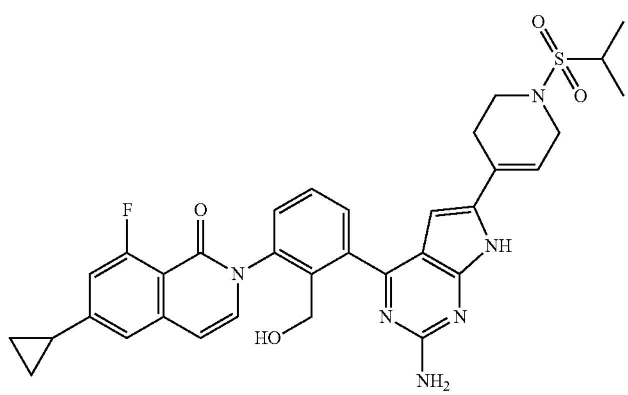 [SMILES: CC(C)S(=O)(=O)N1CC=C(c2cc3c(-c4cccc(-n5ccc6cc(C7CC7)cc(F)c6c5=O)c4CO)nc(N)nc3[nH]2)CC1] | 2-(3-{2-amino-6-[1-(isopropylsulfonyl)-1,2,3,6-tetrahydropyridin-4-yl]-7H-pyrrolo[2,3-d]pyrimidin-4-yl}-2-(hydroxy-methyl)phenyl)-6-cyclopropyl-8-fluoroisoquinolin-1(2H)-one |
| 91 | 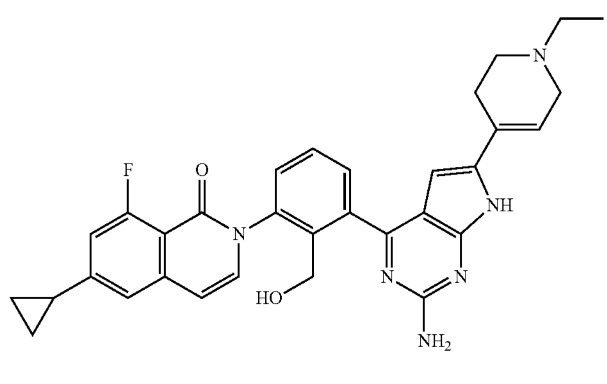 [SMILES: CCN1CC=C(c2cc3c(-c4cccc(-n5ccc6cc(C7CC7)cc(F)c6c5=O)c4CO)nc(N)nc3[nH]2)CC1] | 2-{3-[2-amino-6-(1-ethyl-1,2,3,6-tetrahydropyridin-4-yl)-7H-pyrrolo[2,3-d]pyrimidin-4-yl]-2-(hydroxy-methyl)phenyl}-6-cyclopropyl-8-fluoroisoquinolin-1(2H)-one |

TABLE 1-2-continued

| Example | Structure | Name |
|---|---|---|
| 92 | 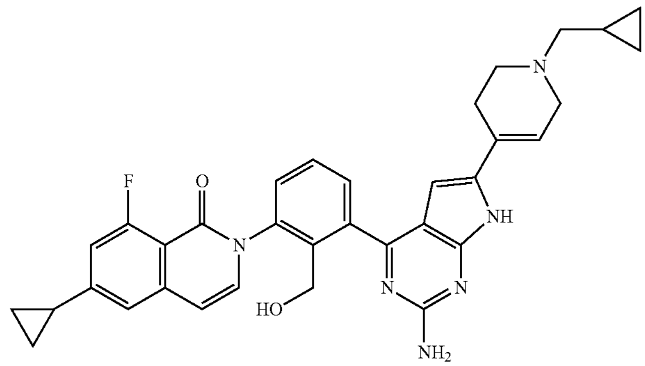 [SMILES: Nc1nc(-c2cccc(-n3ccc4cc(C5CC5)cc(F)c4c3=O)c2CO)c2cc(C3=CCN(CC4CC4)CC3)[nH]c2n1] | 2-(3-{2-amino-6-[1-(cyclopropylmethyl)-1,2,3,6-tetrahydropyridin-4-yl]-7H-pyrrolo[2,3-d]pyrimidin-4-yl}-2-(hydroxy-methyl)phenyl)-6-cyclopropyl-8-fluoroisoquinolin-1(2H)-one |
| 93 | 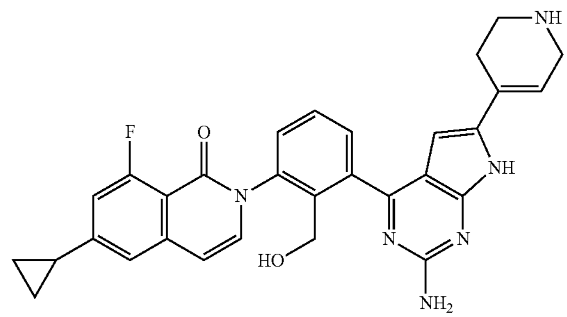 [SMILES: Nc1nc(-c2cccc(-n3ccc4cc(C5CC5)cc(F)c4c3=O)c2CO)c2cc(C3=CCNCC3)[nH]c2n1] | 2-{3-[2-amino-6-(1,2,3,6-tetrahydropyridin-4-yl)-7H-pyrrolo[2,3-d]pyrimidin-4-yl]-2-(hydroxy-methyl)phenyl}-6-cyclopropyl-8-fluoroisoquinolin-1(2H)-one |

TABLE 2-1

| Examples | $^1$H-NMR δ (ppm) | LCMS m/z [M + H]$^+$ |
|---|---|---|
| 4 | (DMSO-d6) 12.80 (s, 1H), 8.13 (s, 1H), 7.87 (dd, J = 7.8, 1.4 Hz, 1H), 7.64-7.55 (m, 1H), 7.47 (dd, J = 7.9, 1.4 Hz, 1H), 7.37 (d, J = 7.4 Hz, 1H), 7.28 (d, J = 1.6 Hz, 1H), 6.99 (dd, J = 13.3, 1.7 Hz, 1H), 6.65-6.58 (m, 3H), 5.43-5.35 (m, 1H), 4.36-4.27 (m, 1H), 4.14-4.04 (m, 1H), 2.14-2.02 (m, 1H), 1.16-1.03 (m, 2H), 0.92-0.81 (m, 2H). | 443.2 |
| 5 | (DMSO-d6) 13.12 (s, 1H), 7.91-7.84 (m, 1H), 7.75 (dd, J = 7.8, 1.4 Hz, 1H), 7.69-7.59 (m, 1H), 7.58-7.46 (m, 1H), 7.44-7.35 (m, 1H), 7.31-7.23 (m, 1H), 7.04-6.89 (m, 3H), 6.62 (dd, J = 7.5, 2.1 Hz, 1H), 4.89-4.77 (m, 1H), 4.45-4.34 (m, 1H), 4.17-4.07 (m, 1H), 2.14-2.02 (m, 1H), 1.15-1.04 (m, 2H), 0.92-0.82 (m, 2H). | 443.1 |
| 6 | (DMSO-d6) 11.40-11.34 (m, 1H), 7.72 (dd, J = 7.8, 1.4 Hz, 1H), 7.64-7.55 (m, 1H), 7.46 (dd, J = 7.9, 1.3 Hz, 1H), 7.37 (d, J = 7.4 Hz, 1H), 7.31-7.23 (m, 1H), 7.13 (dd, J = 3.6, 2.2 Hz, 1H), 7.00 (dd, J = 13.2, 1.7 Hz, 1H), 6.62 (dd, J = 7.5, 2.1 Hz, 1H), 6.36 (s, 2H), 6.25 (dd, J = 3.6, 1.8 Hz, 1H), 5.22-5.13 (m, 1H), 4.30-4.21 (m, 1H), 4.11-4.00 (m, 1H), 2.14-2.02 (m, 1H), 1.16-1.01 (m, 2H), 0.92-0.80 (m, 2H). | 442.0 |
| 7 | (DMSO-d6) 11.23 (s, 1H), 7.69 (dd, J = 1.0, 7.8 Hz, 1H), 7.57 (t, J = 7.6 Hz, 1H), 7.44 (dd, J = 1.0, 7.8 Hz, 1H), 7.35 (d, J = 7.3 Hz, 1H), 7.27 (d, J = 1.5 Hz, 1H), 7.00 (dd, J = 1.5, 13.2 Hz, 1H), 6.61 (dd, J = 2.0, 7.3 Hz, 1H), 6.22 (s, 2H), 5.95 (s, 1H), 5.28 (dd, J = 4.4, 9.3 Hz, 1H), 4.21 (dd, J = 4.4, 11.7 Hz, 1H), 4.03 (dd, J = 8.8, 11.7 Hz, 1H), 2.29 (s, 3H), 2.13-2.03 (m, 1H), 1.11-1.07 (m, 2H), 0.89-0.85 (m, 2H). | 456.3 |
| 8 | (DMSO-d6) 11.86 (d, J = 1.5 Hz, 1H), 7.81-7.77 (m, 3H), 7.62 (t, J = 7.8 Hz, 1H), 7.48 (dd, J = 1.0, 7.8 Hz, 1H), 7.38 (d, J = 7.3 Hz, 1H), 7.32 (d, J = 8.3 Hz, 2H), 7.28 (d, J = 1.5 Hz, 1H), 7.00 (dd, J = 1.5, 13.2 Hz, 1H), 6.72 (d, J = 2.0 Hz, 1H), 6.63 (dd, J = 2.0, 7.8 Hz, 1H), 6.44 (s, 2H), 5.17 (dd, J = 4.9, 8.8 Hz, 1H), 4.29 (dd, J = 4.4, 11.7 Hz, 1H), 4.08 (dd, J = 9.0, 12.0 Hz, 1H), 3.46 (s, 2H), 2.43-2.23 (m, 8H), 2.14 (s, 3H), 2.09-2.07 (m, 1H), 1.11-1.07 (m, 2H), 0.89-0.85 (m, 2H). | 630.3 |
| 9 | (DMSO-d6) 11.25 (s, 1H), 7.68 (d, J = 6.8 Hz, 1H), 7.57 (t, J = 7.8 Hz, 1H), 7.43 (d, J = 7.8 Hz, 1H), 7.35 (d, J = 7.3 Hz, 1H), 7.27 (s, 1H), 6.99 (d, J = 13.2 Hz, 1H), 6.62 (dd, J = 2.0, | 482.4 |

TABLE 2-1-continued

| Examples | ¹H-NMR δ (ppm) | LCMS m/z [M + H]⁺ |
|---|---|---|
| | 7.3 Hz, 1H), 6.21 (s, 2H), 5.92 (d, J = 1.5 Hz, 1H), 5.28 (dd, J = 4.4, 8.8 Hz, 1H), 4.20 (dd, J = 4.2, 12.0 Hz, 1H), 4.02 (dd, J = 9.3, 11.7 Hz, 1H), 2.09-2.05 (m, 1H), 1.95-1.91 (m, 1H), 1.12-1.07 (m, 2H), 0.92-0.85 (m, 4H), 0.81-0.77 (m, 2H). | |
| 10 | (500 MHz, DMSO-d6) 12.64 (br. s, 1H), 7.59-7.56 (m, 1H), 7.47 (dd, J = 7.6, 13.7 Hz, 2H), 7.33 (d, J = 7.3 Hz, 1H), 7.26 (s, 1H), 6.98 (d, J = 12.8 Hz, 1H), 6.79 (br. s, 2H), 6.60 (d, J = 6.1 Hz, 1H), 4.58 (t, J = 5.3 Hz, 1H), 4.22 (br. s, 1H), 4.11 (dd, J = 6.6, 11.7 Hz, 1H), 2.08-2.05 (m, 1H), 1.96 (s, 3H), 1.11-1.07 (m, 2H), 0.88-0.86 (m, 2H) | 457.3 |
| 11 | (500 MHz, DMSO-d6) 8.08-7.99 (m, 1H), 7.33-7.32 (m, 1H), 7.17-7.16 (m, 1H), 7.06-7.05 (m, 2H), 6.83-6.78 (m, 3H), 4.83-4.81 (m, 3H), 4.32 (s, 2H), 4.13-4.10 (m, 1H), 1.95-1.89 (m, 1H), 0.94-0.93 (m, 2H), 0.71-0.68 (m, 2H). | 470.5 |
| 12 | (500 MHz, DMSO-d6) 12.59 (br. s, 1H), 7.78 (d, J = 7.3 Hz, 1H), 7.57 (t, J = 7.6 Hz, 1H), 7.44 (d, J = 7.3 Hz, 1H), 7.36 (d, J = 7.3 Hz, 1H), 7.27 (s, 1H), 6.99 (d, J = 13.1 Hz, 1H), 6.60 (d, J = 6.4 Hz, 1H), 6.44 (br. s, 2H), 5.67 (br. s, 1H), 4.24-4.01 (m, 2H), 2.09-2.04 (m, 2H), 1.11-0.98 (m, 6H), 0.89-0.87 (m, 2H). | 483.4 |
| 13 | (DMSO-d6) 11.67 (s, 1H), 8.10 (s, 1H), 7.90 (s, 1H), 7.75 (d, J = 7.6 Hz, 1H), 7.61 (t, J = 7.8 Hz, 1H), 7.46 (d, J = 7.8 Hz, 1H), 7.36 (d, J = 7.4 Hz, 1H), 7.31-7.25 (m, 1H), 7.04-6.95 (m, 1H), 6.62 (dd, J = 7.4, 2.0 Hz, 1H), 6.41 (s, 1H), 6.32 (s, 2H), 5.22 (dd, J = 8.9, 4.5 Hz, 1H), 4.30-4.21 (m, 1H), 4.11-4.01 (m, 1H), 3.87 (s, 3H), 2.14-2.02 (m, 1H), 1.13-1.03 (m, 2H), 0.94-0.81 (m, 2H). | 522.4 |
| 14 | (DMSO-d6) 11.55 (s, 1H), 7.82-7.70 (m, 2H), 7.67-7.56 (m, 1H), 7.48 (dd, J = 7.8, 1.4 Hz, 1H), 7.44-7.26 (m, 3H), 7.13 (d, J = 8.3 Hz, 1H), 7.07-6.95 (m, 2H), 6.79 (s, 1H), 6.63 (dd, J = 7.4, 2.1 Hz, 1H), 6.40 (s, 2H), 5.17 (s, 1H), 4.34-4.26 (m, 1H), 4.15-4.05 (m, 1H), 3.89 (s, 3H), 2.14-2.02 (m, 1H), 1.15-1.04 (m, 2H), 0.95-0.81 (m, 2H). | 548.5 |
| 15 | (DMSO-d6) 11.89 (s, 1H), 7.79 (dd, J = 7.7, 1.4 Hz, 1H), 7.63 (t, J = 7.8 Hz, 1H), 7.52-7.25 (m, 6H), 7.00 (dd, J = 13.2, 1.6 Hz, 1H), 6.90-6.82 (m, 1H), 6.79 (d, J = 2.0 Hz, 1H), 6.63 (dd, J = 7.4, 2.1 Hz, 1H), 6.45 (s, 2H), 5.15 (dd, J = 8.8, 4.5 Hz, 1H), 4.34-4.25 (m, 1H), 4.14-4.03 (m, 1H), 3.82 (s, 3H), 2.14-2.02 (m, 1H), 1.15-1.03 (m, 2H), 0.95-0.81 (m, 2H). | 548.2 |
| 16 | (DMSO-d6) 11.81 (s, 1H), 7.89-7.71 (m, 3H), 7.62 (t, J = 7.8 Hz, 1H), 7.47 (dd, J = 7.9, 1.3 Hz, 1H), 7.38 (d, J = 7.4 Hz, 1H), 7.28 (d, J = 1.7 Hz, 1H), 7.07-6.91 (m, 3H), 6.70-6.54 (m, 2H), 6.39 (s, 2H), 5.22 (s, 1H), 4.32-4.24 (m, 1H), 4.12-4.02 (m, 1H), 3.79 (s, 3H), 2.14-2.02 (m, 1H), 1.15-1.01 (m, 2H), 0.92-0.81 (m, 2H). | 548.5 |
| 17 | (DMSO-d6) 11.99 (s, 1H), 9.09-9.04 (m, 1H), 8.49-8.43 (m, 1H), 8.20 (d, J = 8.0 Hz, 1H), 7.77 (d, J = 7.6 Hz, 1H), 7.61 (t, J = 7.8 Hz, 1H), 7.51-7.31 (m, 3H), 7.26 (s, 1H), 6.98 (d, J = 13.2 Hz, 1H), 6.91 (s, 1H), 6.61 (dd, J = 7.6, 2.0 Hz, 1H), 6.51 (s, 2H), 5.07 (dd, J = 8.6, 4.6 Hz, 1H), 4.29 (dd, J = 12.1, 4.4 Hz, 1H), 4.07 (dd, J = 12.0, 8.7 Hz, 1H), 2.12-2.01 (m, 1H), 1.13-1.03 (m, 2H), 0.90-0.79 (m, 2H). | 519.2 |
| 18 | (DMSO-d6) 7.85 (d, J = 7.7 Hz, 1H), 7.69-7.55 (m, 3H), 7.48-7.33 (m, 3H), 7.31-7.25 (m, 1H), 7.03-6.94 (m, 2H), 6.63 (dd, J = 7.5, 2.0 Hz, 1H), 6.23 (br. s, 3H), 4.34-4.26 (m, 1H), 4.11-4.03 (m, 1H), 3.82 (s, 3H), 2.14-2.03 (m, 1H), 1.15-1.03 (m, 2H), 0.92-0.80 (m, 2H). | 549.5 |
| 19 | (DMSO-d6) 12.09 (s, 1H), 8.56 (d, J = 5.2 Hz, 2H), 7.86-7.74 (m, 3H), 7.63 (t, J = 7.8 Hz, 1H), 7.50 (d, J = 7.8 Hz, 1H), 7.38 (d, J = 7.4 Hz, 1H), 7.28 (s, 1H), 7.08 (s, 1H), 7.00 (d, J = 13.2 Hz, 1H), 6.66-6.59 (m, 3H), 5.02 (dd, J = 8.5, 4.6 Hz, 1H), 4.37-4.28 (m, 1H), 4.15-4.04 (m, 1H), 2.14-2.02 (m, 1H), 1.15-1.05 (m, 2H), 0.92-0.81 (m, 2H). | 519.4 |
| 20 | (DMSO-d6) 13.17 (s, 1H), 7.34-7.25 (m, 2H), 7.18-6.93 (m, 6H), 6.91-6.83 (m, 2H), 6.69 (d, J = 8.4 Hz, 2H), 6.61 (dd, J = 7.4, 2.0 Hz, 1H), 4.67 (s, 1H), 4.45-4.40 (m, 1H), 4.14-4.09 (m, 1H), 3.72 (s, 3H), 2.14-2.02 (m, 1H), 1.15-1.03 (m, 2H), 0.92-0.81 (m, 2H). | 549.4 |
| 21 | (DMSO-d6) 13.12 (s, 1H), 7.37 (d, J = 7.4 Hz, 1H), 7.31-7.17 (m, 3H), 7.08 (s, 1H), 7.04-6.84 (m, 6H), 6.62-6.53 (m, 2H), 4.85 (s, 1H), 4.27-4.19 (m, 1H), 4.14-4.04 (m, 1H), 3.19 (s, 3H), 2.14-2.00 (m, 1H), 1.15-1.01 (m, 2H), 0.92-0.78 (m, 2H). | 549.3 |

TABLE 2-1-continued

| Examples | ¹H-NMR δ (ppm) | LCMS m/z [M + H]⁺ |
|---|---|---|
| 22 | (DMSO-d6) 13.17 (s, 1H), 7.32-7.24 (m, 3H), 7.22-6.67 (m, 9H), 6.62 (dd, J = 7.5, 2.0 Hz, 1H), 4.70 (t, J = 5.3 Hz, 1H), 4.63-4.38 (m, 1H), 4.29-3.91 (m, 1H), 3.60 (s, 3H), 2.14-2.02 (m, 1H), 1.15-1.05 (m, 2H), 0.92-0.83 (m, 2H). | 549.3 |

TABLE 2-2

| Examples | ¹H-NMR δ (ppm) | LCMS m/z [M + H]⁺ |
|---|---|---|
| 24 | (DMSO-d6) 12.55 (s, 1H), 7.99-7.88 (m, 2H), 7.66-7.59 (m, 1H), 7.55-7.45 (m, 2H), 7.41 (d, J = 7.4 Hz, 1H), 7.28 (d, J = 1.7 Hz, 1H), 7.21 (d, J = 8.4 Hz, 1H), 7.11-7.03 (m, 1H), 6.99 (dd, J = 13.2, 1.7 Hz, 1H), 6.65-6.58 (m, 3H), 5.65-5.58 (m, 1H), 4.38-4.31 (m, 1H), 4.15-4.06 (m, 1H), 3.94 (s, 3H), 2.13-2.04 (m, 1H), 1.14-1.05 (m, 2H), 0.91-0.82 (m, 2H). | 549.3 |
| 25 | (DMSO-d6) 13.46 (s, 1H), 9.28-9.23 (m, 1H), 8.68 (d, J = 4.7 Hz, 1H), 8.41 (d, J = 8.1 Hz, 1H), 7.93 (d, J = 7.7 Hz, 1H), 7.68-7.47 (m, 3H), 7.41 (d, J = 7.4 Hz, 1H), 7.29 (s, 1H), 7.00 (d, J = 13.1 Hz, 1H), 6.79-6.73 (m, 2H), 6.63 (dd, J = 7.4, 2.0 Hz, 1H), 5.30 (s, 1H), 4.43-4.34 (m, 1H), 4.17-4.07 (m, 1H), 2.14-2.03 (m, 1H), 1.15-1.05 (m, 2H), 0.92-0.83 (m, 2H). | 520.2 |
| 26 | (DMSO-d6) 11.86 (d, J = 2.2 Hz, 1H), 7.88-7.70 (m, 3H), 7.67-7.55 (m, 1H), 7.46 (dd, J = 7.9, 1.3 Hz, 1H), 7.34 (dd, J = 14.3, 7.6 Hz, 3H), 7.27 (d, J = 1.6 Hz, 1H), 6.98 (dd, J = 13.3, 1.8 Hz, 1H), 6.71 (d, J = 2.1 Hz, 1H), 6.61 (dd, J = 7.5, 2.1 Hz, 1H), 6.43 (s, 2H), 5.23-5.06 (m, 1H), 4.37-4.19 (m, 1H), 4.15-3.96 (m, 1H), 3.64-3.49 (m, 4H), 3.46 (s, 2H), 2.43-2.26 (m, 4H), 2.20-1.95 (m, 1H), 1.14-0.98 (m, 2H), 0.96-0.67 (m, 2H). | 617.3 |
| 27 | (DMSO-d6 12.10-12.05 (m, 1H), 8.09-8.00 (m, 2H), 7.89-7.83 (m, 2H), 7.79 (dd, J = 7.8, 1.3 Hz, 1H), 7.69-7.59 (m, 1H), 7.50 (dd, J = 7.9, 1.3 Hz, 1H), 7.38 (d, J = 7.4 Hz, 1H), 7.28 (d, J = 1.7 Hz, 1H), 7.04 (d, J = 2.1 Hz, 1H), 7.00 (dd, J = 13.3, 1.6 Hz, 1H), 6.67-6.59 (m, 3H), 5.10-5.01 (m, 1H), 4.37-4.28 (m, 1H), 4.15-4.05 (m, 1H), 2.14-2.02 (m, 1H), 1.15-1.04 (m, 2H), 0.92-0.82 (m, 2H). | 543.1 |
| 28 | (DMSO-d6) 11.51 (s, 1H), 7.62-6.06 (m, 12H), 5.11-4.72 (m, 1H), 4.51-3.87 (m, 2H), 2.16-1.97 (m, 1H), 1.17-1.01 (m, 2H), 0.99-0.75 (m, 2H). | 518.2 |
| 29 | (DMSO-d6) 11.91-11.86 (m, 1H), 7.96-7.89 (m, 1H), 7.76 (dd, J = 7.7, 1.3 Hz, 1H), 7.67-7.59 (m, 1H), 7.48 (dd, J = 7.8, 1.3 Hz, 1H), 7.41-7.26 (m, 5H), 7.00 (dd, J = 13.2, 1.7 Hz, 1H), 6.72-6.67 (m, 1H), 6.62 (dd, J = 7.5, 2.1 Hz, 1H), 6.53 (s, 2H), 5.10-5.04 (m, 1H), 4.35-4.28 (m, 1H), 4.13-4.05 (m, 1H), 2.13-2.04 (m, 1H), 1.14-1.06 (m, 2H), 0.91-0.84 (m, 2H). | 536.3 |
| 30 | (DMSO-d6) 11.39 (s, 1H), 8.58-8.52 (m, 1H), 7.69-7.62 (m, 1H), 7.63-7.55 (m, 1H), 7.45 (dd, J = 7.8, 1.4 Hz, 1H), 7.36 (d, J = 7.4 Hz, 1H), 7.28 (d, J = 1.6 Hz, 1H), 6.99 (dd, J = 13.2, 1.7 Hz, 1H), 6.61 (dd, J = 7.4, 2.1 Hz, 1H), 6.36-6.23 (m, 3H), 6.17-6.05 (m, 2H), 5.65-5.55 (m, 1H), 5.16 (s, 1H), 4.46-4.34 (m, 2H), 4.30-4.20 (m, 1H), 4.08-4.00 (m, 1H), 2.08 (tt, J = 8.5, 5.0 Hz, 1H), 1.14-1.03 (m, 2H), 0.91-0.82 (m, 2H). | 525.2 |
| 31 | (DMSO-d6) 13.71-12.79 (m, 1H), 8.36 (s, 1H), 8.05 (s, 1H), 7.82 (d, J = 7.7 Hz, 1H), 7.67-7.56 (m, 1H), 7.52 (d, J = 7.9 Hz, 1H), 7.37 (d, J = 7.4 Hz, 1H), 7.29 (s, 1H), 7.00 (d, J = 13.0 Hz, 1H), 6.82 (s, 2H), 6.63 (d, J = 7.4 Hz, 1H), 4.38-4.32 (m, 1H), 4.17-4.11 (m, 1H), 3.92 (s, 3H), 2.08 (tt, J = 8.7, 5.0 Hz, 1H), 1.14-1.03 (m, 2H), 0.93-0.82 (m, 2H). | 523.3 |
| 32 | (DMSO-d6) 11.86 (s, 1H), 7.95-7.88 (m, 1H), 7.77 (dd, J = 7.7, 1.3 Hz, 1H), 7.64-7.61 (m, 3H), 7.48 (dd, J = 7.8, 1.3 Hz, 1H), 7.38 (d, J = 7.4 Hz, 1H), 7.29 (d, J = 1.6 Hz, 1H), 7.00 (dd, J = 13.2, 1.7 Hz, 1H), 6.67-6.59 (m, 2H), 6.45 (s, 2H), 5.22-5.14 (m, 1H), 4.32-4.23 (m, 1H), 4.12-3.99 (m, 1H), 2.14-2.02 (m, 1H), 1.22-1.04 (m, 2H), 0.92-0.82 (m, 2H). | 524.2 |
| 33 | (DMSO-d6) 11.96-11.91 (m, 1H), 7.82-7.67 (m, 3H), 7.67-7.59 (m, 1H), 7.52-7.41 (m, 2H), 7.38 (d, J = 7.3 Hz, 1H), 7.28 (d, J = 1.7 Hz, 1H), 7.15-7.07 (m, 1H), 7.00 | 536.3 |

TABLE 2-2-continued

| Examples | ¹H-NMR δ (ppm) | LCMS m/z [M + H]⁺ |
|---|---|---|
|  | (dd, J = 13.1, 1.7 Hz, 1H), 6.90 (d, J = 2.1 Hz, 1H), 6.63 (dd, J = 7.4, 2.1 Hz, 1H), 6.52 (s, 2H), 5.15-5.08 (m, 1H), 4.34-4.26 (m, 1H), 4.13-4.05 (m, 1H), 2.13-2.04 (m, 1H), 1.14-1.05 (m, 2H), 0.91-0.82 (m, 2H). |  |
| 34 | (DMSO-d6) 11.93-11.88 (m, 1H), 7.96-7.86 (m, 2H), 7.79 (dd, J = 7.7, 1.3 Hz, 1H), 7.66-7.58 (m, 1H), 7.48 (dd, J = 7.8, 1.3 Hz, 1H), 7.38 (d, J = 7.4 Hz, 1H), 7.34-7.22 (m, 3H), 7.00 (dd, J = 13.2, 1.7 Hz, 1H), 6.75 (d, J = 2.1 Hz, 1H), 6.63 (dd, J = 7.6, 2.2 Hz, 1H), 6.46 (s, 2H), 5.20-5.12 (m, 1H), 4.33-4.23 (m, 1H), 4.12-4.04 (m, 1H), 2.18-2.04 (m, 1H), 1.14-1.05 (m, 2H), 0.91-0.82 (m, 2H). | 536.2 |
| 35 | (DMSO-d6) 11.92-11.88 (m, 1H), 8.00-7.92 (m, 1H), 7.76 (dd, J = 7.7, 1.4 Hz, 1H), 7.67-7.60 (m, 1H), 7.52-7.36 (m, 3H), 7.31-7.20 (m, 2H), 7.00 (dd, J = 13.3, 1.7 Hz, 1H), 6.68-6.60 (m, 2H), 6.54 (s, 2H), 5.10-5.04 (m, 1H), 4.35-4.28 (m, 1H), 4.14-4.06 (m, 1H), 2.13-2.04 (m, 1H), 1.15-1.05 (m, 2H), 0.92-0.83 (m, 2H). | 554.4 |
| 36 | (DMSO-d6) 11.94 (s, 1H), 8.02-7.93 (m, 1H), 7.81-7.76 (m, 1H), 7.76-7.69 (m, 1H), 7.66-7.59 (m, 1H), 7.54-7.44 (m, 2H), 7.37 (d, J = 7.4 Hz, 1H), 7.28 (d, J = 1.6 Hz, 1H), 7.00 (dd, J = 13.3, 1.7 Hz, 1H), 6.87 (s, 1H), 6.63 (dd, J = 7.5, 2.0 Hz, 1H), 6.50 (s, 2H), 5.13 (s, 1H), 4.32-4.26 (m, 1H), 4.12-4.04 (m, 1H), 2.13-2.04 (m, 1H), 1.14-1.03 (m, 2H), 0.91-0.84 (m, 2H). | 554.6 |
| 37 | (DMSO-d6) 12.07 (s, 1H), 8.08 (d, J = 8.2 Hz, 2H), 7.83-7.73 (m, 3H), 7.67-7.58 (m, 1H), 7.49 (dd, J = 7.9, 1.3 Hz, 1H), 7.38 (d, J = 7.4 Hz, 1H), 7.28 (d, J = 1.6 Hz, 1H), 7.03-6.94 (m, 2H), 6.63 (dd, J = 7.5, 2.0 Hz, 1H), 6.55 (s, 2H), 5.09 (s, 1H), 4.35-4.28 (m, 1H), 4.13-4.05 (m, 1H), 2.13-2.04 (m, 1H), 1.14-1.05 (m, 2H), 0.91-0.83 (m, 2H). | 586.6 |
| 38 | (DMSO-d6) 12.00-11.96 (m, 1H), 8.02-7.95 (m, 2H), 7.79 (dd, J = 7.6, 1.4 Hz, 1H), 7.67-7.60 (m, 1H), 7.52-7.47 (m, 1H), 7.45-7.36 (m, 3H), 7.29 (d, J = 1.6 Hz, 1H), 7.00 (dd, J = 13.3, 1.7 Hz, 1H), 6.90-6.81 (m, 1H), 6.63 (dd, J = 7.5, 2.2 Hz, 1H), 6.52 (s, 2H), 5.15-5.09 (m, 1H), 4.35-4.27 (m, 1H), 4.14-4.05 (m, 1H), 2.13-2.04 (m, 1H), 1.15-1.04 (m, 2H), 0.92-0.83 (m, 2H). | 602 |
| 39 | (DMSO-d6) 11.21 (s, 1H), 7.69 (d, J = 7.5 Hz, 1H), 7.62-7.55 (m, 1H), 7.45 (dd, J = 7.8, 1.3 Hz, 1H), 7.36 (d, J = 7.4 Hz, 1H), 7.28 (d, J = 1.7 Hz, 1H), 6.99 (dd, J = 13.2, 1.7 Hz, 1H), 6.66-6.59 (m, 1H), 6.27 (s, 2H), 6.09 (s, 1H), 5.28-5.22 (m, 1H), 4.25-4.18 (m, 1H), 4.08-4.00 (m, 1H), 3.73 (s, 2H), 2.13-2.03 (m, 1H), 1.39-1.33 (m, 2H), 1.17-1.06 (m, 2H), 0.91-0.82 (m, 2H). | 471.2 |
| 40 | (DMSO-d6) 12.09-12.04 (m, 1H), 8.26 (s, 1H), 8.21-8.14 (m, 1H), 7.80 (dd, J = 7.7, 1.3 Hz, 1H), 7.68-7.59 (m, 3H), 7.50 (dd, J = 7.9, 1.3 Hz, 1H), 7.37 (d, J = 7.3 Hz, 1H), 7.28 (d, J = 1.7 Hz, 1H), 7.03-6.96 (m, 2H), 6.63 (dd, J = 7.4, 2.0 Hz, 1H), 6.55 (s, 2H), 5.13-5.07 (m, 1H), 4.34-4.27 (m, 1H), 4.13-4.05 (m, 1H), 2.13-2.04 (m, 1H), 1.14-1.03 (m, 2H), 0.92-0.82 (m, 2H). | 586.3 |
| 41 | (DMSO-d6) 12.10 (s, 1H), 8.15-8.09 (m, 2H), 7.95-7.90 (m, 2H), 7.80 (dd, J = 7.7, 1.4 Hz, 1H), 7.67-7.60 (m, 1H), 7.50 (dd, J = 7.8, 1.3 Hz, 1H), 7.38 (d, J = 7.4 Hz, 1H), 7.29 (d, J = 1.6 Hz, 1H), 7.04-6.96 (m, 2H), 6.66-6.58 (m, 3H), 5.10-5.04 (m, 1H), 4.35-4.28 (m, 1H), 4.14-4.06 (m, 1H), 3.24 (s, 3H), 2.13-2.04 (m, 1H), 1.14-1.03 (m, 2H), 0.91-0.82 (m, 2H). | 596.3 |
| 42 | (DMSO-d6) 12.02 (s, 1H), 8.07-7.98 (m, 1H), 7.90 (dd, J = 7.7, 2.6 Hz, 1H), 7.77 (dd, J = 7.8, 1.4 Hz, 1H), 7.68-7.61 (m, 1H), 7.50 (dd, J = 7.9, 1.3 Hz, 1H), 7.38 (d, J = 7.4 Hz, 1H), 7.28 (d, J = 1.5 Hz, 1H), 7.08-6.96 (m, 3H), 6.66-6.60 (m, 3H), 5.05-4.98 (m, 1H), 4.36-4.28 (m, 1H), 4.14-4.06 (m, 1H), 2.13-2.04 (m, 1H), 1.14-1.05 (m, 2H), 0.91-0.84 (m, 2H). | 537.5 |
| 43 | (DMSO-d6) 12.13 (s, 1H), 8.22 (d, J = 5.4 Hz, 1H), 7.85-7.74 (m, 2H), 7.67-7.60 (m, 2H), 7.51 (dd, J = 7.8, 1.3 Hz, 1H), 7.37 (d, J = 7.4 Hz, 1H), 7.28 (d, J = 1.7 Hz, 1H), 7.22 (d, J = 1.5 Hz, 1H), 7.00 (dd, J = 13.3, 1.7 Hz, 1H), 6.70 (s, 2H), 6.63 (dd, J = 7.5, 2.1 Hz, 1H), 5.01-4.94 (m, 1H), 4.37-4.29 (m, 1H), 4.14-4.06 (m, 1H), 2.13-2.04 (m, 1H), 1.14-1.05 (m, 2H), 0.91-0.84 (m, 2H). | 537.5 |
| 44 | (DMSO-d6) 11.99 (s, 1H), 7.84-7.74 (m, 1H), 7.70-7.60 (m, 3H), 7.51 (dd, J = 8.0, 1.4 Hz, 1H), 7.37 (d, J = 7.3 Hz, 1H), 7.29 (d, J = 1.7 Hz, 1H), 7.18-7.10 (m, 1H), 7.05-6.97 (m, 2H), 6.67-6.60 (m, 3H), 5.25-4.86 (m, 1H), | 554.2 |

TABLE 2-2-continued

| Examples | ¹H-NMR δ (ppm) | LCMS m/z [M + H]⁺ |
|---|---|---|
|  | 4.34-4.28 (m, 1H), 4.13-4.07 (m, 1H), 2.13-2.04 (m, 1H), 1.17-1.05 (m, 2H), 0.91-0.82 (m, 2H). |  |
| 45 | (DMSO-d6) 11.99-11.93 (m, 1H), 8.58 (d, J = 2.9 Hz, 1H), 8.06 (dd, J = 8.9, 4.3 Hz, 1H), 7.85-7.74 (m, 2H), 7.68-7.59 (m, 1H), 7.49 (dd, J = 8.0, 1.2 Hz, 1H), 7.37 (d, J = 7.4 Hz, 1H), 7.28 (d, J = 1.7 Hz, 1H), 7.04-6.92 (m, 2H), 6.63 (dd, J = 7.5, 2.1 Hz, 1H), 6.54 (s, 2H), 5.10-5.03 (m, 1H), 4.35-4.27 (m, 1H), 4.14-4.04 (m, 1H), 2.14-2.02 (m, 1H), 1.15-1.05 (m, 2H), 0.92-0.83 (m, 2H). | 537.5 |
| 46 | (DMSO-d6) 12.05 (s, 1H), 9.01-8.96 (m, 1H), 8.47 (d, J = 2.6 Hz, 1H), 8.24-8.17 (m, 1H), 7.78 (dd, J = 7.7, 1.4 Hz, 1H), 7.67-7.59 (m, 1H), 7.50 (dd, J = 7.9, 1.3 Hz, 1H), 7.38 (d, J = 7.4 Hz, 1H), 7.28 (d, J = 1.7 Hz, 1H), 7.08 (d, J = 1.6 Hz, 1H), 7.00 (dd, J = 13.3, 1.7 Hz, 1H), 6.66-6.59 (m, 3H), 5.08-5.02 (m, 1H), 4.35-4.28 (m, 1H), 4.14-4.05 (m, 1H), 2.13-2.04 (m, 1H), 1.14-1.05 (m, 2H), 0.91-0.84 (m, 2H). | 537.1 |
| 47 | (DMSO-d6) 11.71 (s, 1H), 8.55-8.46 (m, 1H), 7.86-7.72 (m, 2H), 7.63-7.55 (m, 1H), 7.52-7.41 (m, 1H), 7.35 (d, J = 7.4 Hz, 1H), 7.31-7.21 (m, 1H), 6.98 (dd, J = 13.1, 1.8 Hz, 1H), 6.74-6.65 (m, 1H), 6.61 (dd, J = 7.5, 2.0 Hz, 1H), 6.53-6.43 (m, 2H), 6.32 (s, 2H), 5.26-5.18 (m, 1H), 4.29-4.20 (m, 1H), 4.10-4.00 (m, 1H), 2.79 (d, J = 4.8 Hz, 3H), 2.12-2.01 (m, 1H), 1.13-1.02 (m, 2H), 0.93-0.77 (m, 2H). | 548.6 |
| 48 | (DMSO-d6) 11.82 (s, 1H), 8.64 (d, J = 2.4 Hz, 1H), 8.02 (dd, J = 8.9, 2.5 Hz, 1H), 7.79 (dd, J = 7.7, 1.3 Hz, 1H), 7.64-7.58 (m, 1H), 7.47 (dd, J = 7.9, 1.3 Hz, 1H), 7.37 (d, J = 7.4 Hz, 1H), 7.28 (d, J = 1.6 Hz, 1H), 7.00 (dd, J = 13.4, 1.6 Hz, 1H), 6.90 (d, J = 8.9 Hz, 1H), 6.63 (d, J = 7.1 Hz, 2H), 6.37 (s, 2H), 5.23 (s, 1H), 4.30-4.23 (m, 1H), 4.10-4.03 (m, 1H), 3.74-3.68 (m, 4H), 3.53-3.47 (m, 4H), 2.13-2.04 (m, 1H), 1.14-1.06 (m, 2H), 0.91-0.84 (m, 2H). | 604.3 |
| 49 | (DMSO-d6) 12.03 (s, 1H), 8.14 (d, J = 5.5 Hz, 1H), 7.77 (dd, J = 7.7, 1.4 Hz, 1H), 7.67-7.58 (m, 1H), 7.55-7.42 (m, 2H), 7.37 (d, J = 7.4 Hz, 1H), 7.28 (d, J = 1.6 Hz, 2H), 7.08-6.95 (m, 2H), 6.66-6.58 (m, 3H), 5.06-4.98 (m, 1H), 4.36-4.27 (m, 1H), 4.14-4.04 (m, 1H), 3.87 (s, 3H), 2.14-2.02 (m, 1H), 1.15-1.03 (m, 2H), 0.92-0.81 (m, 2H). | 549.2 |
| 50 | (DMSO-d6) 11.97 (s, 1H), 7.97 (d, J = 5.4 Hz, 1H), 7.80-7.73 (m, 1H), 7.67-7.58 (m, 1H), 7.52-7.46 (m, 1H), 7.37 (d, J = 7.4 Hz, 1H), 7.28 (s, 1H), 7.04-6.92 (m, 2H), 6.86-6.79 (m, 2H), 6.62 (dd, J = 7.4, 2.0 Hz, 1H), 6.53 (s, 2H), 6.41-6.32 (m, 1H), 5.10-5.02 (m, 1H), 4.35-4.26 (m, 1H), 4.14-4.04 (m, 1H), 2.80 (d, J = 4.8 Hz, 3H), 2.14-2.02 (m, 1H), 1.15-1.05 (m, 2H), 0.92-0.78 (m, 2H). | 548.2 |
| 51 | (DMSO-d6) 11.87 (d, J = 2.1 Hz, 1H), 7.89-7.71 (m, 3H), 7.68-7.57 (m, 1H), 7.48 (dd, J = 7.9, 1.3 Hz, 1H), 7.43-7.24 (m, 4H), 7.00 (dd, J = 13.2, 1.7 Hz, 1H), 6.73 (d, J = 2.1 Hz, 1H), 6.63 (dd, J = 7.6, 2.1 Hz, 1H), 6.45 (s, 2H), 5.26-5.07 (m, 1H), 4.35-4.22 (m, 1H), 4.18-3.99 (m, 1H), 3.39 (s, 2H), 2.15 (s, 6H), 2.13-2.02 (m, 1H), 1.18-1.04 (m, 2H), 0.96-0.79 (m, 2H). | 575.2 |
| 52 | (DMSO-d6) 11.86 (s, 1H), 7.85-7.73 (m, 3H), 7.66-7.58 (m, 1H), 7.48 (dd, J = 7.9, 1.4 Hz, 1H), 7.43-7.30 (m, 3H), 7.28 (d, J = 1.6 Hz, 1H), 7.00 (dd, J = 13.1, 1.7 Hz, 1H), 6.72 (s, 1H), 6.63 (dd, J = 7.4, 2.1 Hz, 1H), 6.43 (s, 2H), 5.19 (s, 1H), 4.35-4.21 (m, 1H), 4.16-3.97 (m, 1H), 3.53 (s, 2H), 2.46 (q, J = 7.1 Hz, 4H), 2.17-2.00 (m, 1H), 1.17-1.05 (m, 2H), 0.98 (t, J = 7.1 Hz, 6H), 0.92-0.81 (m, 2H). | 603.2 |
| 53 | (DMSO-d6) 11.87 (s, 1H), 7.83-7.76 (m, 3H), 7.66-7.59 (m, 1H), 7.48 (dd, J = 7.9, 1.3 Hz, 1H), 7.41-7.31 (m, 3H), 7.28 (d, J = 1.6 Hz, 1H), 7.00 (dd, J = 13.3, 1.7 Hz, 1H), 6.72 (d, J = 2.1 Hz, 1H), 6.63 (dd, J = 7.5, 2.1 Hz, 1H), 6.44 (s, 2H), 5.20-5.14 (m, 1H), 4.32-4.25 (m, 1H), 4.12-4.04 (m, 1H), 3.59 (s, 2H), 2.49-2.39 (m, 4H), 2.13-2.04 (m, 1H), 1.77-1.66 (m, 4H), 1.14-1.02 (m, 2H), 0.91-0.83 (m, 2H). | 601.2 |
| 54 | (DMSO-d6) 11.88 (s, 1H), 7.92-7.71 (m, 3H), 7.71-7.56 (m, 1H), 7.48 (dd, J = 7.9, 1.3 Hz, 1H), 7.44-7.19 (m, 4H), 7.00 (dd, J = 13.3, 1.6 Hz, 1H), 6.72 (d, J = 2.1 Hz, 1H), 6.63 (dd, J = 7.5, 2.1 Hz, 1H), 6.45 (s, 2H), 5.28-5.07 (m, 1H), 4.37-4.22 (m, 1H), 4.17-4.00 (m, 1H), 3.44 (s, 2H), 2.44-2.20 (m, 4H), 2.17-2.01 (m, 1H), 1.60-1.43 (m, 4H), 1.45-1.31 (m, 2H), 1.17-1.03 (m, 2H), 0.95-0.79 (m, 2H). | 615.2 |

TABLE 2-2-continued

| Examples | ¹H-NMR δ (ppm) | LCMS m/z [M + H]⁺ |
|---|---|---|
| 55 | (DMSO-d6) 11.94-11.82 (m, 1H), 7.91-7.73 (m, 3H), 7.69-7.56 (m, 1H), 7.48 (dd, J = 7.9, 1.3 Hz, 1H), 7.37 (dd, J = 13.2, 7.6 Hz, 3H), 7.28 (d, J = 1.7 Hz, 1H), 7.00 (dd, J = 13.2, 1.7 Hz, 1H), 6.75 (d, J = 2.1 Hz, 1H), 6.63 (dd, J = 7.5, 2.1 Hz, 1H), 6.45 (s, 2H), 5.22-5.08 (m, 1H), 4.38-4.22 (m, 1H), 4.16-4.01 (m, 1H), 3.55 (s, 2H), 3.26 (t, J = 5.6 Hz, 2H), 2.97 (s, 2H), 2.81 (s, 3H), 2.64 (t, J = 5.4 Hz, 2H), 2.15-2.01 (m, 1H), 1.17-1.04 (m, 2H), 0.95-0.79 (m, 2H). | 644.3 |
| 56 | (DMSO-d6) 11.84 (s, 1H), 7.85-7.72 (m, 3H), 7.66-7.58 (m, 1H), 7.48 (dd, J = 7.9, 1.3 Hz, 1H), 7.38 (d, J = 7.4 Hz, 1H), 7.28 (d, J = 1.6 Hz, 1H), 7.26-7.20 (m, 2H), 7.00 (dd, J = 13.3, 1.7 Hz, 1H), 6.70 (d, J = 2.0 Hz, 1H), 6.63 (dd, J = 7.5, 2.1 Hz, 1H), 6.44 (s, 2H), 5.23-5.15 (m, 1H), 4.33-4.24 (m, 1H), 4.13-3.98 (m, 1H), 2.32 (s, 3H), 2.14-2.02 (m, 1H), 1.13-1.07 (m, 2H), 0.92-0.83 (m, 2H). | 532.1 |
| 57 | (Chloroform-d) 8.66 (s, 1H), 7.80 (dd, J = 7.7, 1.4 Hz, 1H), 7.60-7.44 (m, 2H), 7.34 (d, J = 7.4 Hz, 1H), 7.05 (d, J = 1.6 Hz, 1H), 6.79 (dd, J = 12.8, 1.7 Hz, 1H), 6.50 (dd, J = 7.5, 2.0 Hz, 1H), 6.12 (d, J = 2.2 Hz, 1H), 4.85 (s, 2H), 4.28 (q, J = 12.3 Hz, 2H), 2.17 (s, 1H), 2.06-1.94 (m, 1H), 1.36 (s, 9H), 1.17-1.08 (m, 2H), 0.89-0.80 (m, 2H). | 498.2 |
| 58 | (DMSO-d6) 11.71-11.62 (m, 1H), 8.23 (d, J = 0.8 Hz, 1H), 7.97 (d, J = 0.8 Hz, 1H), 7.74 (dd, J = 7.8, 1.3 Hz, 1H), 7.65-7.56 (m, 1H), 7.46 (dd, J = 7.9, 1.3 Hz, 1H), 7.43-7.22 (m, 7H), 7.00 (dd, J = 13.2, 1.7 Hz, 1H), 6.62 (dd, J = 7.6, 2.0 Hz, 1H), 6.44 (d, J = 2.0 Hz, 1H), 6.33 (s, 2H), 5.36 (s, 2H), 5.27-5.17 (m, 1H), 4.30-4.20 (m, 1H), 4.11-3.99 (m, 1H), 2.14-2.01 (m, 1H), 1.16-1.02 (m, 2H), 0.94-0.81 (m, 2H). | 598.2 |
| 59 | (DMSO-d6) 11.78-11.73 (m, 1H), 8.58 (d, J = 2.5 Hz, 1H), 7.94 (dd, J = 8.9, 2.6 Hz, 1H), 7.77 (dd, J = 7.7, 1.4 Hz, 1H), 7.64-7.55 (m, 1H), 7.45 (dd, J = 7.9, 1.4 Hz, 1H), 7.36 (d, J = 7.4 Hz, 1H), 7.27 (d, J = 1.6 Hz, 1H), 6.98 (dd, J = 13.4, 1.5 Hz, 1H), 6.68 (d, J = 9.0 Hz, 1H), 6.61 (dd, J = 7.5, 2.1 Hz, 1H), 6.56 (d, J = 2.0 Hz, 1H), 6.34 (s, 2H), 5.26-5.17 (m, 1H), 4.30-4.21 (m, 1H), 4.10-4.00 (m, 1H), 3.05 (s, 6H), 2.12-2.01 (m, 1H), 1.13-1.04 (m, 2H), 0.91-0.82 (m, 2H). | 562.2 |
| 60 | (DMSO-d6) 11.73 (s, 1H), 8.48 (d, J = 2.5 Hz, 1H), 7.85-7.75 (m, 2H), 7.65-7.57 (m, 1H), 7.47 (dd, J = 7.9, 1.3 Hz, 1H), 7.37 (d, J = 7.4 Hz, 1H), 7.28 (d, J = 1.6 Hz, 1H), 7.00 (dd, J = 13.2, 1.7 Hz, 1H), 6.85-6.79 (m, 1H), 6.63 (dd, J = 7.5, 2.1 Hz, 1H), 6.59-6.50 (m, 2H), 6.35 (s, 2H), 5.28-5.21 (m, 1H), 4.30-4.23 (m, 1H), 4.11-4.02 (m, 1H), 3.53-3.42 (m, 4H), 3.28 (s, 3H), 2.13-2.04 (m, 1H), 1.15-1.03 (m, 2H), 0.93-0.81 (m, 2H). | 592.3 |
| 61 | (DMSO-d6) 11.87 (s, 1H), 7.85-7.74 (m, 3H), 7.66-7.58 (m, 1H), 7.48 (dd, J = 7.9, 1.3 Hz, 1H), 7.38 (d, J = 7.4 Hz, 1H), 7.35-7.30 (m, 2H), 7.28 (d, J = 1.7 Hz, 1H), 7.00 (dd, J = 13.2, 1.7 Hz, 1H), 6.72 (s, 1H), 6.63 (dd, J = 7.5, 2.1 Hz, 1H), 6.44 (s, 2H), 5.17 (s, 1H), 4.43-4.22 (m, 2H), 4.08 (dd, J = 12.1, 8.5 Hz, 1H), 3.53-3.40 (m, 4H), 2.45-2.23 (m, 10H), 2.16-2.00 (m, 1H), 1.15-1.03 (m, 2H), 0.94-0.81 (m, 2H). | 660.2 |
| 62 | (DMSO-d6) δ 11.65 (s, 1H), 8.15 (s, 1H), 7.90 (s, 1H), 7.73 (dd, J = 7.8, 1.3 Hz, 1H), 7.65-7.49 (m, 1H), 7.45 (dd, J = 7.8, 1.3 Hz, 1H), 7.35 (d, J = 7.4 Hz, 1H), 7.27 (d, J = 1.6 Hz, 1H), 6.98 (dd, J = 13.2, 1.7 Hz, 1H), 6.61 (dd, J = 7.5, 2.1 Hz, 1H), 6.40 (d, J = 1.9 Hz, 1H), 6.31 (s, 2H), 5.22 (dd, J = 8.9, 4.5 Hz, 1H), 4.24 (dd, J = 12.0, 4.3 Hz, 1H), 4.13 (q, J = 7.3 Hz, 2H), 4.04 (dd, J = 12.0, 8.9 Hz, 1H), 2.14-2.01 (m, 1H), 1.38 (t, J = 7.3 Hz, 3H), 1.13-1.02 (m, 2H), 0.91-0.79 (m, 2H). | 536.3 |
| 63 | (DMSO-d6) δ 11.63 (s, 1H), 8.21 (s, 1H), 7.90 (d, J = 0.7 Hz, 1H), 7.73 (dd, J = 7.8, 1.4 Hz, 1H), 7.65-7.55 (m, 1H), 7.45 (dd, J = 7.9, 1.3 Hz, 1H), 7.35 (d, J = 7.4 Hz, 1H), 7.27 (d, J = 1.6 Hz, 1H), 6.98 (dd, J = 13.3, 1.6 Hz, 1H), 6.61 (dd, J = 7.5, 2.1 Hz, 1H), 6.40 (s, 1H), 6.30 (s, 2H), 5.23 (dd, J = 8.8, 4.5 Hz, 1H), 4.56-4.41 (m, 1H), 4.24 (dd, J = 12.0, 3.7 Hz, 1H), 4.04 (dd, J = 12.0, 8.6 Hz, 1H), 2.12-2.01 (m, 1H), 1.42 (d, J = 6.6 Hz, 6H), 1.13-1.02 (m, 2H), 0.91-0.82 (m, 2H). | 550.4 |
| 64 | (DMSO-d6) δ 11.77 (s, 1H), 8.93 (s, 1H), 8.25 (s, 1H), 7.85-7.74 (m, 3H), 7.66-7.59 (m, 1H), 7.58-7.45 (m, 3H), 7.40-7.31 (m, 2H), 7.30-7.21 (m, 1H), 7.00 (dd, J = 13.1, 1.7 Hz, 1H), 6.66-6.57 (m, 2H), 6.39 (s, 2H), 5.18 | 584.4 |

TABLE 2-2-continued

| Examples | ¹H-NMR δ (ppm) | LCMS m/z [M + H]⁺ |
|---|---|---|
| | (dd, J = 8.9, 4.6 Hz, 1H), 4.28 (dd, J = 12.1, 4.2 Hz, 1H), 4.08 (dd, J = 12.1, 8.7 Hz, 1H), 2.08 (td, J = 8.3, 4.3 Hz, 1H), 1.14-1.06 (m, 2H), 0.93-0.80 (m, 2H). | |
| 65 | (DMSO-d6) δ 11.92 (d, J = 2.1 Hz, 1H), 8.67 (dd, J = 2.5, 0.8 Hz, 1H), 8.17 (dd, J = 8.7, 2.6 Hz, 1H), 7.78 (dd, J = 7.7, 1.3 Hz, 1H), 7.66-7.56 (m, 1H), 7.48 (dd, J = 7.8, 1.3 Hz, 1H), 7.37 (d, J = 7.4 Hz, 1H), 7.28 (d, J = 1.6 Hz, 1H), 7.00 (dd, J = 13.2, 1.7 Hz, 1H), 6.88 (dd, J = 8.7, 0.7 Hz, 1H), 6.75 (d, J = 2.1 Hz, 1H), 6.63 (dd, J = 7.5, 2.0 Hz, 1H), 6.46 (s, 2H), 5.15 (dd, J = 8.9, 4.5 Hz, 1H), 4.29 (dd, J = 12.1, 4.4 Hz, 1H), 4.08 (dd, J = 12.0, 8.8 Hz, 1H), 3.89 (s, 3H), 2.13-2.04 (m, 1H), 1.14-1.06 (m, 2H), 0.91-0.82 (m, 2H). | 549.5 |
| 66 | (DMSO-d6) δ 11.88 (s, 1H), 7.85-7.81 (m, 2H), 7.79 (dd, J = 7.7, 1.3 Hz, 1H), 7.77-7.72 (m, 1H), 7.67-7.59 (m, 1H), 7.48 (dd, J = 7.9, 1.3 Hz, 1H), 7.41-7.33 (m, 3H), 7.28 (d, J = 1.7 Hz, 1H), 7.00 (dd, J = 13.2, 1.7 Hz, 1H), 6.75 (d, J = 2.1 Hz, 1H), 6.63 (dd, J = 7.5, 2.1 Hz, 1H), 6.45 (s, 2H), 5.16 (dd, J = 8.7, 4.6 Hz, 1H), 4.29 (dd, J = 12.1, 4.4 Hz, 1H), 4.08 (dd, J = 12.1, 8.8 Hz, 1H), 3.55 (s, 2H), 3.19-3.12 (m, 2H), 2.92 (s, 2H), 2.58-2.52 (m, 2H), 2.13-2.04 (m, 1H), 1.14-1.05 (m, 2H), 0.93-0.83 (m, 2H). | 630.4 |
| 67 | (DMSO-d6) δ 11.88 (s, 1H), 7.86-7.76 (m, 3H), 7.66-7.59 (m, 1H), 7.48 (dd, J = 7.9, 1.3 Hz, 1H), 7.42-7.32 (m, 3H), 7.28 (d, J = 1.7 Hz, 1H), 7.00 (dd, J = 13.1, 1.7 Hz, 1H), 6.75 (d, J = 2.0 Hz, 1H), 6.63 (dd, J = 7.5, 2.1 Hz, 1H), 6.45 (s, 2H), 5.16 (dd, J = 8.8, 4.6 Hz, 1H), 4.33-4.24 (m, 1H), 4.08 (dd, J = 12.0, 8.7 Hz, 1H), 4.02 (s, 2H), 3.51 (s, 2H), 3.02 (t, J = 6.3 Hz, 2H), 2.89 (t, J = 6.3 Hz, 2H), 2.13-2.04 (m, 1H), 1.17-1.05 (m, 2H), 0.88 (dt, J = 6.8, 4.5 Hz, 2H). | 618.8 |
| 68 | (DMSO-d6) δ 11.35 (s, 1H), 7.78-7.50 (m, 4H), 7.36 (dd, J = 7.4, 4.3 Hz, 1H), 7.28 (d, J = 1.6 Hz, 1H), 7.07-6.92 (m, 1H), 6.61 (dd, J = 7.5, 2.2 Hz, 1H), 6.48-6.17 (m, 2H), 5.99-5.89 (m, 1H), 5.34-4.86 (m, 1H), 4.22 (d, J = 10.7 Hz, 1H), 4.04 (d, J = 11.1 Hz, 1H), 3.66-3.38 (m, 4H), 2.42 (s, 2H), 2.18-1.99 (m, 1H), 1.43 (s, 9H), 1.19-0.99 (m, 2H), 0.96-0.78 (m, 2H). | 623.3 |
| 69 | (DMSO-d6) δ 11.52 (s, 1H), 7.79-7.65 (m, 1H), 7.66-7.54 (m, 1H), 7.45 (dd, J = 7.9, 6.6 Hz, 1H), 7.36 (dd, J = 7.4, 5.3 Hz, 1H), 7.32-7.24 (m, 1H), 7.00 (dd, J = 13.3, 1.7 Hz, 1H), 6.69-6.57 (m, 1H), 6.55-6.19 (m, 4H), 5.36-4.93 (m, 1H), 4.34-3.91 (m, 3H), 3.75-3.45 (m, 3H), 2.45-2.36 (m, 2H), 2.19-1.96 (m, 4H), 1.17-1.02 (m, 2H), 0.95-0.80 (m, 2H). | 565.3 |
| 70 | (DMSO-d6) δ 11.48 (s, 1H), 7.77-7.65 (m, 1H), 7.65-7.53 (m, 1H), 7.52-7.40 (m, 1H), 7.41-7.32 (m, 1H), 7.33-7.22 (m, 1H), 7.00 (dd, J = 13.2, 1.6 Hz, 1H), 6.62 (dd, J = 7.5, 2.2 Hz, 1H), 6.54-6.17 (m, 4H), 5.38-4.85 (m, 1H), 4.32-4.15 (m, 1H), 4.13-3.96 (m, 1H), 3.98-3.88 (m, 1H), 3.71-3.47 (m, 5H), 3.49-3.27 (m, 2H), 3.26-3.01 (m, 6H), 2.18-2.01 (m, 1H), 1.14-1.04 (m, 2H), 0.94-0.81 (m, 2H). | 636.3 |
| 71 | (DMSO-d6) δ 11.55 (s, 1H), 7.72 (dd, J = 7.7, 1.4 Hz, 1H), 7.65-7.55 (m, 1H), 7.46 (dd, J = 7.9, 1.4 Hz, 1H), 7.37 (d, J = 7.4 Hz, 1H), 7.28 (d, J = 1.6 Hz, 1H), 7.00 (dd, J = 13.2, 1.7 Hz, 1H), 6.62 (dd, J = 7.5, 2.2 Hz, 1H), 6.43 (s, 2H), 6.38-6.30 (m, 1H), 6.25 (d, J = 2.0 Hz, 1H), 5.17 (dd, J = 8.6, 4.6 Hz, 1H), 4.25 (dd, J = 11.8, 3.5 Hz, 1H), 4.05 (dd, J = 11.8, 8.2 Hz, 1H), 3.89 (d, J = 3.4 Hz, 2H), 3.25-3.06 (m, 4H), 2.50-2.39 (m, 4H), 2.37-2.23 (m, 4H), 2.18 (s, 3H), 2.13-2.02 (m, 1H), 1.18-0.99 (m, 2H), 0.96-0.79 (m, 2H). | 649.4 |
| 72 | (DMSO-d6) δ 11.60 (s, 1H), 8.30 (s, 1H), 7.92 (s, 1H), 7.73 (dd, J-7.7, 1.4 Hz, 1H), 7.64-7.55 (m, 1H), 7.44 (dd, J = 7.9, 1.3 Hz, 1H), 7.34 (d, J = 7.4 Hz, 1H), 7.26 (d, J = 1.6 Hz, 1H), 6.98 (dd, J = 13.2, 1.6 Hz, 1H), 6.61 (dd, J = 7.5, 2.1 Hz, 1H), 6.43 (d, J = 2.0 Hz, 1H), 6.29 (s, 2H), 5.23 (s, 1H), 4.27-4.19 (m, 1H), 4.09-4.00 (m, 1H), 2.12-2.00 (m, 1H), 1.52 (s, 9H), 1.13-1.01 (m, 2H), 0.90-0.79 (m, 2H). | 564.3 |
| 73 | (DMSO-d6) δ 11.87 (s, 1H), 7.85-7.76 (m, 3H), 7.66-7.57 (m, 1H), 7.48 (dd, J = 7.9, 1.3 Hz, 1H), 7.38 (d, J = 7.3 Hz, 1H), 7.35-7.26 (m, 3H), 7.00 (dd, J = 13.3, 1.7 Hz, 1H), 6.73 (d, J = 2.1 Hz, 1H), 6.63 (dd, J = 7.5, 2.1 Hz, 1H), 6.45 (s, 2H), 5.17 (s, 1H), 4.57-4.53 (m, 1H), 4.29 (d, J = 11.9 Hz, 1H), 4.08 (dd, J = 11.5, 4.3 Hz, 1H), 3.46 (s, 2H), 2.73-2.65 (m, 2H), 2.14-2.02 (m, 3H), 1.75-1.66 (m, | 631.5 |

TABLE 2-2-continued

| Examples | ¹H-NMR δ (ppm) | LCMS m/z [M + H]⁺ |
|---|---|---|
|  | 2H), 1.45-1.34 (m, 2H), 1.28-1.22 (m, 1H), 1.14-1.05 (m, 2H), 0.93-0.80 (m, 2H). |  |
| 74 | (DMSO-d6) δ 11.87 (s, 1H), 7.84-7.74 (m, 3H), 7.66-7.59 (m, 1H), 7.53-7.45 (m, 1H), 7.36 (dd, J = 20.5, 7.6 Hz, 3H), 7.30-7.25 (m, 1H), 7.00 (dd, J = 13.2, 1.7 Hz, 1H), 6.75-6.71 (m, 1H), 6.63 (dd, J = 7.5, 2.1 Hz, 1H), 6.44 (s, 2H), 5.20-5.14 (m, 1H), 4.32-4.26 (m, 1H), 4.11-4.05 (m, 1H), 3.52-3.48 (m, 2H), 3.23-3.14 (m, 5H), 2.69-2.65 (m, 2H), 2.13-2.04 (m, 2H), 1.85-1.79 (m, 2H), 1.46-1.42 (m, 2H), 1.14-1.05 (m, 2H), 0.98-0.83 (m, 2H). | 645.0 |
| 75 | (DMSO-d6) δ 11.88 (s, 1H), 7.85-7.75 (m, 3H), 7.67-7.58 (m, 1H), 7.48 (dd, J = 7.9, 1.3 Hz, 1H), 7.41-7.29 (m, 3H), 7.28 (d, J = 1.7 Hz, 1H), 7.00 (dd, J = 13.3, 1.6 Hz, 1H), 6.73 (d, J = 1.4 Hz, 1H), 6.63 (dd, J = 7.5, 2.1 Hz, 1H), 6.44 (s, 2H), 5.16 (dd, J = 8.8, 4.5 Hz, 1H), 4.29 (dd, J = 12.0, 4.4 Hz, 1H), 4.08 (dd, J = 12.0, 8.8 Hz, 1H), 3.51 (s, 2H), 3.47-3.34 (m, 4H), 2.41-2.27 (m, 4H), 2.14-2.02 (m, 1H), 1.97 (s, 3H), 1.15-1.01 (m, 2H), 0.92-0.80 (m, 2H). | 658.3 |
| 76 | (Chloroform-d) δ 8.93 (s, 1H), 7.84 (dd, J = 7.7, 1.4 Hz, 1H), 7.60-7.47 (m, 4H), 7.44-7.33 (m, 3H), 7.05 (d, J = 1.6 Hz, 1H), 6.80 (dd, J = 12.7, 1.7 Hz, 1H), 6.71 (d, J = 2.1 Hz, 1H), 6.51 (dd, J = 7.5, 2.0 Hz, 1H), 4.89 (s, 2H), 4.38-4.25 (m, 2H), 3.75-3.67 (m, 2H), 3.53-3.47 (m, 3H), 2.72 (d, J = 10.8 Hz, 2H), 2.05-1.96 (m, 1H), 1.82-1.74 (m, 2H), 1.17-1.09 (m, 8H), 0.90-0.82 (m, 2H). | 645.5 |
| 77 | (Methanol-d4) δ 8.39 (s, 1H), 7.88 (dd, J = 7.8, 1.3 Hz, 1H), 7.78-7.63 (m, 3H), 7.49 (dd, J = 8.0, 1.3 Hz, 1H), 7.45-7.34 (m, 3H), 7.24 (d, J = 1.5 Hz, 1H), 6.93 (dd, J = 13.2, 1.6 Hz, 1H), 6.75-6.68 (m, 3H), 4.40 (d, J = 12.4 Hz, 1H), 4.27 (d, J = 12.3 Hz, 1H), 3.62 (s, 2H), 2.64-2.57 (m, 4H), 2.14-1.90 (m, 5H), 1.20-1.08 (m, 2H), 0.93-0.84 (m, 2H). | 651.2 |
| 78 | (DMSO-d6) δ 11.83-11.75 (m, 1H), 7.80-7.70 (m, 2H), 7.66-7.58 (m, 1H), 7.47 (dd, J = 7.9, 1.3 Hz, 1H), 7.37 (d, J = 7.4 Hz, 1H), 7.28 (d, J = 1.7 Hz, 1H), 7.00 (dd, J = 13.3, 1.7 Hz, 1H), 6.72 (d, J = 2.3 Hz, 1H), 6.62 (dd, J = 7.5, 2.2 Hz, 1H), 6.53 (d, J = 1.9 Hz, 1H), 6.39 (s, 2H), 5.25-5.14 (m, 1H), 4.34-4.21 (m, 1H), 4.13-4.02 (m, 1H), 3.89 (s, 3H), 2.16-2.00 (m, 1H), 1.16-1.05 (m, 2H), 0.95-0.80 (m, 2H). | 522.3 |
| 79 | (DMSO-d6) δ 11.83 (s, 1H), 7.81-7.71 (m, 3H), 7.63-7.54 (m, 1H), 7.44 (dd, J = 7.8, 1.3 Hz, 1H), 7.38-7.19 (m, 4H), 6.96 (dd, J = 13.2, 1.7 Hz, 1H), 6.69 (d, J = 2.1 Hz, 1H), 6.59 (dd, J = 7.5, 2.1 Hz, 1H), 6.40 (s, 2H), 5.12 (dd, J = 8.8, 4.5 Hz, 1H), 4.26 (dd, J = 12.0, 4.3 Hz, 1H), 4.05 (dd, J = 12.0, 8.7 Hz, 1H), 3.44 (s, 2H), 3.17-3.04 (m, 2H), 2.63-2.55 (m, 4H), 2.36 (s, 4H), 2.11-1.99 (m, 1H), 1.12-1.02 (m, 2H), 0.89-0.78 (m, 2H). | 698.4 |
| 80 | (DMSO-d6) δ 11.88-11.82 (m, 1H), 7.83-7.75 (m, 3H), 7.67-7.58 (m, 1H), 7.48 (dd, J = 7.8, 1.3 Hz, 1H), 7.41-7.26 (m, 4H), 7.04-6.95 (m, 1H), 6.73 (d, J = 2.2 Hz, 1H), 6.63 (dd, J = 7.4, 2.1 Hz, 1H), 6.44 (s, 2H), 5.17 (dd, J = 8.8, 4.5 Hz, 1H), 4.29 (dd, J = 12.1, 4.3 Hz, 1H), 4.09 (dd, J = 12.0, 8.7 Hz, 1H), 3.42 (s, 2H), 2.33-2.28 (m, 2H), 2.14-2.02 (m, 1H), 2.01-1.96 (m, 2H), 1.59-1.49 (m, 2H), 1.26-1.16 (m, 2H), 1.15-1.05 (m, 2H), 0.93-0.80 (m, 8H). | 643.3 |
| 81 | (DMSO-d6) δ 11.44 (s, 1H), 7.75-7.68 (m, 1H), 7.63-7.55 (m, 1H), 7.50-7.41 (m, 1H), 7.36 (d, J = 7.4 Hz, 1H), 7.28 (d, J = 1.6 Hz, 1H), 6.99 (dd, J = 13.2, 1.7 Hz, 1H), 6.62 (dd, J = 7.4, 2.0 Hz, 1H), 6.43-6.38 (m, 1H), 6.36 (s, 2H), 6.19-6.14 (m, 1H), 5.26-5.17 (m, 1H), 4.28-4.19 (m, 1H), 4.10-3.99 (m, 1H), 2.34-2.29 (m, 2H), 2.21-2.16 (m, 2H), 2.14-2.02 (m, 1H), 1.73-1.54 (m, 4H), 1.15-1.03 (m, 2H), 0.92-0.82 (m, 2H). | 522.4 |
| 82 | (DMSO-d6) δ 11.51 (s, 1H), 7.72 (dd, J = 7.7, 1.3 Hz, 1H), 7.63-7.56 (m, 1H), 7.49-7.42 (m, 1H), 7.36 (d, J = 7.4 Hz, 1H), 7.28 (d, J = 1.7 Hz, 1H), 6.99 (dd, J = 13.2, 1.7 Hz, 1H), 6.62 (dd, J = 7.5, 2.1 Hz, 1H), 6.59-6.53 (m, 1H), 6.41 (s, 2H), 6.34-6.25 (m, 1H), 5.16 (dd, J = 8.8, 4.5 Hz, 1H), 4.24 (dd, J = 12.0, 4.5 Hz, 1H), 4.05 (dd, J = 12.0, 8.8 Hz, 1H), 3.36-3.27 (m, 2H), 2.83-2.71 (m, 2H), 2.60 (s, 2H), 2.13-2.03 (m, 1H), 1.14-1.06 (m, 2H), 0.91-0.84 (m, 2H). | 540.2 |
| 83 | (DMSO-d6) δ 11.63 (s, 1H), 7.73 (dd, J = 7.7, 1.4 Hz, 1H), 7.63-7.56 (m, 1H), 7.47 (dd, J = 7.8, 1.4 Hz, 1H), 7.37 (d, J = 7.4 Hz, 1H), 7.28 (d, J = 1.6 Hz, 1H), 7.00 (dd, J = 13.2, | 572.6 |

TABLE 2-2-continued

| Examples | $^1$H-NMR δ (ppm) | LCMS m/z [M + H]$^+$ |
|---|---|---|
| | 1.7 Hz, 1H), 6.62 (dd, J = 7.5, 2.1 Hz, 1H), 6.49 (s, 2H), 6.39 (d, J = 2.1 Hz, 1H), 6.30-6.24 (m, 1H), 5.11 (dd, J = 8.7, 4.5 Hz, 1H), 4.26 (dd, J = 12.0, 4.4 Hz, 1H), 4.06 (dd, J = 12.1, 8.8 Hz, 1H), 3.97-3.92 (m, 2H), 3.36-3.25 (m, 2H), 3.05-2.99 (m, 2H), 2.13-2.03 (m, 1H), 1.14-1.03 (m, 2H), 0.87 (dt, J = 6.8, 3.4 Hz, 2H). | |
| 84 | (Methanol-d4) δ 7.84-7.75 (m, 1H), 7.72-7.60 (m, 1H), 7.47 (dd, J = 8.0, 1.3 Hz, 1H), 7.40-7.28 (m, 1H), 7.24 (d, J = 1.6 Hz, 1H), 6.93 (dd, J = 13.2, 1.7 Hz, 1H), 6.71 (dd, J = 7.3, 2.0 Hz, 1H), 6.34 (d, J = 10.4 Hz, 1H), 6.30-6.24 (m, 1H), 4.44-4.33 (m, 1H), 4.31-4.21 (m, 3H), 3.85-3.70 (m, 2H), 2.54-2.41 (m, 2H), 2.13-2.03 (m, 1H), 1.41-1.23 (m, 2H), 1.20-1.10 (m, 5H), 0.94-0.85 (m, 2H). | 579.2 |
| 85 | (DMSO-d6) δ 11.66-11.47 (m, 1H), 7.80-7.65 (m, 1H), 7.65-7.55 (m, 1H), 7.52-7.40 (m, 1H), 7.41-7.31 (m, 1H), 7.28 (d, J = 1.7 Hz, 1H), 6.99 (dd, J = 12.9, 1.7 Hz, 1H), 6.69-6.53 (m, 1H), 6.46-6.16 (m, 4H), 5.39-4.87 (m, 1H), 4.39-3.93 (m, 3H), 3.82-3.49 (m, 3H), 3.25-3.03 (m, 2H), 2.25-2.12 (m, 6H), 2.12-2.03 (m, 1H), 1.28-1.19 (m, 2H), 1.14-1.04 (m, 2H), 0.93-0.80 (m, 2H). | 608.7 |
| 86 | (DMSO-d6) δ 11.61-11.54 (m, 1H), 7.75-7.65 (m, 1H), 7.66-7.53 (m, 1H), 7.49-7.42 (m, 1H), 7.39-7.32 (m, 1H), 7.30-7.25 (m, 1H), 6.99 (dd, J = 13.1, 1.8 Hz, 1H), 6.65-6.58 (m, 1H), 6.51-6.32 (m, 2H), 6.28 (dd, J = 8.4, 6.2 Hz, 1H), 5.28-5.05 (m, 1H), 4.32-4.19 (m, 2H), 4.14-3.99 (m, 2H), 3.75-3.65 (m, 1H), 3.66-3.53 (m, 5H), 3.31-3.16 (m, 3H), 2.55-2.51 (m, 2H), 2.45-2.38 (m, 4H), 2.13-2.03 (m, 1H), 1.15-1.05 (m, 2H), 0.91-0.82 (m, 2H). | 650.4 |
| 87 | (DMSO-d6) δ 11.55 (s, 1H), 7.72 (dd, J = 7.7, 1.3 Hz, 1H), 7.64-7.53 (m, 1H), 7.46 (dd, J = 7.9, 1.3 Hz, 1H), 7.36 (d, J = 7.4 Hz, 1H), 7.28 (d, J = 1.7 Hz, 1H), 6.99 (dd, J = 13.2, 1.7 Hz, 1H), 6.62 (dd, J = 7.4, 2.1 Hz, 1H), 6.41 (s, 2H), 6.39-6.33 (m, 1H), 6.30-6.23 (m, 1H), 5.16 (dd, J = 8.8, 4.5 Hz, 1H), 4.25 (dd, J = 12.1, 4.4 Hz, 1H), 4.05 (dd, J = 12.0, 8.9 Hz, 1H), 3.88-3.83 (m, 2H), 3.30 (d, J = 6.3 Hz, 2H), 2.76 (s, 6H), 2.47 (d, J = 5.8 Hz, 2H), 2.13-2.03 (m, 1H), 1.14-1.05 (m, 2H), 0.91-0.84 (m, 2H). | 594.4 |
| 88 | (DMSO-d6) δ 11.55 (s, 1H), 7.72 (dd, J = 7.7, 1.3 Hz, 1H), 7.63-7.56 (m, 1H), 7.46 (dd, J = 8.0, 1.3 Hz, 1H), 7.37 (d, J = 7.4 Hz, 1H), 7.28 (d, J = 1.7 Hz, 1H), 7.00 (dd, J = 13.2, 1.7 Hz, 1H), 6.62 (dd, J = 7.5, 2.1 Hz, 1H), 6.42 (s, 2H), 6.35 (d, J = 3.7 Hz, 1H), 6.25 (s, 1H), 5.17 (dd, J = 8.8, 4.6 Hz, 1H), 4.25 (dd, J = 12.1, 4.3 Hz, 1H), 4.05 (dd, J = 12.0, 8.8 Hz, 1H), 3.92-3.87 (m, 2H), 3.41-3.33 (m, 2H), 3.32-3.25 (m, 6H), 2.13-2.03 (m, 1H), 1.79-1.68 (m, 4H), 1.14-1.06 (m, 2H), 0.87 (dt, J = 6.7, 3.4 Hz, 2H). | 620.7 |
| 89 | (DMSO-d6) δ 11.55 (s, 1H), 7.68 (dd, J = 7.8, 1.4 Hz, 1H), 7.61-7.52 (m, 1H), 7.43 (dd, J = 7.9, 1.3 Hz, 1H), 7.33 (d, J = 7.4 Hz, 1H), 7.25 (d, J = 1.6 Hz, 1H), 6.96 (dd, J = 13.2, 1.7 Hz, 1H), 6.59 (dd, J = 7.5, 2.1 Hz, 1H), 6.41 (s, 2H), 6.38-6.32 (m, 1H), 6.28-6.22 (m, 1H), 5.10 (dd, J = 8.7, 4.5 Hz, 1H), 4.22 (dd, J = 12.0, 4.5 Hz, 1H), 4.02 (dd, J = 12.0, 8.8 Hz, 1H), 3.89-3.83 (m, 2H), 3.36-3.21 (m, 2H), 2.90 (s, 3H), 2.56-2.51 (m, 2H), 2.11-1.99 (m, 1H), 1.12-1.02 (m, 2H), 0.89-0.80 (m, 2H). | 601.2 |
| 90 | (DMSO-d6) δ 11.58 (s, 1H), 7.72 (dd, J = 7.7, 1.4 Hz, 1H), 7.63-7.56 (m, 1H), 7.46 (dd, J = 7.8, 1.3 Hz, 1H), 7.36 (d, J = 7.4 Hz, 1H), 7.28 (d, J = 1.6 Hz, 1H), 7.00 (dd, J = 13.2, 1.7 Hz, 1H), 6.62 (dd, J = 7.4, 2.1 Hz, 1H), 6.45 (s, 2H), 6.38 (s, 1H), 6.27 (d, J = 2.1 Hz, 1H), 5.14 (dd, J = 8.8, 4.6 Hz, 1H), 4.25 (dd, J = 12.0, 4.3 Hz, 1H), 4.05 (dd, J = 12.0, 8.8 Hz, 1H), 4.03-3.96 (m, 2H), 3.50-3.35 (m, 3H), 3.33-3.27 (m, 2H), 2.13-2.03 (m, 1H), 1.23 (d, J = 6.8 Hz, 6H), 1.14-1.02 (m, 2H), 0.91-0.83 (m, 2H). | 629.3 |
| 91 | (DMSO-d6) δ 11.49 (s, 1H), 7.72 (dd, J = 7.7, 1.3 Hz, 1H), 7.66-7.56 (m, 1H), 7.45 (dd, J = 7.9, 1.3 Hz, 1H), 7.36 (d, J = 7.4 Hz, 1H), 7.28 (d, J = 1.7 Hz, 1H), 6.99 (dd, J = 13.1, 1.7 Hz, 1H), 6.62 (dd, J = 7.5, 2.1 Hz, 1H), 6.40-6.32 (m, 3H), 6.18 (d, J = 2.0 Hz, 1H), 5.18 (dd, J = 9.0, 4.6 Hz, 1H), 4.24 (dd, J = 12.1, 4.1 Hz, 1H), 4.05 (dd, J = 12.0, 8.6 Hz, 1H), 3.29 (s, 2H), 3.09-3.05 (m, 2H), 2.60-2.52 (m, 2H), 2.50-2.39 (m, 2H), 2.13-2.03 (m, 1H), 1.17-1.01 (m, 5H), 0.91-0.83 (m, 2H). | 551.3 |
| 92 | (DMSO-d6) δ 11.50 (s, 1H), 7.74-7.69 (m, 1H), 7.63-7.56 (m, 1H), 7.45 (dd, J = 7.8, 1.3 Hz, 1H), 7.36 (d, J = 7.4 Hz, 1H), 7.28 (d, J = 1.7 Hz, 1H), 6.99 (d, J = 13.0 Hz, 1H), | 577.2 |

TABLE 2-2-continued

| Examples | $^1$H-NMR δ (ppm) | LCMS m/z [M + H]$^+$ |
|---|---|---|
|  | 6.62 (dd, J = 7.4, 2.0 Hz, 1H), 6.40-6.34 (m, 3H), 6.19 (d, J = 2.1 Hz, 1H), 5.18 (s, 1H), 4.27-4.20 (m, 1H), 4.09-4.03 (m, 1H), 3.29 (s, 2H), 3.19-3.14 (m, 1H), 2.45-2.41 (m, 2H), 2.31-2.25 (m, 2H), 2.13-2.03 (m, 1H), 1.26-1.22 (m, 2H), 1.17-1.06 (m, 2H), 0.91-0.81 (m, 2H), 0.52-0.44 (m, 2H), 0.14-0.05 (m, 2H). |  |
| 93 | (DMSO-d6) δ 11.49 (s, 1H), 7.72 (dd, J = 7.7, 1.4 Hz, 1H), 7.65-7.54 (m, 1H), 7.46 (dd, J = 7.9, 1.3 Hz, 1H), 7.37 (d, J = 7.4 Hz, 1H), 7.28 (d, J = 1.7 Hz, 1H), 7.00 (dd, J = 13.2, 1.7 Hz, 1H), 6.69-6.55 (m, 1H), 6.46-6.33 (m, 3H), 6.18 (d, J = 1.7 Hz, 1H), 5.28-5.12 (m, 1H), 4.29-4.18 (m, 1H), 4.11-3.97 (m, 1H), 3.43-3.33 (m, 2H), 2.92-2.81 (m, 2H), 2.29 (s, 2H), 2.13-1.99 (m, 1H), 1.15-1.05 (m, 2H), 0.93-0.82 (m, 2H). | 523.5 |

Test Example 1

BTK Activity Inhibition Test
(Preparation of Dephosphorylated BTK)

Dephosphorylated BTK was obtained by adding λ protein phosphatase (manufactured by New England BioLabs Inc., Code No. P0753S) and MnCl$_2$ at 10 U/μg and 2 mM, respectively, to biotinylated BTK protein BTN-BTK (Manufactured by Carna Biosciences, Inc.) enzyme solution, reacting the mixture at 4° C. overnight, and removing of λ protein phosphatase by anti DYKDDDDK-tag antibody agarose gel chromatography, followed by buffer exchange using a 10DG Desalting Column.
(Kinase Activity Measuring Method)

The kinase activity was measured using QuickScout Screening Assist (trade mark) MSA (commercially available kit manufactured by Carna Biosciences, Inc.) by mobility shift assay (MSA) method. The substrate of the kinase reaction was an FITC-labeled SRCtide peptide included in the kit. An assay buffer [20 mM HEPES, 0.01% Triton X-100 (Trade mark), 2 mM dithiothreitol, pH 7.5] was used and adjusted at 4 μM substrate, 20 mM MgCl$_2$ and 200 μm ATP to obtain a substrate mixture solution. The enzyme solution was also prepared by diluting the dephosphorylated BTK to 0.46 nM using the assay buffer. The 10 mM solution of the test compound in DMSO was further diluted with DMSO to 10 levels of the concentration (0.00003 mM, 0.0001 mM, 0.0003 mM, 0.001 mM, 0.003 mM, 0.01 mM, 0.03 mM, 0.1 mM, 0.3 mM, 1 mM), each of which was subjected to a 25-fold dilution with the assay buffer to obtain the drug solutions (4% DMSO solutions). 5 μL of the drug solution or a control solution (4% DMSO-assay buffer), 5 μL of the substrate mixture solution, and 10 μL of the enzyme solution were mixed in the wells of a polypropylene 384-well plate and allowed to react at room temperature for 2 hours, and then quenched by adding 60 μL of the termination buffer included in the kit. Subsequently, the quantities of the substrates (S) and the phosphorylated substrate (P) in the reaction solution were measured using LabChip EZ Reader II system (manufactured by Caliper Life Sciences) according to the protocol of the assay kit.
(BTK Inhibiting Activity Evaluation Method)

The heights of the peaks of the isolated substrate and the phosphorylated substrate were represented as S and P, respectively, and a blank which contained the assay buffer instead of the enzyme solution was also measured.

The inhibition rate (%) of the test compound was calculated according to the following equation;

Inhibition rate (%)=(1−(C−A)/(B−A))×100 wherein, A, B and C represent P/(P+S) of the blank well, P/(P+S) of the control well and P/(P+S) of the compound-containing well, respectively.

The IC$_{50}$ value was calculated via a regression analysis of the inhibition rate (%) and the test compound concentration (logarithmic value).
(Evaluation Results)

Since the group of the compounds of the Examples showed the IC$_{50}$ values from 10 nM or less to 100 nM or less against dephosphorylated BTK, Compound (I) of the invention was revealed to have a potent BTK inhibiting effect. The inhibitory activity against dephosphorylated BTK of the representative compounds in the present invention was shown in Table 3. The inhibiting activity was indicated with the mark "*" when the IC$_{50}$ value is less than 0.01 μM, with the mark "" when the IC$_{50}$ value is from 0.01 μM to less than 0.1 μM, and with the mark "*" when the IC$_{50}$ value is from 0.1 μM to less than 1.0 μM.

TABLE 3

| Test Compound (Example No.) | Inhibitory Activity on BTK |
|---|---|
| 1 | *** |
| 2 | *** |
| 3 | *** |
| 4 | *** |
| 5 | *** |
| 6 | *** |
| 7 | *** |
| 8 | *** |
| 9 | *** |
| 10 | *** |
| 11 | ** |
| 12 | *** |
| 13 | *** |
| 14 | *** |
| 15 | *** |
| 16 | *** |
| 17 | *** |
| 18 | *** |
| 19 | *** |
| 20 | *** |
| 21 | *** |
| 22 | *** |
| 23 | *** |
| 24 | *** |
| 25 | *** |
| 26 | *** |
| 27 | *** |
| 28 | *** |
| 29 | *** |
| 30 | ** |
| 31 | *** |

TABLE 3-continued

| Test Compound (Example No.) | Inhibitory Activity on BTK |
|---|---|
| 32 | *** |
| 33 | *** |
| 34 | *** |
| 35 | *** |
| 36 | *** |
| 37 | *** |
| 38 | ** |
| 39 | ** |
| 40 | *** |
| 41 | *** |
| 42 | *** |
| 43 | *** |

Test Example 2

Intracellular BTK Auto-Phosphorylation Activity Inhibition Test
(Culture of Cells to be Used)

Ramos cells (2G6.4C10, ATCC No. CRL-1923) were cultured in a T75 flask containing RPMI-1640 medium (GIBCO, # A10491-01) supplemented with 10% FBS (Aus-Gene) and 1% penicillin-streptomycin (Nacalai Tesque, Inc.) (hereinafter referred to as growth medium) in a 5% $CO_2$ incubator.

(Addition of the Compound to be Tested)

The cultured Ramos cells were diluted to a cell density of $7.5 \times 10^6$ cells/mL with a serum-free RPMI-1640 (hereinafter referred to as medium) and kept at 37° C. for 45 minutes. The cell suspension was dispensed in 1 mL aliquots into 2.0 mL tubes. A 0.03 mM solution of the test substance in DMSO was diluted with the medium to make a 0.09 µM test compound solution, 500 µL of which was then added to the tubes and the incubation was conducted at 37° C. for 1 hour in the presence of the test compound at a final concentration of 0.03 µM. Thereafter, the anti-IgM antibody (Invitrogen, H15100) which had been diluted with the medium was added at a final concentration of 10 µg/mL, and the incubation was conducted at 37° C. for 10 minutes.

(Extraction of Proteins)

To the pellets obtained by recovering the cells via centrifugation, 100 µL of a lysis buffer [RIPA Buffer(×1)(Cell Signaling Technology, Inc.) supplemented with 1% Phosphatase inhibitor Cacktail 3 (Sigma Corporation, No. P0044), 1% Phosphatase inhibitor Cacktail (Nacalai Tesque, Inc., No. 07575) and 1 mM phenylmethylsulfonyl fluoride (PMSF)] was added and stirred gently and then allowed to stand for 10 minutes. The supernatant was recovered by centrifugation (15,000 rpm, 15 minutes) and the protein level was quantified. The portion was mixed with the SDS-sample buffer, allowed to react for 5 minutes at 95° C. to denature the protein, thereby obtaining a sample solution. Each 5 µL of the sample solutions was applied to each well containing a 5 to 20% gradient acrylamide gel (Nacalai Tesque, Inc., No. 13064-04) and electrophoresis was conducted. Thereafter, iBlot gel transfer system (Life Technologies Corporation) was used to transfer the proteins in the gel onto a PVDF membrane.

(Detection of BTK or Phosphorylated BTK)

The PVDF membrane after transfer was blocked with 2% ECL prime blocking Reagent (GE Healthcare) and thereafter the reaction was conducted overnight at 4° C. using anti-BTK mouse antibody (BD transduction laboratory, No. 611116) or anti-phosphorylated BTK rabbit antibody (pY223, EPITOMICS, No. 2207-1) as a primary antibody. The unreacted primary antibody was washed with a TBST buffer (10 mM Tris-HCl (pH 7.5), 150 mM NaCl, 0.1% Tween 20) and then the reaction was conducted for 1 hour at room temperature in a TBST buffer supplemented with 2% ECL prime blocking Reagent using HRP-labeled anti-mouse IgG horse antibody (Cell Signaling Technology, No. 7076) or anti-rabbit IgG goat antibody (Cell Signaling Technology, No. 7074) as a secondary antibody. After washing the unreacted secondary antibody with the TBST buffer, Chemi-Lumi One Super (Nacalai Tesque, Inc.) was used to conduct a reaction in accordance with the attached protocol, and then the respective bands as chemiluminescences were detected with a CCD camera (GE Healthcare ImageQuant LAS 500). The detected bands were subjected to densitometry (ImageQuant TL analyzing software v8.1) to be represented as numerical values, and the inhibition rate (%) was calculated based on the intensity of the band in each group, while taking the luminescence of the phosphorylated BTK band in the group without added compound with IgM stimulation as 100% and the luminescence of the phosphorylated BTK band in the group without added compound without IgM stimulation as 0%. Each phosphorylated BTK band was corrected based on the total BTK.

The combinations of the primary antibodies and the secondary antibodies employed in this test and the dilution magnitudes thereof are shown below.

TABLE 4

| Primary antibody (dilution magnitude) | Secondary antibody (dilution magnitude) |
|---|---|
| 1 Anti-BTK mouse antibody (1/4000) | Anti-mouse IgG horse antibody (1/5000) |
| 2 Anti-phosphorylated BTK rabbit antibody (1/500) | Anti-rabbit IgG goat antibody (1/5000) |

The results obtained at a test compound concentration of 0.03 µM are shown in Table 5. The intracellular BTK autophosphorylation inhibiting activity was indicated with the mark "*" when 90% or more, with the mark "" when 70% or more and less than 90%, and with the mark "*" when 50% or more and less than 70%.

The inhibitory effects of the representative compounds of the present invention on the intracellular autophosphorization are shown in Table 5. As shown in the table, the activity of intracellular autophosphorization was potently inhibited by compounds (I) of the present invention at a concentration of 0.03 µM.

TABLE 5

| Test Compound (Example No.) | Inhibitory Activity on BTK-phosphorization |
|---|---|
| 1 | *** |
| 2 | *** |
| 3 | *** |
| 5 | *** |
| 8 | *** |
| 13 | *** |
| 14 | ** |
| 15 | *** |
| 16 | *** |
| 17 | *** |
| 18 | *** |
| 23 | *** |
| 25 | *** |
| 26 | *** |
| 27 | *** |

TABLE 5-continued

| Test Compound (Example No.) | Inhibitory Activity on BTK-phosphorization |
|---|---|
| 32 | *** |

The results of Test Example 2 indicate that the compounds of the present invention have potent inhibitory effects also on "the intracellular BTK autophosphorylation activity".

Test Example 3

C481S Mutant BTK Inhibitory Activity Test
(Method for Measuring Kinase Activity)

The kinase activity was measured using QuickScout Screening Assist (trademark) MSA (commercially available kit manufactured by Carna Biosciences, Inc.) by mobility shift assay (MSA) method. The substrate of the kinase reaction was an FITC-labeled SRCtide peptide included in the kit. An assay buffer [20 mM HEPES, 0.01% Triton X-100 (trademark), 2 mM dithiothreitol, pH 7.5] was used and adjusted at 4 μM substrate, 20 mM MgCl$_2$ and 120 μm and 100 μm ATP, which are ATP concentrations close to Km value of wild type and C481S mutant BTK respectively, to obtain a substrate mixture solution. The enzyme solution was also prepared by diluting the wild type or C481S mutant BTK to 0.28 nM using the assay buffer. The 10 mM solution of the test compound in DMSO was further diluted with DMSO to 10 levels of the concentration (0.00003 mM, 0.0001 mM, 0.0003 mM, 0.001 mM, 0.003 mM, 0.01 mM, 0.03 mM, 0.1 mM, 0.3 mM, 1 mM), each of which was subjected to a 25-fold dilution with the assay buffer to obtain the drug solutions (4% DMSO solutions).

5 μL of the drug solution or a control solution (4% DMSO-assay buffer), 5 μL of the substrate mixture solution, and 10 μL of the enzyme solution were mixed in the wells of a polypropylene 384-well plate and allowed to react at room temperature for 1 hour, and then quenched by adding 60 μL of the termination buffer included in the kit. Subsequently, the quantities of the substrates (S) and the phosphorylated substrate (P) in the reaction solution were measured using LabChip EZ Reader II system (manufactured by Caliper Life Sciences) according to the protocol of the assay kit.

(BTK Inhibiting Activity Evaluation Method)

The heights of the peaks of the isolated substrate and the phosphorylated substrate were represented as S and P, respectively, and a blank which contained the assay buffer instead of the enzyme solution was also measured.

The inhibition rate (%) of the test compound was calculated according to the following equation;

Inhibition rate (%)=(1−(C−A)/(B−A))×100 wherein, A, B and C represent P/(P+S) of the blank well, P/(P+S) of the control well and P/(P+S) of the compound-containing well, respectively.

The IC$_{50}$ value was calculated via a regression analysis of the inhibition rate (%) and the test compound concentration (logarithmic value).

The inhibitory activity against the wild type BTK [BTK (WT)] and C481S mutant BTK [BTK(C481S)] of the representative compounds in the present invention was shown in Table 6. Values of IC$_{50}$[BTK(C481S)]/IC$_{50}$[BTK(WT)] were also listed in the table as a rough indication for C481S mutation-resistance

TABLE 6

| Test Compounds Example No. | BTK (WT) IC50 (nM) | BTK (C481S) IC50 (nM) | C481S mutation-resistance |
|---|---|---|---|
| 2 | 0.97 | 0.99 | 1.0 |
| 8 | 0.33 | 0.43 | 1.3 |
| 13 | 0.49 | 0.60 | 1.2 |
| 23 | 0.46 | 0.99 | 2.2 |
| 41 | 0.73 | 1.03 | 1.4 |
| 42 | 0.87 | 1.06 | 1.2 |
| 43 | 1.11 | 1.72 | 1.5 |
| 50 | 0.77 | 1.60 | 2.1 |
| 51 | 0.43 | 0.78 | 1.8 |
| 52 | 0.43 | 0.76 | 1.8 |
| 53 | 0.51 | 0.90 | 1.8 |
| 54 | 0.58 | 0.86 | 1.5 |
| 61 | 0.36 | 0.57 | 1.6 |
| 66 | 0.47 | 0.93 | 2 |
| 71 | 0.39 | 0.58 | 1.5 |
| 83 | 0.25 | 0.58 | 2.3 |
| 84 | 0.41 | 0.82 | 2 |
| 87 | 0.52 | 0.95 | 1.8 |
| 88 | 0.94 | 1.49 | 1.6 |
| 89 | 0.34 | 0.70 | 2.1 |
| 91 | 0.47 | 1.1 | 2.1 |
| 93 | 0.41 | 0.99 | 2.4 |
| ibrutinib | 0.21 | 5.8 | 27.6 |

As shown in Test Example 3, compounds (I) of the present invention have potent inhibitory activity also against C481S mutant BTK.

Test Example 4

Proliferation-Inhibitory Test Against Diffuse Large-Cell B-Cell Lymphoma OCI-Ly10 Strain OCI-Ly10 cells were cultured in IMDM medium (Iscove's Modified Dulbecco's Medium, Manufactured by Thermo Fisher Scientific Inc., hereinafter "medium") containing 20% Fetal bovine serum and 1% penicillin-streptomycin (Nacalai Tesque, Inc.) in a 5% CO2 incubator. OCI-Ly10 cells were seeded to 96-well plate (20000 cells/well), compounds diluted with medium were added with final concentrations of 0.9 nM to 30000 nM (Final DMSO concentration, 0.3%), incubated for 96 hours and alamorBlue reagent (Thermo Fisher Scientific Inc.) was added. Absorbance at 570-600 nm was measured after 3 hours, and the IC$_{50}$ value of inhibitory activity was calculated on conditions that absorbance of the well containing no compound and no cell was 100%, and absorbance of the well containing the cell and no compound was 0%.

The proliferation inhibitory activity of the representative compounds of the present invention against OCI-Ly10 strain is shown in Table 7.

TABLE 7

| Tested Compounds Example No. | Proliferation Inhibitory Activity IC$_{50}$ (μM) |
|---|---|
| 2 | 0.068 |
| 8 | 0.004 |
| 13 | 0.027 |
| 23 | 0.020 |
| 26 | 0.075 |
| 27 | 0.182 |
| 29 | 0.332 |
| 31 | 0.045 |
| 32 | 0.079 |
| 33 | 0.197 |
| 34 | 0.102 |
| 35 | 0.428 |
| 36 | 0.450 |

TABLE 7-continued

| Tested Compounds Example No. | Proliferation Inhibitory Activity IC$_{50}$ (μM) |
|---|---|
| 37 | 0.499 |
| 38 | 0.366 |
| 39 | 1.053 |
| 40 | 1.334 |
| 41 | 0.017 |
| 42 | 0.097 |
| 43 | 0.194 |
| 44 | 0.885 |
| 45 | 0.134 |
| 46 | 0.564 |
| 47 | 0.204 |
| 48 | 0.054 |
| 49 | 0.088 |
| 50 | 0.052 |
| 51 | 0.010 |
| 52 | 0.015 |
| 53 | 0.025 |
| 54 | 0.017 |
| 55 | 0.013 |
| 56 | 0.412 |
| 58 | 0.027 |
| 59 | 0.063 |
| 60 | 0.064 |
| 61 | 0.005 |
| 62 | 0.015 |
| 63 | 0.016 |
| 64 | 0.642 |
| 65 | 0.276 |
| 66 | 0.018 |
| 67 | 0.082 |
| 68 | 0.115 |
| 69 | 0.005 |
| 70 | 0.004 |
| 71 | 0.006 |
| 72 | 0.127 |
| 73 | 0.011 |
| 74 | 0.013 |
| 75 | 0.010 |
| 76 | 0.047 |
| 77 | 0.062 |
| 78 | 0.050 |
| 79 | 0.030 |
| 80 | 0.070 |
| 81 | 0.175 |
| 82 | 0.024 |
| 83 | 0.008 |
| 84 | 0.006 |
| 85 | 0.024 |
| 86 | 0.013 |
| 87 | 0.004 |
| 88 | 0.007 |
| 89 | 0.010 |
| 90 | 0.013 |
| 91 | 0.038 |

TABLE 7-continued

| Tested Compounds Example No. | Proliferation Inhibitory Activity IC$_{50}$ (μM) |
|---|---|
| 92 | 0.061 |
| 93 | 0.098 |

As demonstrated in results of the Test Example 4, compounds (I) of the present invention have proliferation inhibitory activity against OCI-Ly10 strain.

INDUSTRIAL APPLICABILITY

The present invention provides with a compound useful for preventing or treating diseases which are known to be involved in abnormal cell response through BTK, for example, self-immune diseases, inflammatory diseases, bone diseases, and cancers such as lymphoma. The compound is also useful, as a BTK inhibitor, for reagents to be used in tests and researches.

The invention claimed is:

1. An oxoisoquinoline compound of the following formula:

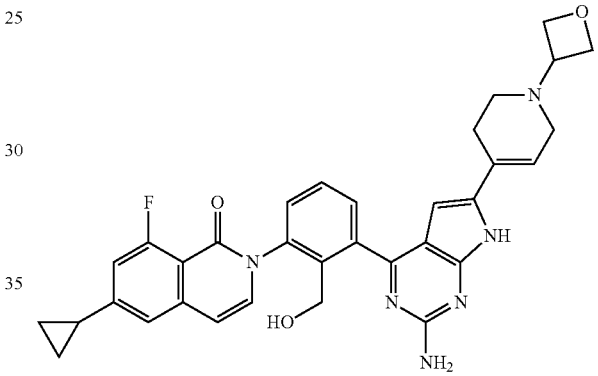

or a pharmaceutically acceptable salt thereof.

2. A pharmaceutical composition comprising the compound according to claim 1 or a pharmaceutically acceptable salt thereof and a pharmaceutically acceptable carrier.

3. A method for treating B-cell lymphoma, comprising administering a therapeutically effective amount of the compound according to claim 1 or a pharmaceutically acceptable salt thereof to a patient in need thereof.

* * * * *